(12) United States Patent
Papeo et al.

(10) Patent No.: US 8,765,972 B2
(45) Date of Patent: *Jul. 1, 2014

(54) 3-OXO-2,3-DIHYDRO-1H-ISOINDOLE-4-CARBOXAMIDES WITH SELECTIVE PARP-1 INHIBITION

(75) Inventors: Gianluca Mariano Enrico Papeo, Cernusco Lombardone (IT); Alina Anatolievna Busel, Moscow (RU); Elena Casale, Somma Lombardo (IT); Alexander Khvat, San Diego, CA (US); Mikhail Yurievitch Krasavin, Nathan Qld (AU); Paolo Orsini, Legnano (IT); Helena Posteri, Travedona Monate (IT); Alessandra Scolaro, Bresso (IT)

(73) Assignee: Nerviano Medical Sciences S.r.l., Nerviano (MI) (IT)

( * ) Notice: Subject to any disclaimer, the term of this patent is extended or adjusted under 35 U.S.C. 154(b) by 0 days.

This patent is subject to a terminal disclaimer.

(21) Appl. No.: 13/383,611

(22) PCT Filed: Jul. 6, 2010

(86) PCT No.: PCT/EP2010/059668
§ 371 (c)(1),
(2), (4) Date: Jun. 15, 2012

(87) PCT Pub. No.: WO2011/006803
PCT Pub. Date: Jan. 20, 2011

(65) Prior Publication Data
US 2012/0245143 A1    Sep. 27, 2012

(30) Foreign Application Priority Data
Jul. 14, 2009  (EP) .................................. 09165446

(51) Int. Cl.
*A61K 31/40*   (2006.01)
*C07D 209/44*  (2006.01)

(52) U.S. Cl.
USPC ......................................... 548/470; 514/418

(58) Field of Classification Search
None
See application file for complete search history.

(56) References Cited

U.S. PATENT DOCUMENTS 8,143,284 B2 *   3/2012  Gandhi et al. ................ 514/323
2008/0108659 A1  5/2008  Gandhi et al.

FOREIGN PATENT DOCUMENTS

| WO | WO 2007/041357 A1 | 4/2007 |
| WO | WO 2007/113596 A1 | 10/2007 |
| WO | WO 2009/012280 A2 | 1/2009 |

OTHER PUBLICATIONS

Silverman, R. "The Organic Chemistry of Drug Design and Drug Action," 2004, Elsevier, pp. 29-32.*
International Search Report issued in PCT/EP2010/059668, dated Aug. 23, 2010.

* cited by examiner

*Primary Examiner* — Heidi Reese
(74) *Attorney, Agent, or Firm* — Scully, Scott, Murphy & Presser, P.C.

(57) ABSTRACT

There are provided substituted 3-oxo-2,3-dihydro-1H-isoindole-4-carboxamide derivatives (I) which selectively inhibit the activity of poly (ADP-ribose) polymerase PARP-1 with respect to poly (ADP-ribose) polymerase PARP-2. The compounds of this invention are therefore useful in treating diseases such as cancer, cardiovascular diseases, central nervous system injury and different forms of inflammation. The present invention also provides methods for preparing these compounds, pharmaceutical compositions comprising these compounds, and methods of treating diseases utilizing pharmaceutical compositions comprising these compounds.

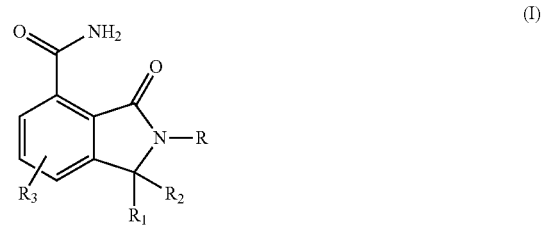

9 Claims, No Drawings

3-OXO-2,3-DIHYDRO-1H-ISOINDOLE-4-CARBOXAMIDES WITH SELECTIVE PARP-1 INHIBITION

The present invention provides substituted 3-oxo-2,3-dihydro-1H-isoindole-4-carboxamide derivatives which selectively inhibit the activity of poly (ADP-ribose) polymerase PARP-1 with respect to poly (ADP-ribose) polymerase PARP-2. The compounds of this invention are therefore useful in treating diseases such as cancer, cardiovascular diseases, central nervous system injury and different forms of inflammation. The present invention also provides methods for preparing these compounds, pharmaceutical compositions comprising these compounds, and methods of treating diseases utilizing pharmaceutical compositions comprising these compounds.

Poly (ADP-ribose) polymerases belong to a family of 18 members that catalyze the addition of ADP-ribose units to DNA or different acceptor proteins, which affect cellular processes as diverse as replication, transcription, differentiation, gene regulation, protein degradation and spindle maintenance. PARP-1 and PARP-2 are the only enzymes among the PARPs that are activated by DNA damage and are involved in DNA repair.

PARP-1 is a nuclear protein consisting of three domains: the N-terminal DNA-binding domain containing two zinc fingers, the auto modification domain, and the C-terminal catalytic domain. PARP-1 binds through the zinc-finger domain to DNA single strand breaks (SSB), cleaves NAD+, and attaches multiple ADP-ribose units to target proteins such as histones and various DNA repair enzymes. This results in a highly negatively charged target, which in turn leads to the unwinding and repair of the damaged DNA through the base excision repair pathway. In knock out mouse models, deletion of PARP-1 impairs DNA repair but it is not embryonic lethal. Double knock out PARP-1 and PARP-2 mice instead die during early embryogenesis, suggesting that the two enzymes display not completely overlapping functions. Enhanced PARP-1 expression and/or activity have been shown in different tumor cell lines, including malignant lymphomas, hepatocellular carcinoma, cervical carcinoma, colorectal carcinoma, leukemia. This may allow tumor cells to withstand genotoxic stress and increase their resistance to DNA-damaging agents. As a consequence, inhibition of PARP-1 through small molecules has been shown to sensitize tumor cells to cytotoxic therapy (e.g. temozolomide, platinums, topoisomerase inhibitors and radiation). A significant window seems to exist between the ability of a PARP inhibitor to potentiate therapeutic benefits and undesirable side effects. Whereas the therapeutic use of PARP inhibitors in combination with DNA damaging agents is not novel, the use of these agents as monotherapy, in particular tumor genetic backgrounds deficient in the homologous recombination DNA repair, represents a new approach. Individuals with heterozygous germ line mutations in either the BRCA-1 or BRCA-2 homologous recombination repair genes exhibit high life time risks of developing breast and other cancers. Tumors arising in mutation carriers have generally lost the wild type allele and do not express functional BRCA-1 and BRCA-2 proteins.

Therefore, loss of these two proteins leads to a tumor-specific dysfunction in the repair of double strand breaks by homologous recombination. It is known that when PARP-1 is inhibited, base excision repair is reduced and single strand breaks that are generated during the normal cell cycle persist. It has also been established that replication forks that encounter an unrepaired break can form double strand breaks which are normally repaired by homologous recombination. Tumor cells that are deficient in homologous recombination repair such as BRCA-1 and BRCA-2 mutants are therefore highly sensitive to PARP inhibition compared with wild-type cells. This is in line with the concept of synthetic lethality, in which the two pathway defects alone are innocuous but combined become lethal: PARP inhibitors may be more effective in patients with tumors with specific DNA repair defects without affecting normal heterozygous tissues. Putative patient population includes, besides BRCA mutants that represent the majority of hereditary breast and ovarian cancer, also a substantial fraction of sporadic cancers with defects in homologous recombination repair, a phenomenon termed "BRCAness". For example, methylation of the promoters of the BRCA-1 or FANCF genes and amplification of the EMSY gene, which encodes a BRCA-2 interacting protein. By extending the rational of synthetic lethality of PARP and BRCA-1 and BRCA-2, it is likely that deficiencies in any gene that is not redundant in double strand break repair should be sensitive to PARP inhibition. For example, ATM deficiency, found in patients with T-cell prolymhocytic leukemia and B-cell chronic lymphocitic leukemia and breast cancer and CHK2 germ line mutations identified in sarcoma, breast cancer, ovarian cancer and brain tumors, have also been shown to be synthetically lethal in combination with PARP deficiency as well as deficiencies in other known HR pathway proteins (including RAD51, DSS1, RAD54, RPA1, NBS1, ATR, CHK1, CHK2, FANCD2, FANCA, and FANCC).

Mutations in FANCC and FANCG have been shown in pancreatic cancer. Methylation of FANCF promoter has been found in ovarian, breast, cervical, lung carcinomas. The first clinical evidence that BRCA-mutated cancer may be sensitive to PARP inhibitor monotherapy comes from the preliminary data for the phase I trial of the oral, small molecule PARP inhibitor AZD2281. In an enriched phase I population for BRCA mutation carriers, partial responses were seen in 4 out of 10 ovarian cancer patients with confirmed BRCA-1 mutations. Other PARP inhibitors, such as AG014699, BSI-201, are currently known to be in phase II clinical trials both in combination with DNA damaging agents and as single agent in BRCA deficient tumors. Early indications are that these therapies show low toxicity. Anyway compounds with high selectivity on PARP-1 are expected to show even less toxicity in view of a chronic treatment schedule.

PARP-1 has also been implicated in angiogenesis. In particular, PARP-1 inhibition seems to result in decreased accumulation of the transcription hypoxia-inducible factor 1α, an important regulator of tumor cell adaptation to hypoxia.

Pro-inflammatory stimuli trigger the release of pro-inflammatory mediators that induce the production of peroxynitrate and hydroxyl radicals, which in turn yield to DNA single strand breakage with consequent activation of PARP-1. Over activation of PARP-1 results in depletion of NAD+ and energy stores, culminating in cell dysfunction and necrosis. This cellular suicide mechanism has been implicated in the pathomechanism of stroke, myocardial ischemia, diabetes, diabetes-associated cardiovascular dysfunction, shock, traumatic central nervous system injury, arthritis, colitis, allergic encephalomyelitis and various other forms of inflammation. Of special interest is the enhancement by PARP-1 of nuclear factor kB-mediated transcription, which plays a central role in the expression of inflammatory cytokines, chemokines and inflammatory mediators.

WO2007047646 in the name of Janssen Pharmaceutica describes substituted dihydro isoindolones useful for treating kinase disorders; Wender et al. claim in U.S. Pat. No. 7,232,842 isoindolone analogs as kinase inhibitors. The Patent Application Publication US 2008/0108659 of Gandhi et al.

describes 3-oxo-2,3-dihydro-1H-isoindoles as poly (ADP-Ribose) polymerase inhibitors, also reported in: *Bioorg. Med. Chem. Lett.*, 2010, 20, 1023-1026. The present invention provides novel 1H-isoindole derivatives which are selective PARP-1 inhibitors with respect to PARP-2 and are thus useful in the therapy of cancer, cardiovascular diseases, nervous system injury and inflammation.

Accordingly, a first object of the present invention is to provide a compound of the formula (I):

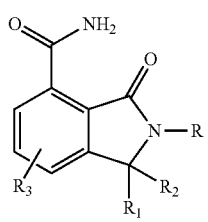

(I)

wherein
R is an optionally substituted linear or branched $C_1$-$C_6$ alkyl, $C_2$-$C_6$ alkenyl, $C_2$-$C_6$ alkynyl, $C_3$-$C_7$ cycloalkyl, heterocyclyl, aryl or heteroaryl group;
$R_1$ and $R_2$ are independently hydrogen atom, an optionally substituted linear or branched $C_1$-$C_6$ alkyl, $C_2$-$C_6$ alkenyl, $C_2$-$C_6$ alkynyl, $C_3$-$C_7$ cycloalkyl, heterocyclyl, aryl or heteroaryl group, or, taken together with the ring carbon atom to which they are bonded, form an optionally substituted carbon-carbon double bond, a $C_3$-$C_7$ cycloalkyl or heterocyclyl group, with the proviso that $R_1$ and $R_2$ are not both hydrogen atoms;
$R_3$ is hydrogen or halogen atom, cyano, nitro or an optionally substituted linear or branched $C_1$-$C_6$ alkyl, $C_2$-$C_6$ alkenyl, $C_2$-$C_6$ alkynyl, $C_3$-$C_7$ cycloalkyl, heterocyclyl, aryl, heteroaryl, $NHCOR_4$, $COR_4$, $NR_5R_6$, $NR_5COR_4$, $OR_7$, $SR_7$, $SOR_{10}$, $SO_2R_{10}$, $NHSOR_{10}$, $NHSO_2R_{10}$, $R_8R_9N$—$C_1$-$C_6$ alkyl or $R_8O$—$C_1$-$C_6$ alkyl group;
$R_4$ is hydrogen atom or an optionally substituted linear or branched $C_1$-$C_6$ alkyl, $C_3$-$C_7$ cycloalkyl, heterocyclyl, aryl, heteroaryl, $NR_5R_7$, $OR_7$, $SR_7$, $R_8R_9N$—$C_1$-$C_6$ alkyl or $R_8O$—$C_1$-$C_6$ alkyl group;
$R_5$ and $R_6$ are independently hydrogen atom, or an optionally substituted linear or branched $C_1$-$C_6$ alkyl, $C_3$-$C_7$ cycloalkyl, $C_2$-$C_6$ alkenyl, $C_2$-$C_6$ alkynyl, heterocyclyl, aryl, heteroaryl, $R_8R_9N$—$C_1$-$C_6$ alkyl, $R_8O$—$C_1$-$C_6$ alkyl group, or $R_5$ and $R_6$, taken together with the nitrogen atom to which they are bonded, form an optionally substituted heterocyclyl group;
$R_7$ is hydrogen atom, or an optionally substituted linear or branched $C_1$-$C_6$ alkyl, $C_3$-$C_7$ cycloalkyl, $C_2$-$C_6$ alkenyl, $C_2$-$C_6$ alkynyl, heterocyclyl, aryl, heteroaryl, $COR_5$, $SOR_{10}$, $SO_2R_{10}$, $R_8R_9N$—$C_1$-$C_6$ alkyl, $R_8O$—$C_1$-$C_6$ alkyl, heterocyclyl-$C_1$-$C_6$ alkyl, aryl-$C_1$-$C_6$ alkyl or heteroaryl-$C_1$-$C_6$ alkyl group, wherein $R_5$ is as defined above;
$R_8$ and $R_9$ are independently hydrogen atom or an optionally substituted linear or branched $C_1$-$C_6$ alkyl, $C_3$-$C_7$ cycloalkyl, $C_2$-$C_6$ alkenyl, $C_2$-$C_6$ alkynyl, heterocyclyl, aryl, heteroaryl, $COR_4$, or $R_8$ and $R_9$, taken together with the nitrogen atom to which they are bonded, form an optionally substituted heterocyclyl group, wherein $R_4$ is as defined above;
$R_{10}$ is hydrogen atom, or an optionally substituted linear or branched $C_1$-$C_6$ alkyl, $C_3$-$C_7$ cycloalkyl, $C_2$-$C_6$ alkenyl, $C_2$-$C_6$ alkynyl, heterocyclyl, aryl, heteroaryl, $NR_5R_6$, $OR_7$, $R_8R_9N$—$C_1$-$C_6$ alkyl, $R_8O$—$C_1$-$C_6$ alkyl, wherein $R_5$, $R_6$, $R_7$, $R_8$ and $R_9$ are as defined above;
or a pharmaceutically acceptable salt thereof.

The compounds of formula (I) are potent and selective PARP-1 inhibitors with respect to PARP-2 and are thus useful in cancer, cardiovascular diseases, nervous system injury and inflammation therapy.

The present invention also provides methods of synthesizing 3-oxo-2,3-dihydro-1H-isoindole-4-carboxamide derivatives of formula (I) prepared through a process consisting of standard synthetic transformations.

The present invention also provides methods for treating diseases mediated by the PARP-1 protein.

A preferred method of the present invention is to treat a disease mediated by PARP-1 protein selected from the group consisting of cancer, cardiovascular diseases, nervous system injury and inflammation.

Another preferred method of the present invention is to treat specific types of cancer including but not limited to: carcinoma such as bladder, breast, colon, kidney, liver, lung, including small cell lung cancer, esophagus, gallbladder, ovary, pancreas, stomach, cervix, thyroid, prostate, and skin, including squamous cell carcinoma; hematopoietic tumors of lymphoid lineage including leukaemia, acute lymphocytic leukaemia, acute lymphoblastic leukaemia, B-cell lymphoma, T-cell-lymphoma, Hodgkin's lymphoma, non-Hodgkin's lymphoma, hairy cell lymphoma and Burkitt's lymphoma; hematopoietic tumors of myeloid lineage, including acute and chronic myelogenous leukemias, myelodysplastic syndrome and promyelocytic leukaemia; tumors of mesenchymal origin, including fibrosarcoma and rhabdomyosarcoma; tumors of the central and peripheral nervous system, including astrocytoma, neuroblastoma, glioma and schwannomas; other tumors, including melanoma, seminoma, teratocarcinoma, osteosarcoma, xeroderma pigmentosum, keratoxanthoma, thyroid follicular cancer and Kaposi's sarcoma.

Another preferred method of the present invention is to treat specific types of cardiovascular diseases including but not limited to: myocardial reperfusion injury, cardiomyopathy, diabetic cardiovascular dysfunction.

Another preferred method of the present invention is to treat specific types of central nervous system injury including but not limited to stroke, brain injury and neurodegenerative disorders.

The present invention further provides a method of treatment comprising a compound of formula (I) in combination with radiation therapy or chemotherapy regimen for simultaneous, separate or sequential use in anticancer therapy. Moreover the invention provides an in vitro method for selectively inhibiting the PARP-1 protein activity which comprises contacting the said protein with an effective amount of a compound of formula (I).

The present invention also provides a pharmaceutical composition comprising one or more compounds of formula (I) or a pharmaceutically acceptable salt thereof and a pharmaceutically acceptable excipient, carrier or diluent.

The present invention also provides a pharmaceutical composition comprising a compound of formula (I) in combination with known cytostatic or cytotoxic agents, antibiotic-type agents, alkylating agents, antimetabolite agents, hormonal agents, immunological agents, interferon-type agents, cyclooxygenase inhibitors (e.g. COX-2 inhibitors), matrix metalloprotease inhibitors, telomerase inhibitors, tyrosine kinase inhibitors, anti-growth factor receptor agents, anti-HER agents, anti-EGFR agents, anti-angiogenesis agents (e.g. angiogenesis inhibitors), farnesyl transferase inhibitors, ras-raf signal transduction pathway inhibitors, cell cycle inhibitors, other cdks inhibitors, tubulin binding agents, topoisomerase I inhibitors, topoisomerase II inhibitors, and the like. Additionally, the invention provides a product or kit comprising a compound of formula (I) or a pharmaceutically acceptable salt thereof, as defined above, or pharmaceutical compositions thereof and one or more chemotherapeutic agents, as a combined preparation for simultaneous, separate or sequential use in anticancer therapy.

In yet another aspect, the invention provides a compound of formula (I) or a pharmaceutically acceptable salt thereof, as defined above, for use as a medicament, preferably as a medicament with antitumor activity.

Moreover the invention provides the use of a compound of formula (I) or a pharmaceutically acceptable salt thereof, as defined above, in the manufacture of a medicament with antitumor activity.

Finally, the invention provides a compound of formula (I) or a pharmaceutically acceptable salt thereof, as defined above, for use in a method of treating cancer.

The compounds of formula (I) may have one or more asymmetric centers, and may therefore exist as individual optical isomers or racemic mixtures or diastereoisomer. Accordingly, all the possible isomers, and their mixtures of the compounds of formula (I) are within the scope of the present invention. As stated above, salts of the compounds of formula (I) are also within the scope of the present invention.

Unless otherwise specified, when referring to the compounds of formula (I) per se as well as to any pharmaceutical composition thereof or to any therapeutic treatment comprising them, the present invention includes all of the isomers, tautomers, hydrates, solvates, N-oxides and pharmaceutically acceptable salts of the compounds of this invention.

If a chiral center or another form of an isomeric center is present in a compound of the present invention, all forms of such isomer or isomers, including enantiomers and diastereomers, are intended to be covered herein. Compounds containing a chiral center may be used as a racemic mixture, an enantiomerically enriched mixture, or the racemic mixture may be separated using well-known techniques and an individual enantiomer may be used alone. In cases in which compounds have unsaturated carbon-carbon double bonds, both the cis (Z) and trans (E) isomers are within the scope of this invention.

In cases wherein compounds may exist in tautomeric forms, such as keto-enol tautomers, each tautomeric form is contemplated as being included within this invention whether existing in equilibrium or predominantly in one form.

With the term halogen atom we intend a fluorine, chlorine, bromine or iodine atom.

With the term cyano we intend a —CN residue.

With the term nitro we intend a —NO$_2$ group.

With the term "linear or branched C$_1$-C$_6$ alkyl", we intend any of the groups such as, for instance, methyl, ethyl, n-propyl, isopropyl, n-butyl, isobutyl, tert-butyl, sec-butyl, n-pentyl, n-hexyl, and the like.

With the term "C$_2$-C$_6$ alkenyl" we intend an aliphatic C$_2$-C$_6$ hydrocarbon chain containing at least one carbon-carbon double bond and which can be linear or branched. Representative examples include, but are not limited to, ethenyl, 1-propenyl, 2-propenyl, 1- or 2-butenyl, and the like.

With the term "C$_2$-C$_6$ alkynyl" we intend an aliphatic C$_2$-C$_6$ hydrocarbon chain containing at least one carbon-carbon triple bond and which can be linear or branched. Representative examples include, but are not limited to, ethynyl, 1-propynyl, 2-propynyl, 1- or 2-butynyl, and the like.

With the term "C$_3$-C$_7$ cycloalkyl" we intend, unless otherwise provided, a 3- to 7-membered all-carbon monocyclic ring, which may contain one or more double bonds but does not have a completely conjugated π-electron system.

Examples of cycloalkyl groups, without limitation, are cyclopropane, cyclobutane, cyclopentane, cyclopentene, cyclohexane, cyclohexene and cyclohexadiene.

With the term "heterocyclyl" we intend a 3- to 8-membered, saturated or partially unsaturated carbocyclic ring where one or more carbon atoms are replaced by heteroatoms such as nitrogen, oxygen and sulfur. Non limiting examples of heterocyclyl groups are, for instance, pyrane, pyrrolidine, pyrroline, imidazoline, imidazolidine, pyrazolidine, pyrazoline, thiazoline, thiazolidine, dihydrofuran, tetrahydrofuran, 1,3-dioxolane, piperidine, piperazine, morpholine and the like.

The term "aryl" refers to a mono-, bi- or poly-carbocyclic hydrocarbon with from 1 to 4 ring systems, optionally further fused or linked to each other by single bonds, wherein at least one of the carbocyclic rings is "aromatic", wherein the term "aromatic" refers to completely conjugated π-electron bond system. Non limiting examples of such aryl groups are phenyl, α- or β-naphthyl or biphenyl groups.

The term "heteroaryl" refers to aromatic heterocyclic rings, typically 5- to 8-membered heterocycles with from 1 to 3 heteroatoms selected among N, O or S; the heteroaryl ring can be optionally further fused or linked to aromatic and non-aromatic carbocyclic and heterocyclic rings. Not limiting examples of such heteroaryl groups are, for instance, pyridyl, pyrazinyl, pyrimidinyl, pyridazinyl, indolyl, imidazolyl, thiazolyl, isothiazolyl, pyrrolyl, phenyl-pyrrolyl, furyl, phenyl-furyl, oxazolyl, isoxazolyl, pyrazolyl, thienyl, benzothienyl, isoindolinyl, benzoimidazolyl, indazolyl, quinolinyl, isoquinolinyl, 1,2,3-triazolyl, 1-phenyl-1,2,3-triazolyl, 2,3-dihydroindolyl, 2,3-dihydrobenzofuranyl, 2,3-dihydrobenzothiophenyl; benzopyranyl, 2,3-dihydrobenzoxazinyl, 2,3-dihydroquinoxalinyl and the like.

According to the present invention and unless otherwise provided, any of the above R-R$_3$ group may be optionally substituted, in any of their free positions, by one or more groups, for instance 1 to 6 groups, independently selected from: halogen, nitro, oxo groups (=O), cyano, C$_1$-C$_6$ alkyl, polyfluorinated alkyl, polyfluorinated alkoxy, C$_2$-C$_6$ alkenyl, C$_2$-C$_6$ alkynyl, hydroxyalkyl, aryl, arylalkyl, heteroaryl, heteroarylalkyl, heterocyclyl, heterocyclylalkyl, C$_3$-C$_7$ cycloalkyl, hydroxy, alkoxy, aryloxy, heterocyclyloxy, methylenedioxy, alkylcarbonyloxy, arylcarbonyloxy, cycloalkenyloxy, heterocyclylcarbonyloxy, alkylideneaminooxy, carboxy, alkoxycarbonyl, aryloxycarbonyl, cycloalkyloxycarbonyl, heterocyclylalkyloxycarbonylamino, ureido, alkylamino, dialkylamino, arylamino, diarylamino, heterocyclylamino, formylamino, alkylcarbonylamino, arylcarbonylamino, heterocyclylcarbonylamino, aminocarbonyl, alkylaminocarbonyl, dialkylaminocarbonyl, arylaminocarbonyl, heterocyclylaminocarbonyl, alkoxycarbonylamino, hydroxyaminocarbonyl alkoxyimino, alkylsulfonylamino, arylsulfonylamino, heterocyclylsulfonylamino, formyl, alkylcarbonyl, arylcarbonyl, cycloalkylcarbonyl, heterocyclylcarbonyl, alkylsulfonyl, arylsulfonyl, aminosulfonyl, alkylaminosulfonyl, dialkylaminosulfonyl, arylaminosulfonyl, heterocyclylaminosulfonyl, arylthio, alkylthio, phosphonate and alkylphosphonate. In their turn, whenever appropriate, each of the above substituent may be further substituted by one or more of the aforementioned groups.

With the term polyfluorinated alkyl or polyfluorinated alkoxy we intend any of the above linear or branched C$_1$-C$_6$ alkyl or alkoxy groups which are substituted by more than one fluorine atom such as, for instance, trifluoromethyl, trifluoroethyl, 1,1,1,3,3,3-hexafluoropropyl, trifluoromethoxy and the like.

With the term hydroxyalkyl we intend any of the above $C_1$-$C_6$ alkyl, bearing an hydroxyl group such as, for instance, hydroxymethyl, 2-hydroxyethyl, 3-hydroxypropyl and the like.

From all of the above, it is clear to the skilled person that any group which name is a composite name such as, for instance, arylamino has to be intended as conventionally construed by the parts from which it derives, e.g. by an amino group which is further substituted by aryl, wherein aryl is as above defined.

Likewise, any of the terms such as, for instance, alkylthio, alkylamino, dialkylamino, alkoxycarbonyl, alkoxycarbonylamino, heterocyclylcarbonyl, heterocyclylcarbonylamino, cycloalkyloxycarbonyl and the like, include groups wherein the alkyl, alkoxy, aryl, $C_3$-$C_7$ cycloalkyl and heterocyclyl moieties are as above defined.

In particular, in the above definition, "optionally substituted" means that the group may be substituted with one or more substituents independently selected from linear or branched $C_1$-$C_6$ alkyl, $C_2$-$C_6$ alkenyl, $C_2$-$C_6$ alkynyl, $C_3$-$C_7$ cycloalkyl, heterocyclyl, aryl, heteroaryl, $C_3$-$C_7$ cycloalkyl-$C_1$-$C_6$ alkyl, heterocyclyl-$C_1$-$C_6$ alkyl, aryl-$C_1$-$C_6$ alkyl or heteroaryl-$C_1$-$C_6$ alkyl group, halogen, cyano, nitro, NHCOR$_4$, COR$_4$, NR$_5$R$_6$, NR$_5$COR$_4$, OR$_7$, oxo (=O), SR$_7$, SOR$_{10}$, SO$_2$R$_{10}$, NHSOR$_{10}$, NHSO$_2$R$_{10}$, R$_8$R$_9$N—C$_1$-C$_6$ alkyl, R$_8$O—C$_1$-C$_6$ alkyl group.

All those substituents may be optionally further substituted with one or more substituents independently selected from halogen, $C_1$-$C_6$ alkyl, aryl or heterocyclyl group, NHCOR$_4$, NR$_5$R$_6$, NR$_5$COR$_4$, OR$_7$, oxo (=O), SR$_7$, R$_8$R$_9$N—C$_1$-C$_6$ alkyl, R$_8$O—C$_1$-C$_6$ alkyl, wherein R$_4$, R$_5$, R$_6$, R$_7$, R$_8$, R$_9$ and R$_{10}$ are as defined above.

The term "pharmaceutically acceptable salt" of compounds of formula (I) refers to those salts that retain the biological effectiveness and properties of the parent compound, therefore pharmaceutically acceptable salts of the compounds of formula (I) include the acid addition salts with inorganic or organic acids, e.g., nitric, hydrochloric, hydrobromic, sulfuric, perchloric, phosphoric, acetic, trifluoroacetic, propionic, glycolic, (D) or (L) lactic, oxalic, ascorbic, fumaric, malonic, malic, maleic, tartaric, citric, benzoic, cinnamic, mandelic, methanesulphonic, ethanesulfonic, p-toluenesulfonic, isethionic, succinic and salicylic acid.

Pharmaceutically acceptable salts of the compounds of formula (I) also include the salts with inorganic or organic bases, e.g., alkali or alkaline-earth metals, especially sodium, potassium, calcium, ammonium or magnesium hydroxides, carbonates or bicarbonates, acyclic or cyclic amines, preferably methylamine, ethylamine, diethylamine, triethylamine, piperidine and the like.

In a first preferred embodiment, compounds of general formula (I) are characterized in that R is an optionally substituted $C_3$-$C_7$ cycloalkyl, heterocyclyl, aryl or heteroaryl group, the optional substituents being one or more halogen, cyano, an optionally further substituted linear or branched $C_1$-$C_6$ alkyl, $C_3$-$C_7$ cycloalkyl, heterocyclyl, aryl, heteroaryl, $C_3$-$C_7$ cycloalkyl-$C_1$-$C_6$ alkyl, heterocyclyl-$C_1$-$C_6$ alkyl, aryl-$C_1$-$C_6$ alkyl or heteroaryl-$C_1$-$C_6$ alkyl group, NHCOR$_4$, COR$_4$, NR$_5$R$_6$, NR$_5$COR$_4$, OR$_7$, oxo (=O), R$_8$R$_9$N—C$_1$-C$_6$ alkyl or R$_8$O—C$_1$-C$_6$ alkyl, the optional further substituents being one or more halogen, $C_1$-$C_6$ alkyl, aryl or heterocyclyl group, NHCOR$_4$, NR$_5$R$_6$, NR$_5$COR$_4$, OR$_7$, oxo (=O), SR$_7$, R$_8$R$_9$N—C$_1$-C$_6$ alkyl or R$_8$O—C$_1$-C$_6$ alkyl, and R$_1$, R$_2$, R$_3$, R$_4$, R$_5$, R$_6$, R$_7$, R$_8$ and R$_9$ have the meanings above defined,
or a pharmaceutically acceptable salt thereof.

In a second preferred embodiment, compounds of general formula (I) are characterized in that R is an optionally substituted $C_3$-$C_7$ cycloalkyl, heterocyclyl, aryl or heteroaryl group, the optional substituents being one or more halogen, cyano, an optionally further substituted linear or branched $C_1$-$C_6$ alkyl, $C_3$-$C_7$ cycloalkyl, heterocyclyl, aryl, heteroaryl or $C_3$-$C_7$ cycloalkyl-$C_1$-$C_6$ alkyl, heterocyclyl-$C_1$-$C_6$ alkyl, aryl-$C_1$-$C_6$ alkyl or heteroaryl-$C_1$-$C_6$ alkyl group, NHCOR$_4$, COR$_4$, NR$_5$R$_6$, NR$_5$COR$_4$, OR$_7$, oxo (=O), R$_8$R$_9$N—C$_1$-C$_6$ alkyl or R$_8$O—C$_1$-C$_6$ alkyl, the optional further substituents being one or more halogen, $C_1$-$C_6$ alkyl, aryl or heterocyclyl group, NHCOR$_4$, NR$_5$R$_6$, NR$_5$COR$_4$, OR$_7$, oxo (=O), SR$_7$, R$_8$R$_9$N—C$_1$-C$_6$ alkyl or R$_8$O—C$_1$-C$_6$ alkyl;
either R$_1$ is hydrogen atom, and R$_2$ is an optionally substituted linear or branched $C_1$-$C_6$ alkyl, $C_2$-$C_6$ alkenyl, $C_2$-$C_6$ alkynyl, $C_3$-$C_7$ cycloalkyl, heterocyclyl, aryl or heteroaryl group, or R$_1$ and R$_2$, taken together with the ring carbon atom to which they are linked, form an optionally substituted carbon-carbon double bond, a $C_3$-$C_7$ cycloalkyl or heterocyclyl group, and R$_3$, R$_4$, R$_5$, R$_6$, R$_7$, R$_8$ and R$_9$ have the meanings above defined,
or a pharmaceutically acceptable salt thereof.

In a third preferred embodiment, compounds of general formula (I) are characterized in that R is an optionally substituted $C_3$-$C_7$ cycloalkyl, heterocyclyl, aryl or heteroaryl group, the optional substituents being one or more halogen, cyano, an optionally further substituted linear or branched $C_1$-$C_6$ alkyl, $C_3$-$C_7$ cycloalkyl, heterocyclyl, aryl, heteroaryl, $C_3$-$C_7$ cycloalkyl-$C_1$-$C_6$ alkyl, heterocyclyl-$C_1$-$C_6$ alkyl, aryl-$C_1$-$C_6$ alkyl or heteroaryl-$C_1$-$C_6$ alkyl group, NHCOR$_4$, COR$_4$, NR$_5$R$_6$, NR$_5$COR$_4$, OR$_7$, oxo (=O), R$_8$R$_8$N—C$_1$-C$_6$ alkyl or R$_8$O—C$_1$-C$_6$ alkyl, the optional further substituents being one or more halogen, $C_1$-$C_6$ alkyl, aryl or heterocyclyl group, NHCOR$_4$, NR$_5$R$_6$, NR$_5$COR$_4$, OR$_7$, oxo (=O), SR$_7$, R$_8$R$_8$N—C$_1$-C$_6$ alkyl or R$_8$O—C$_1$-C$_6$ alkyl group;
either R$_1$ is hydrogen atom, and R$_2$ is an optionally substituted linear or branched $C_1$-$C_6$ alkyl, $C_2$-$C_6$ alkenyl, $C_2$-$C_6$ alkynyl, $C_3$-$C_7$ cycloalkyl, heterocyclyl, aryl or heteroaryl group, or R$_1$ and R$_2$, taken together with the ring carbon atom to which they are linked, form an optionally substituted carbon-carbon double bond, a $C_3$-$C_7$ cycloalkyl or heterocyclyl group;
R$_3$ is hydrogen, halogen atom, cyano, nitro, an optionally substituted linear or branched $C_1$-$C_6$alkyl, $C_2$-$C_6$alkenyl, $C_2$-$C_6$ alkynyl, NHCOR$_4$, NR$_5$R$_6$, NR$_5$COR$_4$, OR$_7$, R$_8$R$_8$N—C$_1$-C$_6$ alkyl or R$_8$O—C$_1$-C$_6$ alkyl, and R$_4$, R$_5$, R$_6$, R$_7$, R$_8$, and R$_9$ are as defined above,
or a pharmaceutically acceptable salt thereof.

Even more preferably, the present invention provides compounds of the formula (I) as defined above characterized in that:
R is an optionally substituted heterocyclyl or aryl group, the optional substituents being, one or more, optionally further substituted linear or branched $C_1$-$C_6$ alkyl, $C_3$-$C_7$ cycloalkyl, heterocyclyl, aryl, heteroaryl, $C_3$-$C_7$ cycloalkyl-$C_1$-$C_6$alkyl, heterocyclyl-$C_1$-$C_6$alkyl, aryl-$C_1$-$C_6$alkyl or heteroaryl-$C_1$-$C_6$alkyl group or COR$_4$, and, the optional further substituents being one or more halogen, $C_1$-$C_6$ alkyl, aryl or heterocyclyl group, OR$_7$, oxo (=O), SR$_7$, or R$_8$O—C$_1$-C$_6$ alkyl group;
R$_1$ and R$_2$ are independently hydrogen atom or a $C_1$-$C_6$ alkyl group, with the proviso that they are not both hydrogen atoms;
R$_3$ is hydrogen or halogen atom;
R$_4$ is OR$_7$,
R$_7$ is hydrogen atom, optionally substituted $C_1$-$C_6$ alkyl or aryl-$C_1$-$C_6$ alkyl group, substituents being one or more halogen atom;

$R_8$ is hydrogen atom, and $R_5$, $R_6$ and $R_9$ are as defined above, or a pharmaceutically acceptable salt thereof.

Other preferred compounds provided from the present invention are the compounds of the formula (I) as defined above characterized in that R is an optionally substituted piperidinyl or phenyl group, the optional substituents being, one or more, optionally further substituted methyl, ethyl, propyl, cyclohexyl, cyclopentyl, cyclobutyl, morpholinyl, piperazinyl, pyrazolyl, cyclohexyl-methyl, cyclohexenyl-methyl, piperidinyl-methyl, benzyl, pyridyl-methyl, pyrrolyl-methyl, pyrazolyl-methyl, imidazolyl-methyl, thienyl-methyl, indolyl-methyl, thiazolyl-methyl, furyl-methyl group or $COR_4$; the optional further substituents being one or more bromine, fluorine, chlorine atom or isopropyl, methyl, phenyl, morpholinyl, or piperidinyl, hydroxy-methyl group, $OR_7$, oxo (=O) or $SR_7$;

$R_1$ and $R_2$ are independently hydrogen atom or a methyl group, with the proviso that they are not both hydrogen atoms;

$R_3$ is hydrogen or fluorine atom;

$R_4$ is $OR_7$, $R_7$ is hydrogen atom, an optionally substituted methyl, tert-butyl or benzyl group, the substituents being one or more fluorine atom, and $R_5$, $R_6$, $R_8$, and $R_9$ are as defined above, or a pharmaceutically acceptable salt thereof.

Specific compounds of the present invention are listed below:

1. tert-butyl 4-(4-carbamoyl-1-methyl-3-oxo-1,3-dihydro-2H-isoindol-2-yl)piperidine-1-carboxylate,
2. 1-methyl-3-oxo-2-(piperidin-4-yl)-2,3-dihydro-1H-isoindole-4-carboxamide,
3. 2-(1-cyclohexylpiperidin-4-yl)-1-methyl-3-oxo-2,3-dihydro-1H-isoindole-4-carboxamide,
4. (1S)-2-(1-cyclohexylpiperidin-4-yl)-1-methyl-3-oxo-2,3-dihydro-1H-isoindole-4-carboxamide,
5. (1R)-2-(1-cyclohexylpiperidin-4-yl)-1-methyl-3-oxo-2,3-dihydro-1H-isoindole-4-carboxamide,
6. 2-[1-(4,4-difluorocyclohexyl)piperidin-4-yl]-1-methyl-3-oxo-2,3-dihydro-1H-isoindole-4-carboxamide,
7. 2-[1-(1H-indol-5-ylmethyl)piperidin-4-yl]-1-methyl-3-oxo-2,3-dihydro-1H-isoindole-4-carboxamide,
8. 1-methyl-3-oxo-2-(1-{[1-(propan-2-yl)-1H-indol-3-yl]methyl}piperidin-4-yl)-2,3-dihydro-1H-isoindole-4-carboxamide,
9. 1-methyl-3-oxo-2-[1-(pyridin-2-ylmethyl)piperidin-4-yl]-2,3-dihydro-1H-isoindole-4-carboxamide,
10. 2-(1-{[4-(benzyloxy)-1H-indol-3-yl]methyl}piperidin-4-yl)-1-methyl-3-oxo-2,3-dihydro-1H-isoindole-4-carboxamide,
11. 1-methyl-2-{1-[(4-methyl-1,3-thiazol-5-yl)methyl]piperidin-4-yl}-3-oxo-2,3-dihydro-1H-isoindole-4-carboxamide,
12. 2-[1-(2,4-difluorobenzyl)piperidin-4-yl]-1-methyl-3-oxo-2,3-dihydro-1H-isoindole-4-carboxamide,
13. 2-(1-cyclopentylpiperidin-4-yl)-1-methyl-3-oxo-2,3-dihydro-1H-isoindole-4-carboxamide,
14. 1-methyl-2-{1-[(6-methylpyridin-2-yl)methyl]piperidin-4-yl}-3-oxo-2,3-dihydro-1H-isoindole-4-carboxamide,
15. 2-[1-(furan-2-ylmethyl)piperidin-4-yl]-1-methyl-3-oxo-2,3-dihydro-1H-isoindole-4-carboxamide,
16. 1-methyl-3-oxo-2-{1-[3-(piperidin-1-yl)benzyl]piperidin-4-yl}-2,3-dihydro-1H-isoindole-4-carboxamide,
17. 1-methyl-2-(1-{[6-(morpholin-4-yl)pyridin-2-yl]methyl}piperidin-4-yl)-3-oxo-2,3-dihydro-1H-isoindole-4-carboxamide,
18. 2-(1-cyclobutylpiperidin-4-yl)-1-methyl-3-oxo-2,3-dihydro-1H-isoindole-4-carboxamide,
19. 1-methyl-3-oxo-2-[1-(1H-pyrrol-2-ylmethyl)piperidin-4-yl]-2,3-dihydro-1H-isoindole-4-carboxamide,
20. 1-methyl-3-oxo-2-[1-(thiophen-2-ylmethyl)piperidin-4-yl]-2,3-dihydro-1H-isoindole-4-carboxamide,
21. 2-[1-(cyclohexylmethyl)piperidin-4-yl]-1-methyl-3-oxo-2,3-dihydro-1H-isoindole-4-carboxamide,
22. 2-[1-(cyclohex-3-en-1-ylmethyl)piperidin-4-yl]-1-methyl-3-oxo-2,3-dihydro-1H-isoindole-4-carboxamide,
23. 2-{1-[(3-fluoropyridin-4-yl)methyl]piperidin-4-yl}-1-methyl-3-oxo-2,3-dihydro-1H-isoindole-4-carboxamide,
24. 1-methyl-2-{1-[(1-methyl-1H-pyrrol-2-yl)methyl]piperidin-4-yl}-3-oxo-2,3-dihydro-1H-isoindole-4-carboxamide,
25. 1-methyl-2-{1-[3-(methylsulfanyl)propyl]piperidin-4-yl}-3-oxo-2,3-dihydro-1H-isoindole-4-carboxamide,
26. 2-[1-(1H-imidazol-2-ylmethyl)piperidin-4-yl]-1-methyl-3-oxo-2,3-dihydro-1H-isoindole-4-carboxamide,
27. 2-{1-[(2-chloropyridin-3-yl)methyl]piperidin-4-yl}-1-methyl-3-oxo-2,3-dihydro-1H-isoindole-4-carboxamide,
28. 1-methyl-3-oxo-2-{1-[3-(1H-pyrazol-1-yl)benzyl]piperidin-4-yl}-2,3-dihydro-1H-isoindole-4-carboxamide,
29. 1-methyl-2-{1-[(5-methylfuran-2-yl)methyl]piperidin-4-yl}-3-oxo-2,3-dihydro-1H-isoindole-4-carboxamide,
30. 1-methyl-3-oxo-2-{1-[(3-phenyl-1H-pyrazol-5-yl)methyl]piperidin-4-yl}-2,3-dihydro-1H-isoindole-4-carboxamide,
31. 2-{1-[(5-bromothiophen-2-yl)methyl]piperidin-4-yl}-1-methyl-3-oxo-2,3-dihydro-1H-isoindole-4-carboxamide,
32. 2-[1-(3-hydroxybenzyl)piperidin-4-yl]-1-methyl-3-oxo-2,3-dihydro-1H-isoindole-4-carboxamide,
33. 2-{1-[2-(difluoromethoxy)benzyl]piperidin-4-yl}-1-methyl-3-oxo-2,3-dihydro-1H-isoindole-4-carboxamide,
34. 2-(1-{[5-(hydroxymethyl)furan-2-yl]methyl}piperidin-4-yl)-1-methyl-3-oxo-2,3-dihydro-1H-isoindole-4-carboxamide,
35. 1-methyl-2-[4-(morpholin-4-yl)phenyl]-3-oxo-2,3-dihydro-1H-isoindole-4-carboxamide,
36. 1-methyl-3-oxo-2-[4-(piperidin-1-yl)phenyl]-2,3-dihydro-1H-isoindole-4-carboxamide,
37. 1-methyl-2-[4-(4-methylpiperazin-1-yl)phenyl]-3-oxo-2,3-dihydro-1H-isoindole-4-carboxamide,
38. 1-methyl-3-oxo-2-[4-(piperidin-1-ylmethyl)phenyl]-2,3-dihydro-1H-isoindole-4-carboxamide,
39. tert-butyl 4-(4-carbamoyl-6-fluoro-1-methyl-3-oxo-1,3-dihydro-2H-isoindol-2-yl)piperidine-1-carboxylate,
40. 6-fluoro-1-methyl-3-oxo-2-(piperidin-4-yl)-2,3-dihydro-1H-isoindole-4-carboxamide,
41. 2-(1-cyclohexylpiperidin-4-yl)-6-fluoro-1-methyl-3-oxo-2,3-dihydro-1H-isoindole-4-carboxamide,
42. 2-[1-(4,4-difluorocyclohexyl)piperidin-4-yl]-6-fluoro-1-methyl-3-oxo-2,3-dihydro-1H-isoindole-4-carboxamide,
43. 6-fluoro-2-[1-(1H-indol-5-ylmethyl)piperidin-4-yl]-1-methyl-3-oxo-2,3-dihydro-1H-isoindole-4-carboxamide,
44. 6-fluoro-1-methyl-3-oxo-2-[1-(pyridin-2-ylmethyl)piperidin-4-yl]-2,3-dihydro-1H-isoindole-4-carboxamide,
45. 6-fluoro-1-methyl-2-{1-[(4-methyl-1,3-thiazol-5-yl)methyl]piperidin-4-yl}-3-oxo-2,3-dihydro-1H-isoindole-4-carboxamide,
46. 2-[1-(2,4-difluorobenzyl)piperidin-4-yl]-6-fluoro-1-methyl-3-oxo-2,3-dihydro-1H-isoindole-4-carboxamide,
47. 2-(1-cyclopentylpiperidin-4-yl)-6-fluoro-1-methyl-3-oxo-2,3-dihydro-1H-isoindole-4-carboxamide,
48. 6-fluoro-1-methyl-2-{1-[(6-methylpyridin-2-yl)methyl]piperidin-4-yl}-3-oxo-2,3-dihydro-1H-isoindole-4-carboxamide, 49. 6-fluoro-2-[1-(furan-2-ylmethyl)piperidin-4-yl]-1-methyl-3-oxo-2,3-dihydro-1H-isoindole-4-carboxamide,
50. 6-fluoro-1-methyl-3-oxo-2-{1-[3-(piperidin-1-yl)benzyl]piperidin-4-yl}-2,3-dihydro-1H-isoindole-4-carboxamide,
51. 6-fluoro-1-methyl-2-(1-{[6-(morpholin-4-yl)pyridin-2-yl]methyl}piperidin-4-yl)-3-oxo-2,3-dihydro-1H-isoindole-4-carboxamide,
52. 2-(1-cyclobutylpiperidin-4-yl)-6-fluoro-1-methyl-3-oxo-2,3-dihydro-1H-isoindole-4-carboxamide,
53. 6-fluoro-1-methyl-3-oxo-2-[1-(1H-pyrrol-2-ylmethyl)piperidin-4-yl]-2,3-dihydro-1H-isoindole-4-carboxamide,
54. 6-fluoro-1-methyl-3-oxo-2-[1-(thiophen-2-ylmethyl)piperidin-4-yl]-2,3-dihydro-1H-isoindole-4-carboxamide,
55. 2-[1-(cyclohexylmethyl)piperidin-4-yl]-6-fluoro-1-methyl-3-oxo-2,3-dihydro-1H-isoindole-4-carboxamide,
56. 2-[1-(cyclohex-3-en-1-ylmethyl)piperidin-4-yl]-6-fluoro-1-methyl-3-oxo-2,3-dihydro-1H-isoindole-4-carboxamide,
57. 6-fluoro-2-{1-[(3-fluoropyridin-4-yl)methyl]piperidin-4-yl}-1-methyl-3-oxo-2,3-dihydro-1H-isoindole-4-carboxamide,
58. 6-fluoro-1-methyl-2-{1-[(1-methyl-1H-pyrrol-2-yl)methyl]piperidin-4-yl}-3-oxo-2,3-dihydro-1H-isoindole-4-carboxamide,
59. 6-fluoro-2-[1-(1H-imidazol-2-ylmethyl)piperidin-4-yl]-1-methyl-3-oxo-2,3-dihydro-1H-isoindole-4-carboxamide,
60. 2-{1-[(2-chloropyridin-3-yl)methyl]piperidin-4-yl}-6-fluoro-1-methyl-3-oxo-2,3-dihydro-1H-isoindole-4-carboxamide,
61. 6-fluoro-1-methyl-2-{1-[(5-methylfuran-2-yl)methyl]piperidin-4-yl}-3-oxo-2,3-dihydro-1H-isoindole-4-carboxamide,
62. 2-{1-[(5-bromothiophen-2-yl)methyl]piperidin-4-yl}-6-fluoro-1-methyl-3-oxo-2,3-dihydro-1H-isoindole-4-carboxamide,
63. 6-fluoro-2-(1-{[5-(hydroxymethyl)furan-2-yl]methyl}piperidin-4-yl)-1-methyl-3-oxo-2,3-dihydro-1H-isoindole-4-carboxamide,
64. (1S)-2-(1-cyclohexylpiperidin-4-yl)-6-fluoro-1-methyl-3-oxo-2,3-dihydro-1H-isoindole-4-carboxamide,
65. (1R)-2-(1-cyclohexylpiperidin-4-yl)-6-fluoro-1-methyl-3-oxo-2,3-dihydro-1H-isoindole-4-carboxamide,
66. 1-methyl-3-oxo-2-[4-(piperidin-4-ylmethyl)phenyl]-2,3-dihydro-1H-isoindole-4-carboxamide,
67. 1-methyl-3-oxo-2-[4-(piperazin-1-ylmethyl)phenyl]-2,3-dihydro-1H-isoindole-4-carboxamide,
68. 1-methyl-2-{4-[(1-methylpiperidin-4-yl)methyl]phenyl}-3-oxo-2,3-dihydro-1H-isoindole-4-carboxamide,
69. 1-methyl-2-[3-(1-methylpiperidin-4-yl)phenyl]-3-oxo-2,3-dihydro-1H-isoindole-4-carboxamide,
70. 1-methyl-2-[3-(4-methylpiperazin-1-yl)phenyl]-3-oxo-2,3-dihydro-1H-isoindole-4-carboxamide,
71. 2-[4-cyclohexyl-3-(1-methylpiperidin-4-yl)phenyl]-1-methyl-3-oxo-2,3-dihydro-1H-isoindole-4-carboxamide,
72. 2-[4-cyclohexyl-3-(4-methylpiperazin-1-yl)phenyl]-1-methyl-3-oxo-2,3-dihydro-1H-isoindole-4-carboxamide,
73. 2-[1-(cyclohex-3-en-1-ylmethyl)piperidin-4-yl]-1-methyl-3-oxo-2,3-dihydro-1H-isoindole-4-carboxamide,
74. 1-methyl-3-oxo-2-[1-(2,2,2-trifluoroethyl)piperidin-4-yl]-2,3-dihydro-1H-isoindole-4-carboxamide hydrate,
75. 1-methyl-3-oxo-2-[1-(tetrahydrofuran-3-ylmethyl)piperidin-4-yl]-2,3-dihydro-1H-isoindole-4-carboxamide,
76. tert-butyl 3-{[4-(4-carbamoyl-1-methyl-3-oxo-1,3-dihydro-2H-isoindol-2-yl)piperidin-1-yl]methyl}azetidine-1-carboxylate,
77. 1-methyl-2-{1-[2-methyl-2-(piperidin-1-yl)propyl]piperidin-4-yl}-3-oxo-2,3-dihydro-1H-isoindole-4-carboxamide,
78. 2-{1-[3-(dimethylamino)-2,2-dimethylpropyl]piperidin-4-yl}-1-methyl-3-oxo-2,3-dihydro-1H-isoindole-4-carboxamide,
79. 2-{1-[(1-ethyl-4,5-dihydro-1H-pyrazol-4-yl)methyl]piperidin-4-yl}-1-methyl-3-oxo-2,3-dihydro-1H-isoindole-4-carboxamide,
80. 1-methyl-2-[1-(2-methylbutyl)piperidin-4-yl]-3-oxo-2,3-dihydro-1H-isoindole-4-carboxamide,
81. 2-[1-(cyclopentylmethyl)piperidin-4-yl]-1-methyl-3-oxo-2,3-dihydro-1H-isoindole-4-carboxamide,
82. methyl 4-[4-(4-carbamoyl-1-methyl-3-oxo-1,3-dihydro-2H-isoindol-2-yl)piperidin-1-yl]butanoate,
83. 1-methyl-3-oxo-2-[1-(2,2,2-trichloroethyl)piperidin-4-yl]-2,3-dihydro-1H-isoindole-4-carboxamide,
84. ethyl 2-{[4-(4-carbamoyl-1-methyl-3-oxo-1,3-dihydro-2H-isoindol-2-yl)piperidin-1-yl]methyl}cyclopropanecarboxylate,
85. 2-(1-hexylpiperidin-4-yl)-1-methyl-3-oxo-2,3-dihydro-1H-isoindole-4-carboxamide,
86. 1-methyl-2-(1-nonylpiperidin-4-yl)-3-oxo-2,3-dihydro-1H-isoindole-4-carboxamide,
87. 2-[1-(3-cyclohexylpropyl)piperidin-4-yl]-1-methyl-3-oxo-2,3-dihydro-1H-isoindole-4-carboxamide,
88. 1-methyl-3-oxo-2-[1-(3-phenylpropyl)piperidin-4-yl]-2,3-dihydro-1H-isoindole-4-carboxamide,
89. 2-[1-(cyclopropylmethyl)piperidin-4-yl]-1-methyl-3-oxo-2,3-dihydro-1H-isoindole-4-carboxamide,
90. 2-(1-heptylpiperidin-4-yl)-1-methyl-3-oxo-2,3-dihydro-1H-isoindole-4-carboxamide,
91. 1-methyl-3-oxo-2-(1-pentylpiperidin-4-yl)-2,3-dihydro-1H-isoindole-4-carboxamide,
92. 1-methyl-3-oxo-2-[1-(2-phenylethyl)piperidin-4-yl]-2,3-dihydro-1H-isoindole-4-carboxamide,
93. 2-[1-(3,3-dimethylbutyl)piperidin-4-yl]-1-methyl-3-oxo-2,3-dihydro-1H-isoindole-4-carboxamide,
94. 1-methyl-3-oxo-2-(1-propylpiperidin-4-yl)-2,3-dihydro-1H-isoindole-4-carboxamide,
95. 2-[1-(5-hydroxypentyl)piperidin-4-yl]-1-methyl-3-oxo-2,3-dihydro-1H-isoindole-4-carboxamide,
96. 1-methyl-3-oxo-2-[1-(2,2,2-trifluoroethyl)piperidin-4-yl]-2,3-dihydro-1H-isoindole-4-carboxamide,
97. 2-(1-butylpiperidin-4-yl)-1-methyl-3-oxo-2,3-dihydro-1H-isoindole-4-carboxamide,
98. 1-methyl-2-[1-(2-methylpropyl)piperidin-4-yl]-3-oxo-2,3-dihydro-1H-isoindole-4-carboxamide,
99. 1-methyl-2-{1-[(1-methyl-1H-benzimidazol-2-yl)methyl]piperidin-4-yl}-3-oxo-2,3-dihydro-1H-isoindole-4-carboxamide,
100. 2-[1-(2,3-dihydroxypropyl)piperidin-4-yl]-1-methyl-3-oxo-2,3-dihydro-1H-isoindole-4-carboxamide,
101. 2-[1-(2,2-dimethylpropyl)piperidin-4-yl]-1-methyl-3-oxo-2,3-dihydro-1H-isoindole-4-carboxamide,
102. 2-[1-(2,2-dimethylpent-4-en-1-yl)piperidin-4-yl]-1-methyl-3-oxo-2,3-dihydro-1H-isoindole-4-carboxamide,
103. 2-(1-ethylpiperidin-4-yl)-1-methyl-3-oxo-2,3-dihydro-1H-isoindole-4-carboxamide,
104. 1-methyl-2-[1-(3-methylbutyl)piperidin-4-yl]-3-oxo-2,3-dihydro-1H-isoindole-4-carboxamide,
105. 2-[1-(2-ethylbutyl)piperidin-4-yl]-1-methyl-3-oxo-2,3-dihydro-1H-isoindole-4-carboxamide, 106. 2-(1-cyclohexylpiperidin-4-yl)-1,1-dimethyl-3-oxo-2,3-dihydro-1H-isoindole-4-carboxamide,
107. 2-(1-cyclopentylpiperidin-4-yl)-1,1-dimethyl-3-oxo-2,3-dihydro-1H-isoindole-4-carboxamide,
108. 2-(1-cyclobutylpiperidin-4-yl)-1,1-dimethyl-3-oxo-2,3-dihydro-1H-isoindole-4-carboxamide,
109. 2-(1-cyclohexylpiperidin-4-yl)-6-fluoro-1,1-dimethyl-3-oxo-2,3-dihydro-1H-isoindole-4-carboxamide,
110. 2-(1-cyclopentylpiperidin-4-yl)-6-fluoro-1,1-dimethyl-3-oxo-2,3-dihydro-1H-isoindole-4-carboxamide,
111. 2-(1-cyclobutylpiperidin-4-yl)-6-fluoro-1,1-dimethyl-3-oxo-2,3-dihydro-1H-isoindole-4-carboxamide,
112. 2'-(1-cyclohexylpiperidin-4-yl)-3'-oxo-2',3'-dihydrospiro[cyclopropane-1,1'-isoindole]-4'-carboxamide,
113. 2'-(1-cyclohexylpiperidin-4-yl)-6'-fluoro-3'-oxo-2',3'-dihydrospiro[cyclopropane-1,1'-isoindole]-4'-carboxamide,
114. 2'-(1-cyclopentylpiperidin-4-yl)-3'-oxo-2',3'-dihydrospiro[cyclopropane-1,1'-isoindole]-4'-carboxamide,
115. 2'-(1-cyclopentylpiperidin-4-yl)-6'-fluoro-3'-oxo-2',3'-dihydrospiro[cyclopropane-1,1'-isoindole]-4'-carboxamide,
116. 2'-(1-cyclobutylpiperidin-4-yl)-3'-oxo-2',3'-dihydrospiro[cyclopropane-1,1'-isoindole]-4'-carboxamide,
117. 2'-(1-cyclobutylpiperidin-4-yl)-6'-fluoro-3'-oxo-2',3'-dihydrospiro[cyclopropane-1,1'-isoindole]-4'-carboxamide,
118. 2-(1-cyclohexylpiperidin-4-yl)-1-methylidene-3-oxo-2,3-dihydro-1H-isoindole-4-carboxamide,
119. 2-(1-cyclohexylpiperidin-4-yl)-6-fluoro-1-methylidene-3-oxo-2,3-dihydro-1H-isoindole-4-carboxamide,
120. 2-(1-cyclopentylpiperidin-4-yl)-1-methylidene-3-oxo-2,3-dihydro-1H-isoindole-4-carboxamide,
121. 2-(1-cyclopentylpiperidin-4-yl)-6-fluoro-1-methylidene-3-oxo-2,3-dihydro-1H-isoindole-4-carboxamide,
122. 2-(1-cyclohexylazetidin-3-yl)-1-methyl-3-oxo-2,3-dihydro-1H-isoindole-4-carboxamide,
123. 2-(1-cyclohexylazetidin-3-yl)-6-fluoro-1-methyl-3-oxo-2,3-dihydro-1H-isoindole-4-carboxamide,
124. 2-(1-cyclopentylazetidin-3-yl)-1-methyl-3-oxo-2,3-dihydro-1H-isoindole-4-carboxamide,
125. 2-(1-cyclopentylazetidin-3-yl)-6-fluoro-1-methyl-3-oxo-2,3-dihydro-1H-isoindole-4-carboxamide,
126. 2-[1-(4,4-difluorocyclohexyl)piperidin-4-yl]-6-fluoro-1-methyl-3-oxo-2,3-dihydro-1H-isoindole-4-carboxamide,
127. 2-(1-cyclohexylpiperidin-4-yl)-6-fluoro-1-methyl-3-oxo-2,3-dihydro-1H-isoindole-4-carboxamide and
128. 2-(1-cyclohexylpiperidin-4-yl)-6-fluoro-1,1-dimethyl-3-oxo-2,3-dihydro-1H-isoindole-4-carboxamide or a pharmaceutically acceptable salt thereof.

The present invention also provides processes for the preparation of compounds of formula (I) as defined above. Accordingly, a process of the present invention comprises one of the following sequence of steps:

Sequence A)

Step a) Halogenating a Compound of Formula (X):

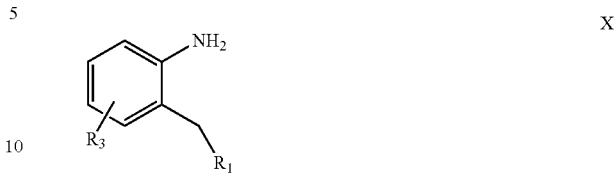

wherein $R_1$ and $R_3$ are as defined above;

Step b) Cyano-De-Aminating the Resultant Compound of Formula (IX):

wherein Hal is halogen such as Cl, Br, I and $R_1$ and $R_3$ are as defined above;

Step c) Hydrolyzing the Resultant Compound of Formula (VIII):

wherein Hal, $R_1$ and $R_3$ are as defined above;

Step d) Hydrolyzing the Resultant Compound of Formula (VII):

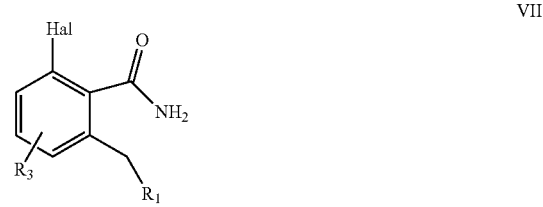

wherein Hal, $R_1$ and $R_3$ are as defined above;

Step e) Esterifying the Resultant Compound of Formula (VI):

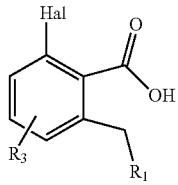
VI wherein Hal, $R_1$ and $R_3$ are as defined above;

Step f) Cyclizing the Resultant Compound of Formula (V):

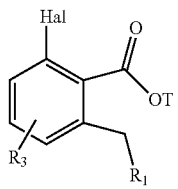
V wherein T is $C_1$-$C_6$ alkyl or aryl $C_1$-$C_6$ alkyl group and $R_1$ and $R_3$ are as defined above with a suitable amine of formula (XIV):

 XIV wherein R is as defined above;

Step g) Alkylating the Resultant Compound of Formula (IV):

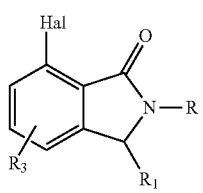
IV wherein Hal, R, $R_1$ and $R_3$ are as defined above;

Step h) Cyano-De-Halogenating the Resultant Compound of Formula (III):

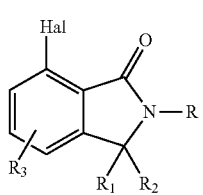
III wherein Hal, R, $R_1$, $R_2$ and $R_3$ are as defined above;

Step i) Hydrolyzing a Compound of Formula (II):

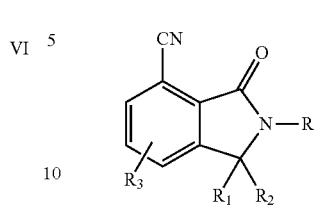
II wherein R, $R_1$, $R_2$ and $R_3$ are as defined above to give a compound of formula (I):

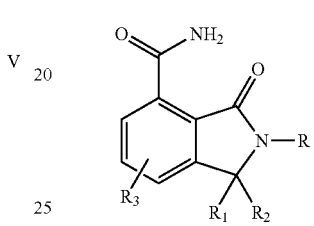
I wherein R, $R_1$, $R_2$ and $R_3$ are as defined above; or

Sequence B):

Step l) Halogenating a Compound of Formula (XI):

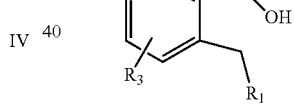
XI wherein $R_1$ and $R_3$ are as defined above;

Step e and m) Esterifying the Resultant Compound of Formula (VI) as Defined Above and Cyano-De-Halogenating the Resultant Compound of Formula (V) as Defined Above;

Step f') Cyclizing the Resultant Compound of Formula (XII)

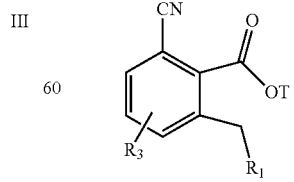
XII wherein T, $R_1$ and $R_3$ are as defined above, with a suitable amine of formula (XIV) as defined above;

Step g') Alkylating the Resultant Compound of Formula (XIII):

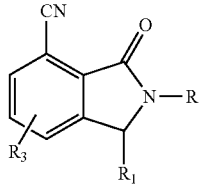

XIII wherein R, $R_1$ and $R_3$ are as defined above;

Step i') Hydrolyzing the Resultant Compound of Formula (XIII) as Defined Above to Give a Compound of Formula (I) as Defined Above, or Sequence C)

either Step n) a reductive amination of a compound of formula (XV):

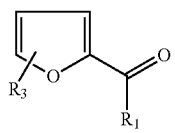

XV wherein $R_1$ and $R_3$ are as defined above with a suitable amine of formula (XIV) as defined above;

or Step q) a reductive alkylation of a compound of formula (XX):

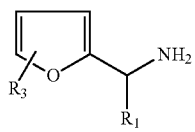

XX wherein $R_1$ and $R_3$ are as defined above;

Step o) Reacting with Maleic Anhydride Under Diels-Alder Conditions the Resultant Compound of Formula (XVI):

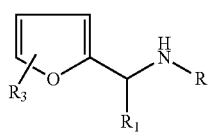

XVI wherein R, $R_1$ and $R_3$ are as defined above;

Step p) Aromatizing the Resultant Compound of Formula (XVII):

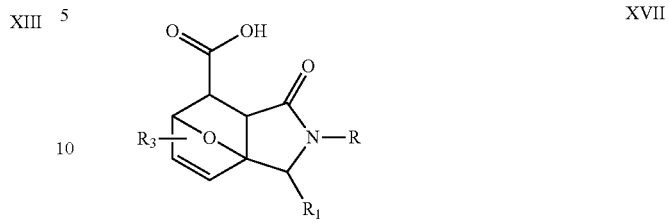

XVII wherein R, $R_1$ and $R_3$ are as defined above and either Step i") amidating the resultant compound of formula (XVIII):

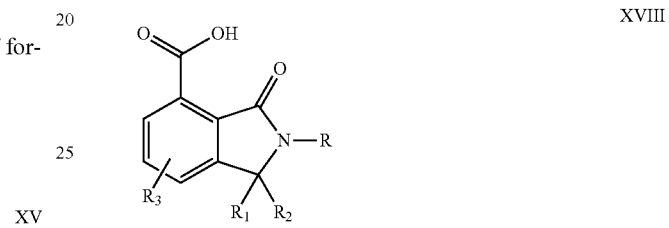

XVIII wherein R, $R_1$ and $R_3$ are as defined above and $R_2$ is hydrogen atom so as to obtain a compound of formula (I) as defined above wherein $R_2$ is hydrogen atom, or Step e') Esterifying a Compound of Formula (XVIII) as Defined Above Wherein R is as Defined Above;

Step s) N-Deprotecting the Resultant Compound of Formula (XXI):

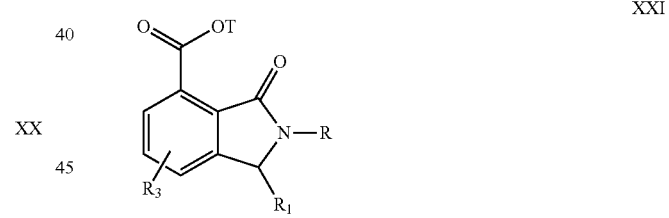

XXI wherein T, $R_1$ and $R_3$ are as defined above and R is as defined above;

Step t) N-Alkylating the Resultant Compound of Formula (XXII):

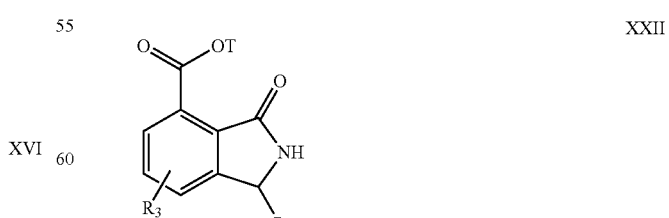

XXII wherein T, $R_1$ and $R_3$ are as defined above and;

either Step r) hydrolyzing the resultant compound of formula (XXI) as defined above wherein R is as defined above;

or Step g") alkylating a compound of formula (XXI) as defined above wherein R is as defined above;

Step r') hydrolyzing the resultant compound of formula (XXIII):

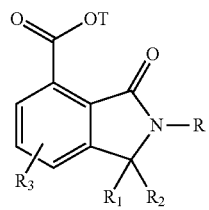

XXIII wherein T, $R_1$, and $R_3$ are as defined above and $R_2$ is not hydrogen atom and then converting the resultant compound of formula (XVIII) wherein R, $R_1$ and $R_3$ are as defined above and $R_2$ is not hydrogen atom operating as described above under step i").

If necessary or wanted, the processes above described comprises converting a compound of formula (I) into a different compound of formula (I) by known chemical reactions; and/or, if desired, converting a compound of formula (I) into a pharmaceutically acceptable salt thereof or converting a salt into a free compound of formula (I).

Also an intermediate compound of formula (II), (III) and (XVIII) as defined above may be converted into a different compound of formula (II), (III) and (XVIII).

The known chemical reactions for possible conversions of compounds of the formula (I), (II), (III) and (XVIII) as defined above into a different compound of the formula (I), (II), (III) and (XVIII) as defined above are for example:

1Cv) an alkylation of a compound of formula (II) or (III) as defined above;

2Cv) a protection of a compound of formula (XVIII) as defined above;

3Cv) a deprotection of a compound of formula (I) or (II) as defined above;

4Cv) a reductive amination of a compound of formula (I) or (II) as defined above.

All the above processes are analogy processes which can be carried out according to well known methods and under suitable conditions known in the art.

The synthesis of a compound of formula (I), according to the synthetic processes described above, can be carried out in a stepwise manner, whereby each intermediate is isolated and purified by standard purification techniques, like, for example, column chromatography, before carrying out the subsequent reaction. Alternatively, two or more steps of the synthetic sequence can be carried out in a so-called "one-pot" procedure, as known in the art, whereby only the compound resulting from the two or more steps is isolated and purified.

Schemes 1-2 below show the preparation of a compound of formula (I) as defined above.

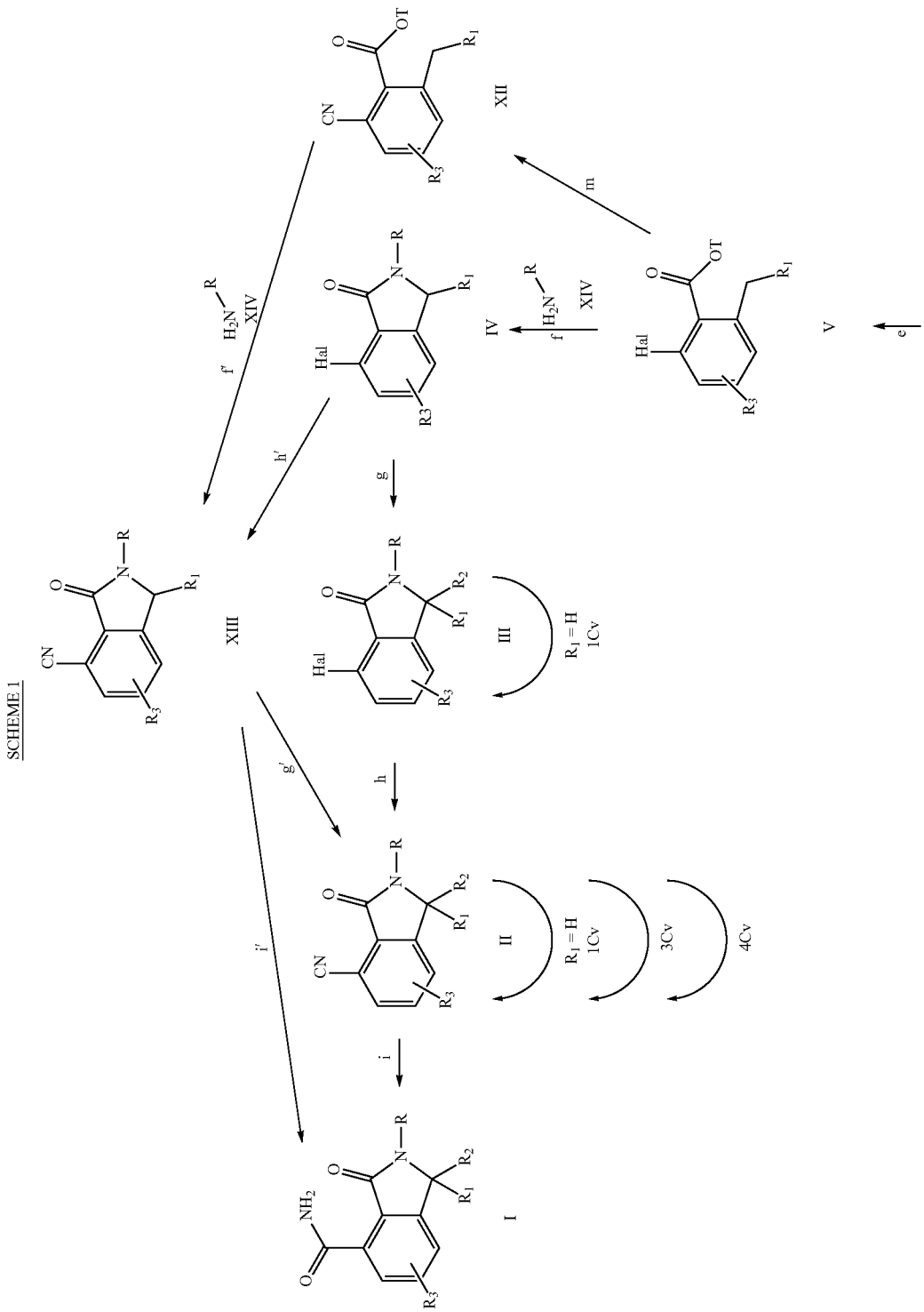

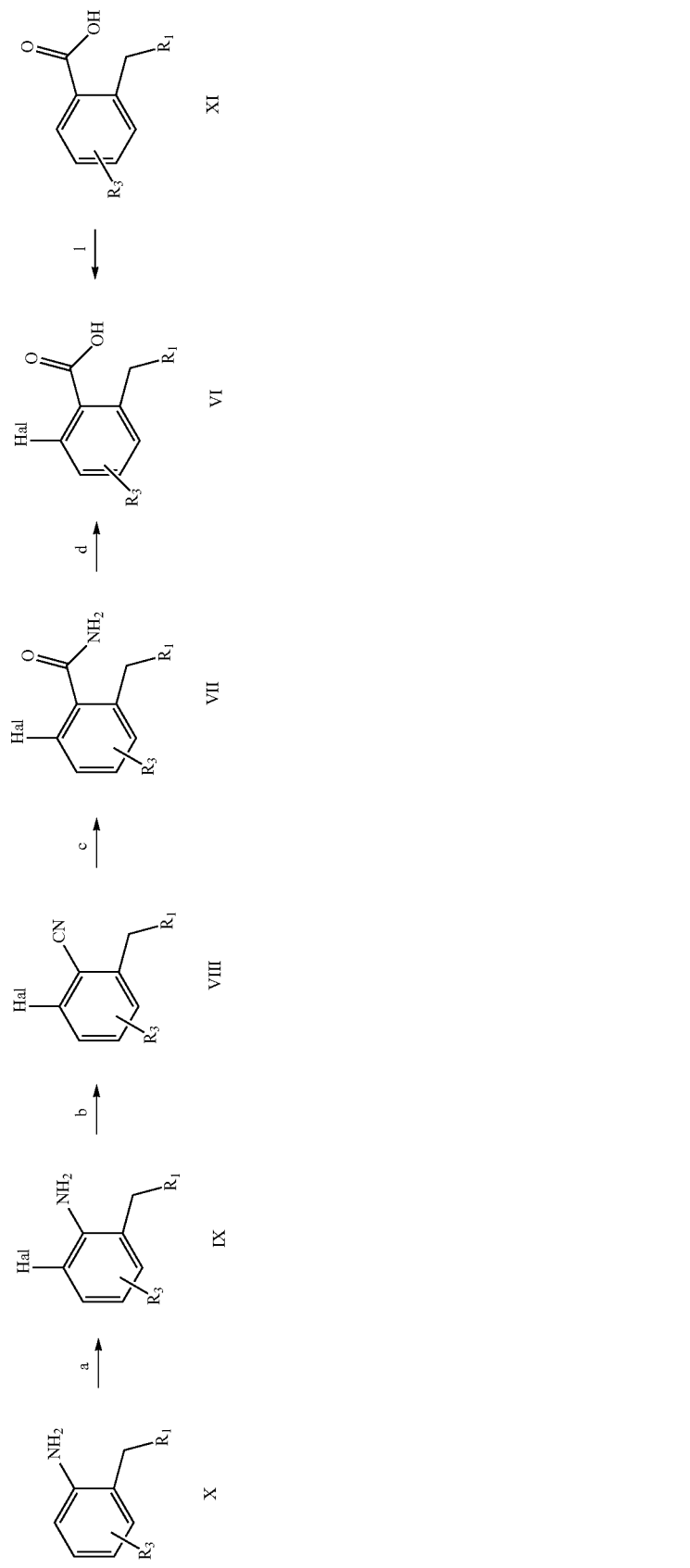

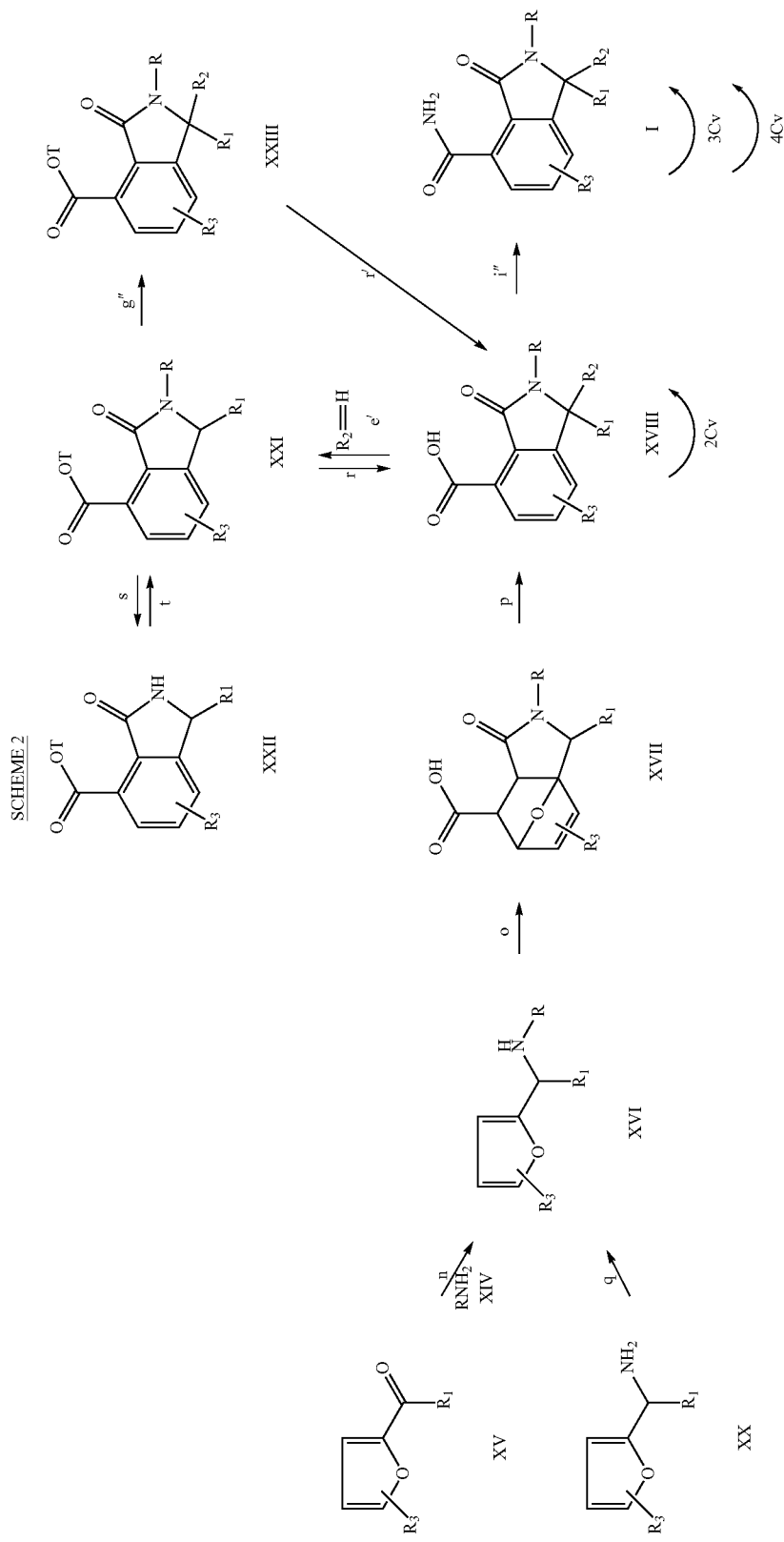

According to step a), a compound of formula (IX) can be obtained by halogenating a compound of formula (X) in different ways and experimental conditions known in the art. Preferably this reaction is carried out in the presence of N-bromosuccinimide, N-iodosuccinimmide, N-chlorosuccinimide, bromine, iodine, hydrobromic acid/hydrogen peroxide, in a suitable solvent, such as acetonitrile, N,N-dimethylformamide, dioxane, dimethylsulfoxide, acetic acid, water at a temperature ranging from about room temperature to reflux and for a period of time ranging from about 1 hour to about 96 hours.

According to step b), a compound of formula (VIII) can be obtained by a two-reactions sequence from a compound of formula (IX) in different ways and experimental conditions known in the art. First reaction is preferably carried out in the presence of sodium nitrite/hydrochloric acid or tert-butylnitrite in a suitable solvent, such as tetrahydrofurane, dimethoxyethane, dimethylsulfoxide, acetic acid, water at a temperature ranging from about −20° C. to room temperature and for a period of time ranging from 10 minutes to about 24 hours. Second step is preferably carried out in the presence of sodium, copper or potassium cyanide, often in the presence of an additive such as copper or potassium chloride, in a suitable solvent such as tetrahydrofuran, dimethoxyethane, dimethylsulfoxide, acetic acid, toluene, water at a temperature ranging from about −20° C. to reflux and for a period of time ranging from 10 minutes to about 96 hours. According to step c), the hydrolysis of a compound of formula (VIII) to give a compound of formula (VII) can be carried out in different ways, according to conventional methods for transforming a cyano group to amide. Preferably this reaction is carried out in a suitable solvent such as, for instance, methanol, ethanol, butanol, 1,4-dioxane, water, or a mixture thereof, in the presence of a suitable acid or base, such as, for instance, sulfuric acid, hydrochloric acid, sodium hydroxide, sodium carbonate, or a suitable reagent such as hydrogen peroxide or sodium perborate. Typically, the reaction is carried out at a temperature ranging from room temperature to reflux and for a time ranging from about 1 hour to about 96 hours.

According to step d) a compound of formula (VII) can be converted into a compound of formula (VI) according to conventional methods. Preferably the reaction is carried out in the presence of water by treatment with a base such as potassium or sodium carbonate, potassium or sodium hydroxide, in a suitable solvent such as, for instance, methanol, ethanol, at a temperature ranging from room temperature to reflux, for a time ranging from about 30 min. to about 96 hours. Alternatively this reaction can be carried out in the presence of sodium nitrite/acetic acid, sulfuric acid, fosforic acid at a temperature ranging from room temperature to reflux and for a time ranging from about 1 hour to about 96 hours.

According to step e) a compound of formula (VI) can be converted into a compound of formula (V) according to conventional methods. Preferably the reaction is carried out in the presence of hydrochloric acid, sulfuric acid, acetic acid in a solvent like methanol, ethanol, water, or a mixture thereof, at a temperature ranging from room temperature to reflux and for a time ranging from about 1 hour to about 96 hours. Alternatively, this reaction can be carried out with alkyl iodide or bromide in the presence of a suitable base such as sodium or potassium carbonate, sodium, lithium or potassium hydroxide at a temperature ranging from room temperature to reflux and for a period of time ranging from about 1 hour to about 96 hours.

According to step f), a compound of formula (IV) can be obtained by a two-reactions sequence from a compound of formula (V) in the presence of a compound of formula (XIV) in different ways and experimental conditions known in the art. First reaction is preferably carried out in the presence of N-bromosuccinimide with a radical initiator such as benzoyl peroxide or azobisisobutyronitrile in a suitable solvent, such as carbon tetrachloride, chloroform, dichloromethane or methyl pivalate at a temperature ranging from about room temperature to reflux and for a period of time ranging from 10 minutes to about 24 hours. Second reaction can be carried out both under basic or acidic conditions such as in the presence of sodium or potassium carbonate, 1,8-diazabicyclo[5.4.0]undec-7-ene, triethylamine, N,N—N,N-diisopropylethylamine, pyridine or acetic acid, hydrochloric acid in a suitable solvent, such as tetrahydrofurane, dimethoxyethane, 1,4-dioxane, toluene at a temperature ranging from room temperature to reflux and for a period of time ranging from 1 hour to about 96 hours.

According to step g) the conversion of a compound of formula (IV) into a compound of formula (III) can be carried out in different ways, according to conventional methods for C-alkylation reactions. Preferably, this reaction is carried out in a suitable solvent such as, for instance, tetrahydrofuran, diethyl ether, dioxane, N,N-dimethylformamide, dimethoxyethane, in the presence of a suitable base, such as, for instance, lithium, sodium or potassium bis(trimethylsilyl)amide, sodium, potassium or cesium carbonate, sodium hydride, at a temperature ranging from −78° C. to room temperature and for a time ranging from about 10 minutes to about 24 hours. Alkylating agent is usually a halogen or a sulphonates derivative; most often the leaving group is iodo, bromo, triflate or mesylate.

According to step h), the conversion of a compound of formula (III) into a compound of formula (II) can be carried out in different ways, according to conventional methods for cyanation reactions. Preferably, this reaction is carried out in the presence of copper cyanide or potassium hexacyanoferrate (II) as cyano source in a suitable solvent such as, for instance, methanol, ethanol, tetrahydrofuran, 1,4-dioxane, toluene, xylene, N-methyl-2-pyrrolidone, or a mixture thereof, at a temperature ranging from room temperature to reflux and for a time ranging from about 1 hour to about 96 hours. If a catalyst is required, it is usually a metal, most often a palladium derivative such as, for instance, palladium(II) chloride or palladium(II) acetate in the presence of a suitable base such as, for instance, sodium, potassium or cesium carbonate, cesium fluoride.

According to step i) the conversion of a compound of formula (II) into a compound of formula (I) can be carried out in different ways and experimental conditions. Preferably it is carried out in a way analogous to that reported for step c).

According to step l), the halogenation of a compound of formula (XI) into a compound of formula (VI) can be carried out in different ways, according to conventional methods for halogenation reactions. Preferably, this reaction is carried out with tetrabutylammonium bromide and/or iodine in the presence of phenyliodine(III) bis(trifluoracetate) or phenyliodo(III) diacetate as halogen source in a suitable solvent such as, for instance, N,N-dimethylformamide or dichloroethane, at a temperature ranging from room temperature to reflux and for a time ranging from about 1 hour to about 48 hours. The catalyst is usually a metal, most often a palladium derivative such as, for instance, palladium(II) chloride or palladium(II) acetate.

According to step m) the cyanation of a compound of formula (V) to give a compound of formula (XII) can be carried out in different ways and experimental conditions.

Preferably it is carried out in a way analogous to that reported for step h).

According to step f') the transformation of a compound of formula (XII) into a compound of formula (XIII) in the presence of a compound of formula (XIV) can be carried out in different ways and experimental conditions. Preferably it is carried out in a way analogous to that reported for step f).

According to step h') the cyanation of a compound of formula (IV) to give a compound of formula (XIII) can be carried out in different ways and experimental conditions. Preferably it is carried out in a way analogous to that reported for step h).

According to step g') the transformation of a compound of formula (XIII) into a compound of formula (II) can be carried out in different ways and experimental conditions. Preferably it is carried out in a way analogous to that reported for step g).

According to step i) the conversion of a compound of formula (XIII) into a compound of formula (I) can be carried out in different ways and experimental conditions. Preferably it is carried out in a way analogous to that reported for step c).

According to step n) the reductive amination of a compound of formula (XV) to give a compound of formula (XVI), by reaction with a suitable amine of formula (XIV), can be carried out in different ways, according to conventional methods for carrying out reductive amination. Preferably, this reaction is carried out in a suitable solvent such as, for instance, methanol, N,N-dimethylformamide, dichloromethane, tetrahydrofuran, benzene, toluene, or a mixture thereof, in the presence of a suitable reducing agent such as, for instance, sodium borohydride, tetraalkylammonium borohydride, sodium cyanoborohydride, sodium triacetoxyborohydride, tetramethylammonium triacetoxy borohydride and in presence of an acid or basic catalyst, such as, for instance, acetic acid, trifluoroacetic acid, zinc chloride, zinc bromide, tin(IV) chloride, titanium(IV) chloride, boron trifluoride or triethylamine, N,N—N,N-diisopropylethylamine, pyridine at a temperature ranging from about 0° C. to reflux and for a time ranging from about 1 hour to about 96 hours.

According to step o) the Diels-Alder reaction of a compound of formula (XVI) to give a compound of formula (XVII) can be carried out in different ways, according to conventional methods for carrying out these reactions. Preferably, this reaction is carried out in a suitable solvent such as, for instance, tetrahydrofuran, benzene, toluene, o-xilene in the presence of maleic anhydride at a temperature ranging from about room temperature to reflux and for a time ranging from about 1 hour to about 96 hours.

According to step p) the conversion of a compound of formula (XVII) into a compound of formula (XVIII) can be carried out in different ways, according to conventional methods. Preferably, this reaction is carried out in a suitable solvent such as, for instance, tetrahydrofuran, toluene, water, in the presence of hydrochloric acid, p-tolensulfonic acid, phosphoric acid, at a temperature ranging from about room temperature to reflux and for a time ranging from about 1 hour to about 24 hours.

According to step i") a compound of formula (I) can be obtained by reacting a compound of formula (XVIII) in different ways and experimental conditions, which are widely known in the art of condensation reactions. Preferably a compound of formula (XVIII) is reacted with ammonia or ammonia source such as ammonium salts, in the presence of an activating agent such as carbonyldiimidazole, benzotriazol-1-yloxy)tris(dimethylamino)phosphonium hexafluorophosphate, 2-(1H-benzotriazol-1-yl)-1,1,3,3-tetramethyluronium tetrafluoroborate), (O-(7-azabenzotriazol-1-yl)-N,N,N',N'-tetramethyluronium hexafluorophosphate, dicyclohexyl carbodiimide, diisopropyl carbodiimide, 1-ethyl-3-(3'-dimethylamino) carbodiimide hydrochloric acid salt, optionally in the presence of hydroxybenzotriazole. Preferably, this reaction is carried out in a suitable solvent such as, for instance, N,N-dimethylformamide, N,N-dimethylacetamide, tetrahydrofuran, dichloromethane, 1,4-dioxane, and in the presence of a proton scavenger such as, for example, pyridine, triethylamine, N,N-diisopropylethylamine, at a temperature ranging from room temperature to reflux, for a time ranging from about 30 min. to about 96 hours.

According to step q) the conversion of a compound of formula (XX) into a compound of formula (XVI) can be carried out in different ways and experimental conditions. Preferably it is carried out in a way analogous to that reported for step n).

According to step e') the conversion of a compound of formula (XVIII) into a compound of formula (XXI) can be carried out in different ways and experimental conditions. Preferably it is carried out in a way analogous to that reported for step e).

According to step r) a compound of formula (XXI) can be transformed into a compound of formula (XVIII) according to conventional methods. Preferably the reaction is carried out in the presence of water by treatment with a base such as potassium or sodium carbonate, potassium or sodium hydroxide, in a suitable solvent such as, for instance, methanol, ethanol, at a temperature ranging from room temperature to reflux, for a time ranging from about 30 min. to about 96 hours. Alternatively this reaction can be carried out in the presence of hydrochloric acid, sulfuric acid, phosphoric acid at a temperature ranging from room temperature to reflux and for a time ranging from about 1 hour to about 96 hours.

According to step s), a compound of formula (XXI) can be transformed into a compound of formula (XXII) by deprotection of the nitrogen atom according to conventional methods enabling the selective hydrolysis of tert-butoxycarbonyl, benzyl, 4-methoxybenzyl, 2,4-dimethoxybenzyl and triphenylmethyl, phenylethyl protective groups. Preferably this reaction is run under acidic conditions, for instance in the presence of an inorganic or organic acid such as hydrochloric, trifluoroacetic or methanesulfonic acid, in a suitable solvent such as dichloromethane, 1,4-dioxane, a lower alcohol, such as methanol or ethanol, at a temperature ranging from room temperature to reflux and for a period of time ranging from about 1 hour to about 48 hours. In alternative, this reaction is carried out under reducing condition, such as, for instance, in the presence of molecular hydrogen and a hydrogenation catalyst in a suitable solvent such as ethanol, methanol, ethyl acetate, or a mixture thereof. The catalyst is usually a metal, most often a palladium derivative such as, for instance, palladium on carbon, palladium hydroxide or palladium black. Alternatively, the removal of protective group base-labile can be carried out by using a base such as potassium, sodium or cesium carbonate, potassium or sodium hydroxide, pyridine, triethylamine, N,N-diisopropylethylamine, in a suitable solvent such as methanol, ethanol, at a temperature ranging from room temperature to reflux and for a period of time ranging from about 1 hour to about 48 hours.

According to step t), the conversion of a compound of formula (XXII) into a compound of formula (XXI) can be carried out in different ways, according to conventional methods for N-alkylation reactions. Preferably, this reaction is carried out in a suitable solvent such as, for instance, tetrahydrofuran, dioxane, N,N-dimethylformamide, dimethoxyethane, dimethylsulfoxide, benzene in the presence of a suitable base, such as, for instance, triethylamine, N,N-diisopropylethylamine, sodium, potassium or cesium carbonate, sodium hydride, sodium methoxide, lithium, sodium or potassium bis(trimethylsilyl)amide at a temperature ranging from −78° C. to reflux and for a time ranging from about 1 hour to about 96 hours. Alkylating agent is usually a halogen or a sulphonates derivative; most often the leaving group is iodo, bromo, triflate or mesylate.

According to step g") the conversion of a compound of formula (XXI) into a compound of formula (XXIII) can be carried out in different ways and experimental conditions. Preferably it is carried out in a way analogous to that reported for step g).

According to step r') the conversion of a compound of formula (XXIII) into a compound of formula (XVIII) can be carried out in different ways and experimental conditions. Preferably it is carried out in a way analogous to that reported for step r).

According to the conversion described under 1Cv) the alkylation of a compound of formula (II) or (III) can be carried out in different ways and experimental conditions. Preferably it is carried out in a way analogous to that reported for step g).

According to the conversion described under 2Cv), the reaction of a compound of formula (XVIII) may be carried out in different ways and experimental conditions. Preferably when the protective group is tert-butoxycarbonyl, the reaction may be carried out in the presence of di-tert-butyl dicarbonate in different solvents such as methanol, ethanol, acetonitrile, tetrahydrofurane, dichloromethane in the presence of a base such as pyridine, N,N-dimethylaminopyridine, triethylamine, sodium or potassium carbonate at a temperature ranging from room temperature to reflux and for a time ranging from about 1 hour to about 96 hours.

According to the conversion described under 3Cv), the deprotection of a compound of formula (I) or (II) may be carried out in different ways and experimental conditions. Preferably when the protective group is tert-butoxycarbonyl, the reaction may be carried out in the presence of hydrochloric acid, trifluoroacetic acid in a suitable solent such as dioxane, dichloromethane, tetrahydrofurane at a temperature ranging from room temperature to reflux and for a time ranging from about 1 hour to about 24 hours.

According to the conversion described under 4Cv), the reductive ammination of a compound of formula (I) or (II) may be carried out in different ways and experimental conditions. Preferably it is carried out in a way analogous to that reported for step n).

Substituted isoindoles can be prepared using standard procedures in organic synthesis as reported, for instance, in Smith, Michael—March's Advanced Organic Chemistry: reactions mechanisms and structure—6th Edition, Michael B. Smith and Jerry March, John Wiley & Sons Inc., New York (NY), 2007. It is known to the skilled person that conversion of a chemical function into another may require that one or more reactive centers in the compound containing this function be protected in order to avoid undesired side reactions. Protection of such reactive centers, and subsequent deprotection at the end of the synthetic conversions, can be accomplished following standard procedures described, for instance, in: Green, Theodora W. and Wuts, Peter G. M. —Protective Groups in Organic Synthesis, Third Edition, John Wiley & Sons Inc., New York (NY), 1999.

In cases where a compound of formula (I) contains one or more asymmetric centers, said compound can be separated into the single isomers by procedures known to those skilled in the art. Such procedures comprise standard chromatographic techniques, including chromatography using a chiral stationary phase, or crystallization. General methods for separation of compounds containing one or more asymmetric centers are reported, for instance, in Jacques, Jean; Collet, André; Wilen, Samuel H.,—Enantiomers, Racemates, and Resolutions, John Wiley & Sons Inc., New York (NY), 1981.

As stated above, a compound of formula (I) can be converted into a pharmaceutically acceptable salt according to standard procedures that are known to those skilled in the art. Alternatively, a compound of formula (I) that is obtained as a salt can be converted into the corresponding free base or the free acid according to standard procedures that are known to the skilled person.

The starting materials of the process of the present invention, i.e. compounds of formula (X), (XI), (XIV), (XV) and (XX) are either commercially available or can be prepared by using well-known methods.

For example, the compound of formula (XX) can be easily obtained according to conventional procedures, which are widely known in the art for reductive amination reactions (see for example Demir, Ayhan et al. Helvetica Chimica Acta (2003), 86(1), 91-105).

The intermediate compounds of formula (II), (III), (IV), (XIII), (XVIII), (XXI), (XXII) and (XXIII) are novel and are also within the scope of the present invention.

Biochemical Assay

Affinity evaluation of the tested compounds and their selectivity with respect to the different PARP isoforms of interest was assessed in a displacement assay.

The identification of compounds capable of binding several PARP proteins is carried out through a screening method including the steps of a) providing a reaction mixture containing:
the PARP protein isoform under investigation,
a compound of formula (IP):

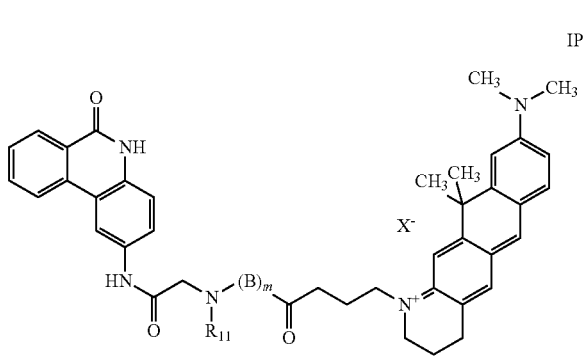

wherein $R_{11}$ is hydrogen atom or a methyl group, B is $(CH_2)_n$—NH group wherein n is 2 to 6; m is 0 or 1 and $X^{---}$ is a counterion, and
serial dilutions of the test compound;

b) comparing the polarization signal generated in the absence of the test compound with the one generated in the presence of different concentrations of the test compound, and c) evaluating the ability of the test compound to displace the compound of formula (IP) as defined above indicated from a decreased fluorescence polarization level.

Preferably, for the screening method above cited, either the PARP protein and the 5H-Phenanthridin-6-one-derived probe of formula (IP) are pre-mixed, or the PARP protein and the test compound are pre-mixed. In a further preferred screening method, the PARP proteins are PARP-1, PARP-2 and PARP-3. The term "PARP protein" encompasses full-length native proteins as well as fragment thereof.

More preferably, $R_{11}$ is hydrogen or methyl, m is 0 or 1; when m is 1, n is 3 or 6, $X^{---}$ is trifluoroacetate.

The 5H-phenanthridin-6-one-derived probe (IP) was selected for its capability of binding to the PARP proteins, both encompassing full-length native proteins and fragment thereof.

The polarization signal can be measured, e.g., by a plate reader such as the Saphire2 (Tecan). The displacement ability of the test compound is in correlation with the compound affinity for the NAD pocket of the enzyme. Affinity binding constant (KD) and $DC_{50}$s of the test compound can be determined as explained in the Example section. The assay used for testing the compounds of the invention is based on the use of known PARP inhibitors chemically conjugated to a moiety that provides the fluorescent signal. Specific compounds used are:

P1. 9-Dimethylamino-11,11-dimethyl-1-(3-{methyl-[(6-oxo-5,6-dihydro-phenanthridin-2-ylcarbamoyl)-methyl]-carbamoyl}-propyl)-2,3,4,11-tetrahydro-naphtho[2,3-g] quinolinium trifluoroacetate;

P2. 9-Dimethylamino-11,11-dimethyl-1-[3-(3-{[(6-oxo-5,6-dihydro-phenanthridin-2-ylcarbamoyl)-methyl]-amino}-propylcarbamoyl)-propyl]-2,3,4,11-tetrahydro-naphtho [2,3-g]quinolinium trifluoroacetate;

P3. 9-Dimethylamino-11,11-dimethyl-1-[3-(6-{[(6-oxo-5,6-dihydro-phenanthridin-2-ylcarbamoyl)-methyl]-amino}-hexylcarbamoyl)-propyl]-2,3,4,11-tetrahydro-naphtho[2, 3-g]quinolinium trifluoroacetate.

A compound of formula (IP) as defined above can be prepared through a process comprising:

step u) either reacting a compound of formula (XXIV):

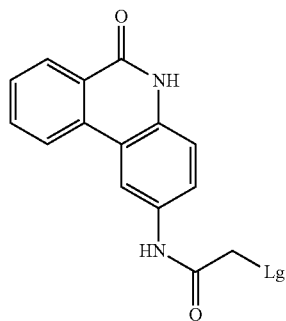

XXIV wherein Lg is a leaving group, preferably a chlorine atom, with a compound of formula (XXV): $R_{11}$—$NH_2$ wherein $R_{11}$ is as defined above, to give a compound of formula (XXVI):

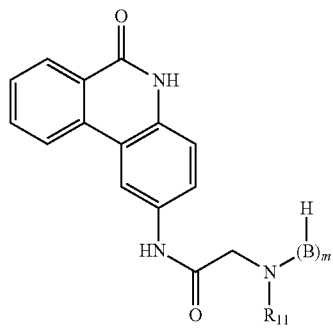

XXVI wherein $R_{11}$ is as defined above and m is 0;

or step v) reacting a compound of formula (XXIV) as defined above with a compound of formula XXVa:

XXVa wherein $R_{11}$ and B are as defined above, m is 1 and $R_{12}$ is hydrogen atom, methoxycarbonyl, ethoxycarbonyl, tert-butoxycarbonyl, benzyloxycarbonyl, 9-fluorenylmethoxycarbonyl or the like; and step z) converting if necessary the resultant compound of formula (XXVIa):

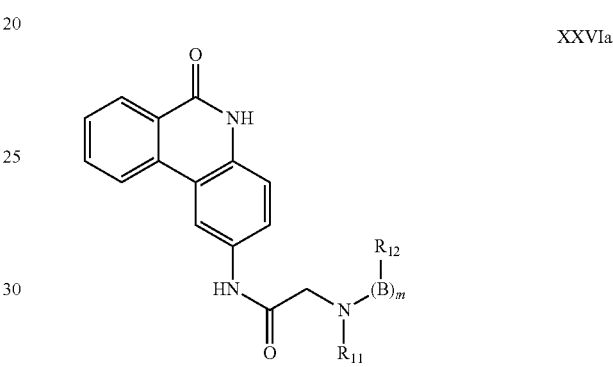

XXVIa wherein $R_{11}$ and B are as defined above, m is 1 and $R_{12}$ is a methoxycarbonyl, ethoxycarbonyl, tert-butoxycarbonyl, benzyloxycarbonyl, 9-fluorenylmethoxycarbonyl group or the like, into a compound of formula (XXVI) as defined above;

step ii) coupling the resultant compound of formula (XXVI) as defined above with a compound of formula (XXVII):

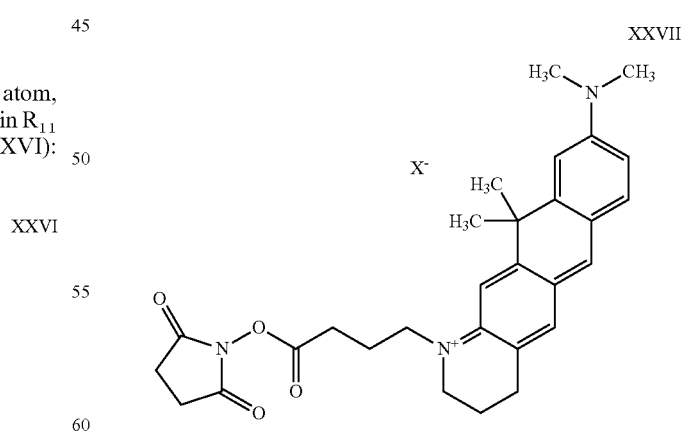

XXVII wherein $X^-$ is as defined above so as to obtain the final compound of formula (IP) as defined above; and, if necessary or wanted, converting a compound of formula (IP) into another compound of formula (IP) wherein $X^-$ is different.

The starting compound of formula (XXIV) can be prepared as extensively described, see, for instance WO 2001042219;

the compounds of formula (XXVII) are described in Cha, J. H. et al., *J. Med. Chem.* 2005, 48, 7513-7516 and ATTO 610 fluorescent moiety activated as its NHS ester is commercially available (Naphtho[2,3-g]quinolinium, 9-(dimethylamino)-1-[4-[(2,5-dioxo-1-pyrrolidinyl)oxy]-4-oxobutyl]-2,3,4,11-tetrahydro-11,11-dimethyl-, perchlorate (1:1), ATTO-TEC GmbH, Siegen, Germany).

Scheme 3 below shows the preparation of compound of formula (IP) wherein $R_{11}$, $R_{12}$, B and m have the meanings defined above.

presence of an inorganic or organic, acid such as hydrochloric, trifluoroacetic or methanesulphonic acid in a suitable solvent such as dichloromethane, dichloroethane, dioxane, a lower alcohol, such as methanol or ethanol, at a temperature ranging from room temperature to reflux. Protective groups such as benzyloxycarbonyl and the like can be removed with a suitable reducing agent, such as molecular hydrogen, cyclohexene, cyclohexadiene, formic acid, ammonium formate and the like, in the presence of a hydrogenation catalyst, such as, for instance, palladium on carbon, palladium hydroxide,

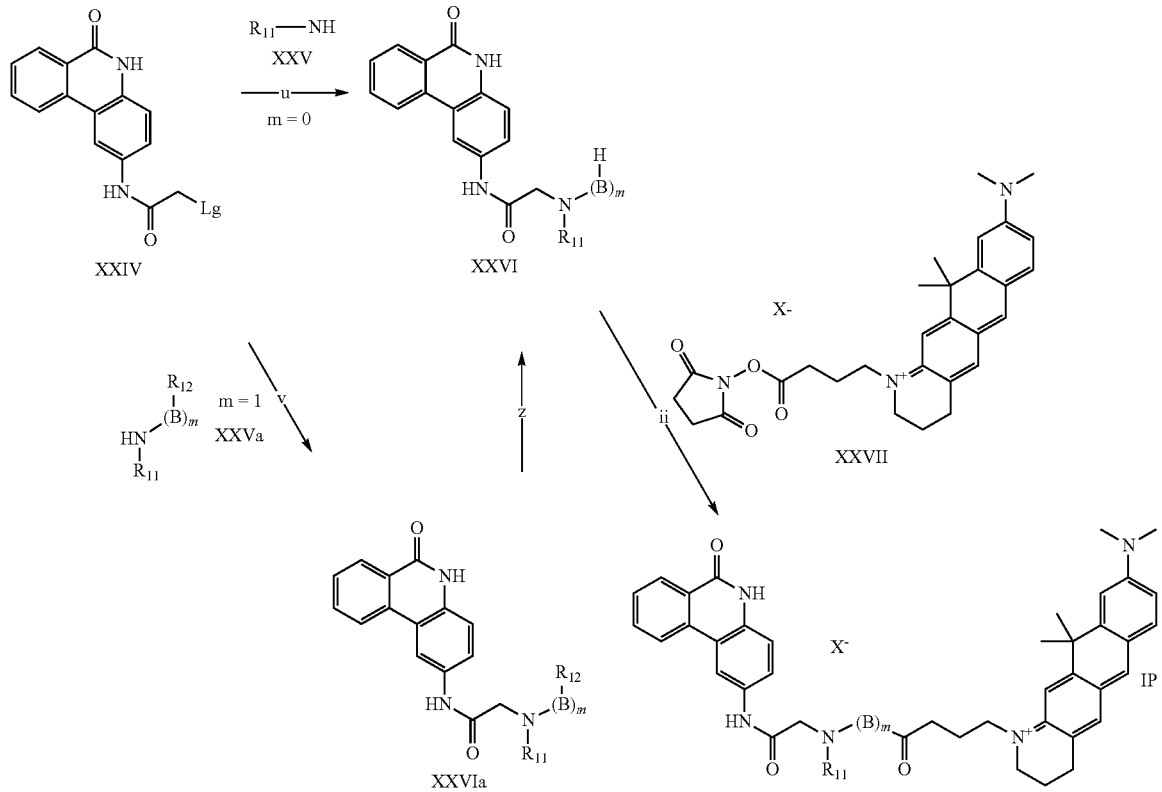

SCHEME 3

According to steps u and v of the process, a compound of formula (XXIV) as defined above is reacted with a compound of formula (XXV) or (XXVa) as defined above, in the presence of a base such as, for instance, sodium or potassium hydroxide, sodium, potassium or cesium carbonate, sodium or potassium hydrogencarbonate, triethylamine, N,N-diisopropylethylamine, pyridine and the like, in a suitable solvent such as acetonitrile, dioxane, methanol, ethanol or N,N-dimethylformamide at a temperature ranging from 0° C. to reflux to give, starting from compound (XXV), as defined above, a compound of the formula (XXVI), as defined above or, starting from compound (XXVa), as defined above, a compound of formula (XXVIa), as defined above;

According to step z of the process, a compound of formula (XXVIa), wherein m=1, $R_{12}$ is a methoxycarbonyl, ethoxycarbonyl, tert-butoxycarbonyl, benzyloxycarbonyl, 9-fluorenylmethoxycarbonyl group or the like, is converted into a compound of formula (XXVI), as defined above, by removing the corresponding nitrogen protective group. In particular, protective groups such as tert-butoxycarbonyl and the like can be removed under acidic conditions, preferably in the palladium black, Ni Raney and the like, in a suitable solvent, such as methanol, ethanol, dioxane and the like at a temperature ranging from room temperature to reflux.

Protective groups such as methoxycarbonyl, ethoxycarbonyl, 9-fluorenylmethoxycarbonyl and the like could be removed under basic conditions such as, for instance, sodium, potassium or cesium carbonate, sodium, potassium or barium hydroxide, hydrazine, piperidine, morpholine and the like in a suitable solvent such as methanol, ethanol, water, N,N-dimethylformamide, N,N-dimethylacetamide and the like, at a temperature ranging from room temperature to reflux.

According to step ii of the process, a compound of formula (XXVI), as defined above, is reacted with a compound of formula (XXVII) in the presence of a suitable base such as triethylamine, N,N-diisopropylethylamine, pyridine and the like, in a solvent such as N,N-dimethylformamide, N,N-dimethylacetamide and the like, at a temperature ranging from 0° C. to room temperature so as to obtain the desired compounds of formula (IP).

The assay is based on the use of a probe of formula (IP) that binds to the NAD binding pocket and takes advantage of the significant change in the polarization signal observed upon binding of the probe to PARP-1, -2 and -3.

The probe of formula (IP) was tested for its ability to bind FL PARP-1, -2 and -3 in a titration experiment. The assay performances were then evaluated (Z' factor) as well as the displacement of the probe by its scaffold and known commercially available PARP inhibitors. In all of the experiments, the polarization signal was measured using a Saphire2 plate reader (Tecan). Data analysis was performed using Dynafit software. In particular, titration data were fitted to the following equilibria: Enzyme+probe<==>Complex Enzyme-probe, while displacement data were fitted to the following equilibria: Enzyme+probe<==>Complex Enzyme-probe, Enzyme+Compound<==>Complex Enzyme-Compound, whereby binding of probe and compound on the enzyme are mutually exclusive (pure competitive mechanism). Displacement data were also fitted using Excell spreadsheet (Microsoft Inc. Seattle, USA) to a four parameter logistic model (4PL), or Hill-Slope model to calculate $DC_{50}$s where the $DC_{50}$ value represents the compound concentration at which the polarization signal is diminished by 50% compared to untreated controls.

The titration experiment was performed as follows: 50 nM probe (compound P1), FL PARP-1, -2 and -3 at concentrations from 5 μM to 0, with dilution steps 1:1.5 in 50 mM TrisHCl, pH 7.8, 150 mM sodium chloride, 10 mM magnesium chloride, 0.001% Triton X100, 1% DMSO (buffer 1). A similar procedure was followed for compound P3 titration.

The obtained results (shown in Table 1 below) indicated that the probe (compound P1) is capable to bind all of the tested isoforms of PARP. For compound P3 only PARP-1 KD is reported. The Z' factor (Z'=1-(3*(SDprobe+protein+SDprobe)/(Meanprobe+protein−Meanprobe)) was determined as follows: 50 nM probe (compound P1), 250 nM of PARP-1 and -2, 200 nM of PARP-3. PARP-1 concentration was equal to 100 nM when compound P3 was used as probe. In all cases, the Z's were higher than 0.7 indicating that the assays were robust (table 1).

TABLE 1

|  | KD (μM) | STD (μM) | Z' |
| --- | --- | --- | --- |
| PARP-1 FL (compound P3) | 0.4 | 0.07 | 0.75 |
| PARP-1 FL (compound P1) | 1.04 | 0.14 | 0.73 |
| PARP-2 FL (compound P1) | 1.05 | 0.2 | 0.78 |
| PARP-3 FL (compound P1) | 0.18 | 0.016 | 0.9 |

The assay was validated using 3-aminobenzamide (3-AB) and PJ-34 (N-(6-oxo-5,6-dihydro-phenanthridin-2-yl)-N,N-dimethylacetamide) in a displacement assay performed as follows: serial dilutions of test compounds were first prepared in 100% DMSO and further diluted in assay buffer 1 in order to have a 1% final DMSO concentration. 3-AB were tested at 100 μM as highest concentration, while 10 μM was PJ-34 highest concentration. The enzymes were present at a final concentration of 250 nM for PARP-1 (100 nM when compound P3 was used as probe) and PARP-2 while 200 nM was used for PARP-3. Probe (compound P1 or compound P3) final concentration was 50 nM. The mixture of enzyme and probe (compound P1 or compound P3) was added to the previously diluted compounds. Results (Table 2) indicate that the probes (compound P1 or compound P3) could be fully displaced by 3-AB and PJ-34 from all of the tested PARP isoforms indicating that the probes (compound P1 or compound P3) binding is specific. In agreement, affinity binding constants (KD) were determined by fitting with a pure competitive mechanism. KD values, are the average of three independent experiments.

3-AB, as expected, was not selective among the PARP isoforms and showed a lower affinity with respect to PJ-34.

TABLE 2

|  | PJ34 KD (μM) | STD (μM) | 3-AB KD (μM) | STD (μM) |
| --- | --- | --- | --- | --- |
| PARP-1 FL (compound P3) | <0.01* | — | 5.56 | 0.55 |
| PARP-1 FL (compound P1) | <0.03* | — | 6.68 | 1.2 |
| PARP-2 FL (compound P1) | <0.03* | — | 7.4 | 1.04 |
| PARP-3 FL (compound P1) | 0.15 | 0.026 | 17.7 | 4.25 |

*assay sensitivity limits based on a fitting error <50%

Taken together, these results show that the displacement assay is specific. Moreover it allows quantitative potency evaluation of standard PARP inhibitors tested, and therefore selectivity evaluation among assays.

The same assay, by using either probe P1 or P3, was used to evaluate compounds of formula (I) as reported in table 3.

TABLE 3

|  | PARP-1 | | PARP-2 | PARP-3 |
| --- | --- | --- | --- | --- |
| Compound | ($DC_{50}$μM) | (Kd μM)* | ($DC_{50}$μM) | ($DC_{50}$μM) |
| 3 | <0.25 | <0.01 | >10 | >10 |
| 4 | <0.25 | <0.01 | >10 | >10 |
| 5 | 2.11 | 0.78 | >10 | >10 |
| 6 | <0.25 | 0.03 | >10 | >10 |
| 7 | <0.25 | 0.03 | >10 | 0.52 |
| 8 | 0.44 | 0.25 | >10 | 3.1 |
| 9 | 0.35 | 0.17 | >10 | >10 |
| 13 | <0.25 | 0.05 | 1.46 | >10 |
| 15 | <0.25 | 0.04 | >10 | >10 |
| 18 | <0.25 | <0.01 | 1.82 | >10 |
| 19 | <0.25 | 0.02 | >10 | 3.04 |
| 20 | <0.25 | <0.01 | >10 | 3.86 |
| 21 | <0.25 | 0.03 | >10 | >10 |
| 22 | <0.25 | 0.04 | >10 | >10 |
| 26 | <0.25 | 0.07 | 6.88 | 2.83 |
| 35 | <0.25 | 0.04 | >10 | >10 |
| 36 | <0.25 | 0.08 | >10 | >10 |
| 38 | 1.11 | — | >10 | >10 |
| 126 | <0.25 | — | >10 | >10 |
| 127 | 0.41 | 0.06 | >10 | >10 |
| 128 | 5.66 | 0.87 | >10 | >10 |

*Assay performed with compound P3 as the probe. In all other cases compound P1 was used as the probe. From the above data, it is clear to a person skilled in the art that compounds of formula (I) of the present invention are highly potent as PARP-1 inhibitors and extremely selective versus PARP-2 and PARP-3 (compare PARP-1 Kd, PARP-2 $DC_{50}$ and PARP-3 $DC_{50}$ values).

Pharmacology

PARP-1 is a DNA damage-induced polymerase that catalyzes the cleavage of NAD+ into nicotinamide and ADP-ribose and then uses the latter to synthesize branched nucleic-acid like polymers poly(ADP-ribose). In vivo, the most abundantly poly (ADP-ribosylated) protein is PARP-1 itself, followed by histones. PARP-1 is responsible for 90% of this DNA damage-induced activity while the remaining 10% is due to PARP-2.

Cellular Assay

Cellular activity of PARP-1 inhibitors was assessed by measuring the inhibition of the hydrogen peroxide induced PAR formation in HeLa cells (ECACC). Cellular PAR levels were measured by immunocytochemistry, and quantified using an ArrayScan vTi instrument (Cellomics Thermo Scientific).

Studies were performed as follows: 6000 cells/well were seeded in 96 well plates (Perkin Elmer) in MEM/10% FCS and incubated for 24 hours at 37° C., 5% carbon dioxide. Test compounds were then added at the required concentration for 30'. DNA damage was then induced adding hydrogen peroxide at the concentration of 0.1 mM for 15 min. Concentration curves were prepared in MEM/10% FCS from compound stocks in DMSO, and final DMSO concentration was 0.002% (v/v). Duplicate wells for each concentration point were prepared with a typical highest compound concentration of 20 µM and serial dilution 1:3. Plates were dried and fixed adding cold methanol-acetone (70:30) solution for 15 min at room temperature, fixing solution was aspired and wells were air dried for 5 min and then dehydrated in PBS. Non-specific binding sites were blocked by incubating wells for 30 min in PBS containing 5% (w/v) FBS 0.05% tween20. Wells were then incubated for 1 hour at room temperature in PBS containing anti PAR mouse monoclonal antibody (Anti-PAR, Mouse mAb 10H, Tulip Cat N° 1020) diluted 1:200 in blocking solution. After 3 washes in PBS, wells incubated in PBS (w/v) 5% FBS 0.05% Tween20 containing 2 µg/mL Cy2-conjugated Goat anti mouse secondary antibody (Amersham Pharmacia Biotech cat. N° PA 42002) (Absorption maximum 489 nm fluorescence maximum 506 nm) and 1 µg/mL DAPI (Absorption maximum 359 nm fluorescence maximum 461 nm) (4',6-Diamidino-2-phenyindole dilactate) (Sigma cat. N° D9564), a high sensitivity dye for nucleic acid staining. After washing further 3 times in PBS, cellular PAR immunoreactivity was assessed using the ArrayScan vTi instrument, with a Zeiss 10×0.5 N.A. objective, and applying the Cytotoxicity.V3 algorithm (Cellomics/Thermo Fisher) with a XF100 filter. At least 10 fields, corresponding to at least 900 cells, were read for each well. $IC_{50}$ values represent the compound concentration at which cellular PAR signal is diminished by 50% compared with untreated controls.

The following formula is used:

$$IC_{50}=\text{Bottom}+(\text{Top}-\text{Bottom})/(1+10^{((\text{Log}\,EC_{50}-X))});$$

X is the logarithm of concentration. $IC_{50}$ is the response; $IC_{50}$ starts at Bottom and goes to Top with a sigmoid shape. Given the above assays, compounds of formula (I) of the present invention inhibited PAR formation with $IC_{50}$ values lower than 10 µM, as depicted in table 4 below.

TABLE 4

| Compound | PAR assay ($IC_{50}$ µM) |
| --- | --- |
| 3 | 0.28 |
| 4 | 0.15 |
| 5 | 6.3 |
| 6 | 1.3 |
| 7 | 7 |
| 9 | 3 |
| 13 | 0.5 |
| 18 | 2.7 |
| 19 | 2.5 |
| 21 | 1.2 |
| 35 | 4.9 |
| 36 | 9 |
| 38 | 5.3 |
| 126 | 0.27 |
| 127 | 0.64 |
| 128 | 4 |

Pharmacokinetics

The pharmacokinetic profile and the oral bioavailability of the compounds have been investigated in the mouse (Balb, Nu/Nu, Harlan, Italy) in ad hoc pharmacokinetic studies. The compounds were formulated in 10% tween 80/dextrose for intravenous bolus administration while oral administrations were performed using the compounds formulated in 0.5% methylcellulose. A single administration at the dose of 10 mg/kg was given and three male animals for each route were used. All blood samples were taken from saphenous vein at 5 min, 30 min, 1 hour, 6 hours, 24 hours after intravenous administration and 15 min, 30 min, 1 hour, 6 hours, 24 hours after oral administration. Plasma samples were prepared by plasma proteins precipitation adding 200 µL of methanol to 10 µL of plasma in a 96 well plate. After capping and vortex mixing, the plate was centrifuged for 15 min at 3700 rpm at 6° C. The supernatant was considered as final extract and injected onto the LC-MS-MS system (HPLC system: Hewlett Packard 1100 series using Atlantis HILIC Silica 50*2.1 mm 5.0 µm analytical column; MS instrument: Perkin Elmer SCIEX API 2000 and ionization performed with Turbo Ion Spray in positive ion mode). Lower limit of quantification is 5.0 ng/mL, upper limit of quantification is 10000 ng/mL. Analysis was performed using the Watson package (version 6.4.0.04) and Excel spreadsheet (Microsoft Inc. Seattle, USA). Non-compartmental method (linear trapezoidal rule and linear regression analysis of natural log-transformed plasma concentrations vs. time data) was used. After intravenous dosing, Co was set equal to Co 083 Absolute bioavailability (F) was calculated from the ratio of average oral to IV (intravenous) dose-normalized plasma AUC (area under curve) values.

Some representative compounds of formula (I) were evaluated for their pharmacokinetic parameters as reported in table 5 as mean value.

TABLE 5

| Compounds | CL (IV bolus) mL/min/kg | Vdss (IV bolus) L/Kg | $AUC_{0-24}$ (oral) µM · hours | C-max (oral) µM | $T^{1/2}$ (oral) hours | F on AUC % |
| --- | --- | --- | --- | --- | --- | --- |
| 3 | 32.6 | 3.61 | 13.5 | 2.53 | 3.04 | 100 |
| 4 | 53.4 | 6.8 | 4.93 | 1.37 | 2.62 | 78 |
| 13 | 26.7 | 4.7 | 18.3 | 3.64 | 2.9 | 100 |
| 18 | 47 | 3.84 | 7.28 | 3.9 | 1.8 | 92 |
| 19 | 88 | 3.9 | 4.28 | 2.85 | 0.8 | 93 |
| 21 | 23 | 4.9 | 7.39 | 1.2 | 6.6 | 56 |

From the above, it is clear to the person skilled in the art that compounds of formula (I) possess good to excellent pharmacokinetics profiles and oral bioavailability.

In Vivo Efficacy Studies

Balb, athymic Nu/Nu male mice, from Harlan (Italy), were maintained in agreement with the European Communities Council Directive no. 86/609/EEC concerning the protection of animals used for experimental or other scientific purposes, in cages with paper filter cover, food and bedding sterilized and acidified water. Fragments of Capan-1 human pancreatic cancer tumors were implanted subcutaneously. Mice bearing a palpable tumor (100-200 mm$^3$) were selected and randomized into control and treated groups. Each group included seven animals. The treatment started one day after randomization. Compound of formula (I) was administered by oral route as a methocel suspension at the indicated doses and times. Tumor dimension was measured regularly by calipers during the experiments and tumor mass was calculated as described in Simeoni M. et al., Cancer Res 64, 1094-1101 (2004). The tumor growth inhibition (TGI, %) was calculated according to the equation: % TGI=100-(mean tumor weight of treated group/mean tumor weight of control group)*100.

Some representative compounds of formula (I), were evaluated for their anti-tumor activity as single agent on Capan-1 BRCA-2 mutated mouse model. Toxicity was evaluated on the basis of body weight reduction (no body weight reduction observed out of 7 mice treated). The results are reported in table 6.

TABLE 6

| Compounds | Dose | Schedule | Max TGI (%) | Toxicity |
|---|---|---|---|---|
| 3 | 100 mg/kg | 1-10 daily | 51% | 0/7 |
| 4 | 75 mg/kg | 1-10 daily | 52% | 0/7 |
| 13 | 100 mg/kg | 1-20 daily | 18% | 0/7 |
| 21 | 100 mg/kg | 1-20 daily | 23% | 0/7 |

Compounds of formula (I) of the present invention, suitable for administration to a mammal, e.g., to humans, can be administered by the usual routes and the dosage level depends upon the age, weight, conditions of the patient and administration route.

For example, a suitable dosage adopted for oral administration of a compound of formula (I) may range from about 1 to about 1000 mg per dose, from 1 to 5 times daily. The compounds of the invention can be administered in a variety of dosage forms, e.g., orally, in the form tablets, capsules, sugar or film coated tablets, liquid solutions or suspensions; rectally in the form suppositories; parenterally, e.g., intramuscularly, or through intravenous and/or intrathecal and/or intraspinal injection or infusion.

As stated above, the present invention also includes pharmaceutical compositions comprising a compound of formula (I) or a pharmaceutically acceptable salt thereof in association with a pharmaceutically acceptable excipient, which may be a carrier or a diluent.

The pharmaceutical compositions containing the compounds of the invention are usually prepared following conventional methods and are administered in a suitable pharmaceutical form. For example, the solid oral forms may contain, together with the active compound, diluents, e.g., lactose, dextrose saccharose, sucrose, cellulose, corn starch or potato starch; lubricants, e.g., silica, talc, stearic acid, magnesium or calcium stearate, and/or polyethylene glycols; binding agents, e.g., starches, arabic gum, gelatine methylcellulose, carboxymethylcellulose or polyvinyl pyrrolidone; disintegrating agents, e.g., starch, alginic acid, alginates or sodium starch glycolate; effervescing mixtures; dyestuffs; sweeteners; wetting agents such as lecithin, polysorbates, laurylsulphates; and, in general, non-toxic and pharmacologically inactive substances used in pharmaceutical formulations. These pharmaceutical preparations may be manufactured in known manner, for example, by means of mixing, granulating, tabletting, sugar-coating, or film-coating processes.

The liquid dispersions for oral administration may be, e.g., syrups, emulsions and suspensions. As an example, the syrups may contain, as carrier, saccharose or saccharose with glycerine and/or mannitol and sorbitol.

The suspensions and the emulsions may contain, as examples of carriers, natural gum, agar, sodium alginate, pectin, methylcellulose, carboxymethylcellulose, or polyvinyl alcohol. The suspension or solutions for intramuscular injections may contain, together with the active compound, a pharmaceutically acceptable carrier, e.g., sterile water, olive oil, ethyl oleate, glycols, e.g., propylene glycol and, if desired, a suitable amount of lidocaine hydrochloride.

The solutions for intravenous injections or infusions may contain, as a carrier, sterile water or preferably they may be in the form of sterile, aqueous, isotonic, saline solutions or they may contain propylene glycol as a carrier.

The suppositories may contain, together with the active compound, a pharmaceutically acceptable carrier, e.g., cocoa butter, polyethylene glycol, a polyoxyethylene sorbitan fatty acid ester surfactant or lecithin.

EXPERIMENTAL SECTION

For a reference to any specific compound of formula (I) of the invention, optionally in the form of a pharmaceutically acceptable salt, see the experimental section and claims. Referring to the examples that follow, compounds of the present invention were synthesized using the methods described herein, or other methods, which are well known in the art.

The short forms and abbreviations used herein have the following meaning:
μM (micromolar)
μL (microliter)
μm (micrometer)
mol (moles)
mM (millimolar)
mmol (millimoles)
g (grams)
mg (milligrams)
$DC_{50}$ (the half maximal Displacement Concentration)
$IC_{50}$ (the half maximal Inhibitory Concentration)
STD (Standard Deviation)
PAR (poly (ADP-ribose))
MEM (Minimal Essential Medium)
FCS (Fetal Calf Serum)
FBS (Fetal Bovine Serum)
PBS (Phosphate Buffered Saline)
LC-MS (Liquid Chromatography-Mass Spectrometry)
HPLC (High Performance Liquid Chromatography)
AUC (area under the plasma concentration vs. time curve up to the last detectable concentration)
Cl (plasma clearance)
Cmax (maximum plasma concentration)
T½ (terminal half life)
Vdss (volume of distribution at steady state)
TGI (Tumor Growth Inhibition)
MHz (megahertz)
Hz (Hertz)
DMSO (dimethylsulfoxide)
ESI (electrospray ionization)

With the aim to better illustrate the present invention, without posing any limitation to it, the following examples are now given.

As used herein the symbols and conventions used in the processes, schemes and examples are consistent with those used in the contemporary scientific literature, for example, the *Journal of the American Chemical Society* or the *Journal of Biological Chemistry*.

Unless otherwise noted, all materials were obtained from commercial suppliers, of the best grade and used without further purification. Anhydrous solvent such as N,N-dimethylformamide, tetrahydrofuran, dichloromethane and toluene were obtained from the Aldrich Chemical Company. All reactions involving air- or moisture-sensitive compounds were performed under nitrogen or argon atmosphere.

General Purification and Analytical Methods

Flash Chromatography was performed on silica gel (Merck grade 9395, 60A). HPLC was performed on Waters X Terra RP 18 (4.6×50 mm, 3.5 μm) column using a Waters 2790 HPLC system equipped with a 996 Waters PDA detector and Micromass mod. ZQ single quadrupole mass spectrometer, equipped with an electrospray (ESI) ion source. Mobile phase A was ammonium acetate 5 mM buffer (pH 5.5 with acetic acid-acetonitrile 95:5), and mobile phase B was water-acetonitrile (5:95). Gradient from 10 to 90% B in 8 minutes, hold 90% B 2 minutes. UV detection at 220 nm and 254 nm. Flow rate 1 mL/min. Injection volume 10 µL. Full scan, mass range from 100 to 800 amu. Capillary voltage was 2.5 KV; source temperature was 120° C.; cone was 10 V. Retention times (HPLC r.t.) are given in minutes at 220 nm or at 254 nm. Mass are given as m/z ratio.

When necessary, compounds were purified by preparative HPLC on a Waters Symmetry C18 (19×50 mm, 5 µm) column or on a Waters X Terra RP 18 (30×150 mm, 5 µm) column using a Waters preparative HPLC 600 equipped with a 996 Waters PDA detector and a Micromass mod. ZMD single quadrupole mass spectrometer, electron spray ionization, positive mode. Mobile phase A was water-0.01% trifluoroacetic acid, and mobile phase B was acetonitrile. Gradient from 10 to 90% B in 8 min, hold 90% B 2 min. Flow rate 20 mL/min. In alternative, mobile phase A was water-0.1% ammonium hydroxide, and mobile phase B was acetonitrile. Gradient from 10 to 100% B in 8 min, hold 100% B 2 min. Flow rate 20 mL/min.

1H-NMR spectrometry was performed on a Mercury VX 400 operating at 400.45 MHz equipped with a 5 mm double resonance probe [1H (15N-31P) ID_PFG Varian].

Example 1

Step a

2-Bromo-4-fluoro-6-methylaniline

A solution of N-bromosuccinimide (18.7 g, 0.105 mol) in 70 mL of N,N-dimethylformamide was added dropwise to a solution of 4-fluoro-2-methylaniline in 70 mL of N,N-dimethylformamide at 20° C. The reaction mixture was stirred overnight. The dark solution was poured into a mixture of water (1000 mL), brine (50 mL) and ethyl acetate (300 mL). The mixture was transferred into a separatory funnel, shacked and separated. The aqueous phase was extracted with ethyl acetate (4×150 mL). The combined organic layers were washed with water (5×100 mL), brine (2×100 mL), dried with sodium sulfate, filtered and concentrated. The $^1$H NMR spectrum of the crude material showed at least 95% purity. The product was further purified on silica gel pad (eluent system ethyl acetate/n-hexane: 1/8). The pure fractions were combined and evaporated to give 14.9 g of product. The impure fractions were combined, concentrated, redissolved in diethyl ether (30 mL) and extracted with 5% hydrochloric acid (5×10 mL). The acidic phase was basified with aq. potassium hydroxide and extracted with diethyl ether to provide 0.8 g of the title compound. Total yield was 15.7 g (77%).

$^1$H NMR (400 MHz, DMSO-d$_6$) δ ppm 7.16 (dd, $^3J_{H-F}$=8.3 Hz, $^4J_{H-H}$=2.9 Hz, 1H, Ar), 6.91 (dd, $^3J_{H-F}$=9.3 Hz, $^4J_{H-H}$=2.9 Hz, 1H, Ar), 4.83 (br. s, 2H, NH$_2$), 2.16 (s, 3H, CH$_3$).

Step b

2-Bromo-4-fluoro-6-methylbenzonitrile

A solution of potassium cyanide (16.25 g, 0.25 mol) in 20 mL of water was added to a suspension of freshly prepared copper(I) chloride (9.5 g, 0.096 mol) in 40 mL of water. copper(I) chloride was observed to dissolve initially and then a minute amount of precipitate was formed. Toluene (30 mL) was added and the mixture was chilled to 0° C. in the fridge. 2-Bromo-4-fluoro-6-methylaniline (15.7 g, 0.077 mol) was added to a mixture of 16.5 mL of 36% aqueous hydrochloric acid and 40 mL of water. The resulting suspension was heated until a solution formed. The solution was chilled to 2° C. with an ice bath and the amine hydrochloride precipitated. A solution of sodium nitrite (5.34 g, 0.078 mol) in 15 mL of water was slowly added keeping the reaction mixture temperature below 5° C. (ice bath). A powder of sodium carbonate decahydrate was added in small portions to adjust the pH of the reaction mixture to about 7.

A solution of the diazonium salt was slowly added to the cyanocuprate reagent keeping the reaction temperature below 5° C. A bright red-orange precipitate formed. The reaction mixture was allowed to warm to 20° C., kept at this temperature for 14 hours. Then it was slowly heated to 70° C. and kept at this temperature for 1 hour. The precipitate dissolved almost completely. The reaction mixture was allowed to cool to 20° C. and filtered. Organic phase was separated and the aqueous phase was extracted with toluene (3×70 mL). The combined organic layers were washed with water (2×100 mL), brine (2×100 mL), dried with sodium sulfate, filtered and concentrated. The crude nitrile (13.9 g, 84%) obtained was used without further purification.

$^1$H NMR (400 MHz, DMSO-d$_6$) δ ppm 7.73 (dd, $^3J_{H-F}$=8.2 Hz, $^4J_{H-H}$=2.1 Hz, 1H, Ar), 7.44 (dd, $^3J_{H-F}$=9.4 Hz, $^4J_{H-H}$=2.0 Hz, 1H, Ar), 2.52 (s, 3H, CH$_3$). $^{13}$C NMR (300 MHz, d6-DMSO) δ 163.5 (d, $^1J_{C-F}$=257 Hz), 147.8 (d, $^3J_{C-F}$=11 Hz), 126.1 (d, $^3J_{C-F}$=11 Hz), 118.4 (d, $^2J_{C-F}$=27 Hz), 117 (d, $^2J_{C-F}$=23 Hz), 115.8, 112.7 (d, $^4J_{C-F}$=3 Hz).

Step c

2-Bromo-4-fluoro-6-methylbenzamide

2-Bromo-4-fluoro-6-methylbenzonitrile (0.428 g, 2 mmol) was heated in 70% aqueous sulfuric acid (2 mL) for 15 hours at 150° C. The reaction mixture was poured into ice and extracted with ethyl acetate (4×2 mL). The organic phase was washed with water (4×2 mL), brine (2×2 mL), dried with sodium sulfate, filtered and concentrated to give 300 mg of crude amide. Pure sample was obtained via recrystallization from benzene $^1$H NMR (400 MHz, DMSO-d$_6$) δ ppm 7.89 (br. s, 1H, NH), 7.65 (br. s, 1H, NH), 7.41 (dd, $^3J_{H-F}$=8.6 Hz, $^4J_{H-H}$=2.2 Hz, 1H, Ar), 7.17 (dd, $^3J_{H-F}$=9.8 Hz, $^4J_{H-H}$=2.2 Hz, 1H, Ar), 3.31 (s, 3H, CH$_3$).

Step d

2-Bromo-4-fluoro-6-methylbenzoic acid

2-Bromo-4-fluoro-6-methylbenzamide (0.9 g, 3.9 mmol) was dissolved in 75% aqueous sulfuric acid (4 mL) at 80° C. sodium nitrite (0.5 g, 7.2 mmol) was carefully added in small portions during 1 hour. At the end of addition a persistent color of nitrogen dioxide appeared. The reaction mixture was chilled to 20° C. and cold water (15 mL) was added to the reaction mixture. The product was extracted with ethyl acetate (6×2 mL). The organic phase was washed with water (4×2 mL), brine (2×2 mL), dried with sodium sulfate, filtered and concentrated to give 0.879 g (97%) of pure acid.

$^1$H NMR (400 MHz, DMSO-d$_6$) δ ppm 13.7 (br. s, 1H, OH), 7.47 (dd, $^3J_{H-F}$=8.5 Hz, $^4J_{H-H}$=2.4 Hz, 1H, Ar), 7.22 (dd, $^3J_{H-F}$=9.6 Hz, $^4J_{H-H}$=2.2 Hz, 1H, Ar), 2.31 (s, 1H, CH$_3$). $^{13}$C NMR (300 MHz, DMSO-d$_6$+CCl$_4$) δ ppm 168, 163 (d, $^1J_{C-F}$=250 Hz), 138.4 (d, $^3J_{C-F}$=8 Hz), 134 (d, $^4J_{C-F}$=3 Hz), 118.3 (d, $^3J_{C-F}$=10 Hz), 116.8 (d, $^2J_{C-F}$=24 Hz), 116 (d, $^2J_{C-F}$=22 Hz), 19.5.

Step e

Methyl 2-bromo-4-fluoro-6-methylbenzoate

A mixture of 2-bromo-4-fluoro-6-methylbenzoic acid (1.94 g, 8.33 mmol), anhydrous potassium carbonate (1.72 g, 12.5 mmol), iodomethane (2.36 g, 17 mmol) in N,N-dimethylformamide (15 mL) was vigorously stirred for 23 hours at 20° C. The suspension was poured into 70 mL of water. A heavy liquid separated. The product was extracted with ethyl acetate (4×25 mL). The organic phase was washed with water (5×20 mL), brine (2×20 mL), dried with sodium sulfate, filtered and concentrated to give 2.07 g (100%) of pure ester. $^1$H NMR (400 MHz, CDCl$_3$) δ ppm 7.18 (dd, $^3J_{H-F}$=8.1 Hz, $^4J_{H-H}$=2.4 Hz, 1H, Ar), 6.91 (dd, $^3J_{H-F}$=9.0 Hz, $^4J_{H-H}$=2.2 Hz, 1H, Ar), 3.96 (s, 3H, OCH$_3$), 2.35 (s, 3H, CH$_3$).

Operating in an analogous way, the following compound was obtained:

Methyl 2-iodo-4-fluoro-6-methylbenzoate $^1$H NMR (400 MHz, DMSO-d$_6$) δ ppm 2.27 (s, 3H) 3.86 (s, 3H) 7.21-7.27 (m, 1H) 7.63 (m, 1H).

Step f

7-Bromo-5-fluoro-2-[3-(morpholin-4-yl)propyl]-2,3-dihydro-1H-isoindol-1-one A mixture of methyl 2-bromo-4-fluoro-6-methylbenzoate (2.07 g, 8.1 mmol), N-bromosuccinimide (1.59 g, 8.91 mmol), benzoyl peroxide (98 mg, 0.41 mmol) in carbon tetrachloride was heated at reflux for 4 hours. 68 mg of benzoyl peroxide were added and the mixture was refluxed for another 3 hours. The chilled reaction mixture was filtered and evaporated to give 2.9 g of oily residue. The residue was dissolved in 20 mL of toluene. N-(3-aminopropyl)-morpholine (1.16 g, 8.1 mmol) and anhydrous potassium carbonate (3.35 g, 24.3 mmol) were added to the solution and the reaction mixture was heated at 95° C. for 15 hours, chilled, filtered through Celite and concentrated. The product was recrystallized from 5 mL of toluene providing 1 g of target product (35%).

$^1$H NMR (400 MHz, CDCl$_3$) δ ppm 7.36 (dd, $^3J_{H-F}$=8.8 Hz, $^4J_{H-H}$=2.2 Hz, 1H, Ar), 7.09-7.13 (m, 1H, Ar), 4.35 (s, 1H, CH$_2$), 3.62-3.74 (m, 6H), 2.34-2.49 (m, 6H), 1.87 (quintet, $^3J_{H-H}$=7.1 Hz, 1H, CH$_2$CH$_2$CH$_2$).

Operating in an analogous way, the following compound was obtained:

7-Bromo-2-(1-cyclohexylpiperidin-4-yl)-5-fluoro-2,3-dihydro-1H-isoindol-1-one $^1$H NMR (400 MHz, DMSO-d$_6$) δ ppm 1.20 (m, 4H) 1.70 m (10H), 2.29 (br. s., 3H) 2.91 (d, J=10.99 Hz, 2H) 3.82-4.03 (m, 1H) 4.42 (s, 2H) 7.51 (dd, J=8.18, 2.07 Hz, 1H) 7.62 (dd, J=9.03, 2.20 Hz, 1H).

Tert-butyl 4-(5-fluoro-7-iodo-1-oxo-1,3-dihydro-2H-isoindol-2-yl)piperidine-1-carboxylate $^1$H NMR (400 MHz, DMSO-d$_6$) δ ppm 7.81 (dd, J=2.20, 8.91 Hz, 1H), 7.51 (dd, J=2.20, 8.30 Hz, 1H), 4.37 (s, 2H), 4.16 (tt, J=4.15, 11.78 Hz, 1H), 4.06 (d, J=14.04 Hz, 2H), 2.84 (br. s., 2H), 1.68-1.78 (m, 2H), 1.62 (qd, J=3.80, 12.40 Hz, 2H), 1.42 (s, 9H)

Step p

7-Bromo-2-(1-cyclohexylpiperidin-4-yl)-5-fluoro-3-methyl-2,3-dihydro-1H-isoindol-1-one To a stirred solution of 7-bromo-2-(1-cyclohexylpiperidin-4-yl)-5-fluoro-2,3-dihydro-1H-isoindol-1-one (70 mg, 0.177 mmol) and methyliodide (1.1 equiv., 0.195 mmol, 0.012 mL) in anhydrous tetrahydrofuran (3.5 mL) under nitrogen at −78° C., 1M sodium bis(trimethylsilyl)amide in tetrahydrofuran (1.2 equiv., 0.212 mL) was slowly added. The reaction mixture was stirred for 90 min and quenched by adding dropwise a 10% ammonium hydroxide solution. Dichloromethane was added, the layers were separated, and the aqueous layer was extracted twice dichloromethane. Organic layers were collected, dried and evaporated. Crude (58 mg) was used without further purification.

ESI(+) MS: m/z 409-411 (MH$^+$).

Operating in an analogous way, the following compound was obtained:

Tert-butyl 4-(6-fluoro-4-iodo-1-methyl-3-oxo-1,3-dihydro-2H-isoindol-2-yl)piperidine-1-carboxylate $^1$H NMR (400 MHz, DMSO-d$_6$) δ ppm 7.78 (dd, J=2.20, 8.79 Hz, 1H), 7.54-7.60 (m, J=0.50, 0.50, 0.50, 1.77, 8.36 Hz, 1H), 4.62 (q, J=7.00 Hz, 1H), 4.05 (br. s., 2H), 3.85 (tt, J=3.88, 11.99 Hz, 1H), 2.79 (br. s., 2H), 2.07 (qd, J=4.33, 12.55 Hz, 1H), 1.91 (qd, J=4.52, 12.45 Hz, 1H), 1.64-1.79 (m, 2H), 1.42 (s, 9H), 1.39-1.47 (m, 3H)

Operating in an analogous way but in excess of alkylating agent (10 equiv.) and base (5 equiv.) the following compounds were obtained:

7-Bromo-2-(1-cyclohexylpiperidin-4-yl)-5-fluoro-3,3-dimethyl-2,3-dihydro-1H-isoindol-1-one ESI(+) MS: m/z 423-425 (MH$^+$).

Tert-butyl 4-(6-fluoro-4-iodo-1,1-dimethyl-3-oxo-1,3-dihydro-2H-isoindol-2-yl)piperidine-1-carboxylate $^1$H NMR (400 MHz, DMSO-d$_6$) δ ppm 7.75 (dd, J=2.14, 8.85 Hz, 1H), 7.66 (dd, J=2.20, 8.42 Hz, 1H), 4.04 (br. s., 2H), 3.48-3.59 (m, 1H), 2.79 (br. s., 2H), 2.34-2.47 (m, 2H), 1.47-1.57 (m, 2H), 1.45 (s, 6H), 1.43 (s, 9H)

Step h

Tert-butyl 4-(4-cyano-6-fluoro-1-methyl-3-oxo-1,3-dihydro-2H-isoindol-2-yl)piperidine-1-carboxylate Tert-butyl 4-(6-fluoro-4-iodo-1-methyl-3-oxo-1,3-dihydro-2H-isoindol-2-yl)piperidine-1-carboxylate (240 mg, 0.5 mmol) and copper(I) cyanide (67 mg, 0.75 mmol) were dissolved in N,N-dimethylformamide (2 mL) and the resulting solution was refluxed under nitrogen atmosphere for 3 hours. The solvent was removed under reduced pressure and the residue was diluted with dichloromethane and washed with 15% ammonium hydroxide. Organic phase was dried over sodium sulfate, filtered and evaporated. Column chromatography (dichloromethane/ethanol:95/5) afforded title compound (174 mg, 93% yield).

$^1$H NMR (400 MHz, DMSO-d$_6$) δ ppm 7.90-7.99 (m, 2H), 4.78 (q, J=6.67 Hz, 1H), 4.06 (d, J=11.23 Hz, 2H), 3.86 (tt, J=3.94, 12.05 Hz, 1H), 2.80 (br. s., 2H), 2.10 (qd, J=3.97, 12.47 Hz, 1H), 1.95 (qd, J=4.21, 12.35 Hz, 1H), 1.73 (t, J=15.07 Hz, 2H), 1.48 (d, J=6.71 Hz, 3H), 1.42 (s, 9H)

Operating in an analogous way, the following compound was obtained:

Tert-butyl 4-(4-cyano-6-fluoro-1,1-dimethyl-3-oxo-1,3-dihydro-2H-isoindol-2-yl)piperidine-1-carboxylate $^1$H NMR (400 MHz, DMSO-$d_6$) δ ppm 8.03 (dd, J=2.20, 8.42 Hz, 1H), 7.93 (dd, J=2.20, 9.15 Hz, 1H), 4.04 (d, J=4.76 Hz, 2H), 3.54-3.68 (m, 1H), 2.78 (br. s., 2H), 2.36-2.47 (m, 2H), 1.52-1.59 (m, 2H), 1.50 (s, 6H), 1.43 (s, 9H)

Conversion 3

6-Fluoro-1-methyl-3-oxo-2-(piperidin-4-yl)-2,3-dihydro-1H-isoindole-4-carbonitrile hydrochloride A solution of tert-butyl 4-(4-cyano-6-fluoro-1-methyl-3-oxo-1,3-dihydro-2H-isoindol-2-yl)piperidine-1-carboxylate (2.7 g, 7.5 mmol) in 4M hydrochloric acid in dioxane (18 mL, 75 mmol) was stirred at 50° C. for 2 hours until HPLC analysis revealed the disappearance of the starting material. The solvent was removed under reduce pressure and the product was dissolved in diethyl ether and decanted to obtain the title compound (2.09 g, 95%) as its corresponding hydrochloride.

ESI(+) MS: m/z 274 (MH$^+$).

Operating in an analogous way, the following compound was obtained:

6-Fluoro-1,1-dimethyl-3-oxo-2-(piperidin-4-yl)-2,3-dihydro-1H-isoindole-4-carbonitrile hydrochloride $^1$H NMR (400 MHz, DMSO-$d_6$) δ ppm 8.78 (br. s., 1H), 8.39 (br. s., 1H), 8.04 (dd, J=2.20, 8.42 Hz, 1H), 7.95 (dd, J=2.20, 9.15 Hz, 1H), 3.66-3.81 (m, 1H), 3.35-3.42 (m, 2H), 2.97 (br. s., 2H), 2.77 (br. s., 2H), 1.75 (br. s., 2H), 1.50 (s, 6H)

Conversion 4

2-[1-(4,4-Difluorocyclohexyl)piperidin-4-yl]-6-fluoro-1-methyl-3-oxo-2,3-dihydro-1H-isoindole-4-carbonitrile To a suspension of 6-fluoro-1-methyl-3-oxo-2-(piperidin-4-yl)-2,3-dihydro-1H-isoindole-4-carbonitrile hydrochloride (153 mg, 0.5 mmol) in dichloromethane (5 mL) 4,4-difluoro-cyclohexanone (100 mg, 0.75 mmol) sodium acetate (82 mg, 1 mmol) and methanol (1 mL) were added. The resulted solution was stirred at room temperature for 5 hours. Then sodium cyanoborohydride (95 mg, 1.51 mmol) was added and the mixture was stirred overnight. The solvents were removed under reduce pressure and the residue was dissolved in dichloromethane and washed twice with water. The organic phase was dried over anhydrous sodium sulfate and concentrated in vacuo and the residue was purified by flash chromatography (dichloromethane/methanol 95:5) to give the title compound (90 mg, 46%).

$^1$H NMR (400 MHz, DMSO-$d_6$) δ ppm 7.89-7.99 (m, 2H), 4.77 (q, J=6.63 Hz, 1H), 3.69 (br. s., 1H), 2.85-2.99 (m, 2H), 2.18-2.31 (m, 2H), 1.46-1.51 (m, 3H)

Operating in an analogous way, the following compounds were obtained:

2-(1-Cyclohexylpiperidin-4-yl)-6-fluoro-1-methyl-3-oxo-2,3-dihydro-1H-isoindole-4-carbonitrile ESI(+) MS: m/z 357 (MH$^+$).

2-(1-Cyclohexylpiperidin-4-yl)-6-fluoro-1,1-dimethyl-3-oxo-2,3-dihydro-1H-isoindole-4-carbonitrile ESI(+) MS: m/z 370 (MH$^+$).

Step i

2-[1-(4,4-Difluorocyclohexyl)piperidin-4-yl]-6-fluoro-1-methyl-3-oxo-2,3-dihydro-1H-isoindole-4-carboxylic acid hydrochloride 2-[1-(4,4-Difluorocyclohexyl)piperidin-4-yl]-6-fluoro-1-methyl-3-oxo-2,3-dihydro-1H-isoindole-4-carbonitrile (80 mg, 0.2 mmol) was dissolved in 37% hydrochloric acid (2 mL) and the resulted solution was refluxed for 16 hours. The solvent was removed under reduced pressure and the residue was diluted with methanol and decanted in order to obtained the desired product as white solid (80 mg, 97%).

ESI(+) MS: m/z 411 (MH$^+$).

Operating in an analogous way, the following compounds were obtained:

2-(1-Cyclohexylpiperidin-4-yl)-6-fluoro-1-methyl-3-oxo-2,3-dihydro-1H-isoindole-4-carboxylic acid hydrochloride ESI(+) MS: m/z 375 (MH$^+$).

2-(1-Cyclohexylpiperidin-4-yl)-6-fluoro-1,1-dimethyl-3-oxo-2,3-dihydro-1H-isoindole-4-carboxylic acid hydrochloride ESI(+) MS: m/z 389 (MH$^+$).

2-[1-(4,4-Difluorocyclohexyl)piperidin-4-yl]-6-fluoro-1-methyl-3-oxo-2,3-dihydro-1H-isoindole-4-carboxamide, cpd. 126

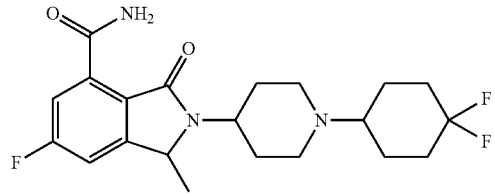 [SMILES: CC1c2cc(F)cc(C(N)=O)c2C(=O)N1C1CCN(C2CCC(F)(F)CC2)CC1]

To a solution of 2-[1-(4,4-difluorocyclohexyl)piperidin-4-yl]-6-fluoro-1-methyl-3-oxo-2,3-dihydro-1H-isoindole-4-carboxylic acid hydrochloride (80 mg, 0.2 mmol) in N,N-dimethylformamide (2 mL) hydroxybenzotriazole ammonium salt (61 mg, 0.4 mmol), 1-ethyl-3-(3'-dimethylamino) carbodiimide hydrochloric acid salt (77 mg, 0.4 mmol) and N,N-diisopropylethylamine (0.14 mL, 1 mmol) were added. The reaction mixture was stirred at room temperature overnight. The solvent was removed under reduce pressure and the residue was dissolved in ethyl acetate. The solution was washed twice with sodium carbonate saturated aqueous solution, and the organic phase was dried over anhydrous sodium sulfate and concentrated in vacuo. The crude was purified by flash chromatography (dichloromethane/methanol 96:4) to afford the title compound (60 mg, 73%) as a white solid.

$^1$H NMR (400 MHz, DMSO-d$_6$) δ ppm 10.73 (br. s., 1H), 7.87 (dd, J=2.62, 10.80 Hz, 1H), 7.84 (br. s., 1H), 7.70-7.76 (m, 1H), 4.79 (q, J=6.75 Hz, 1H), 3.71-3.81 (m, 1H), 2.87-3.01 (m, 2H), 1.51 (d, J=6.59 Hz, 3H)

Operating in an analogous way, the following compounds were obtained:

2-(1-Cyclohexylpiperidin-4-yl)-6-fluoro-1-methyl-3-oxo-2,3-dihydro-1H-isoindole-4-carboxamide, cpd. 127

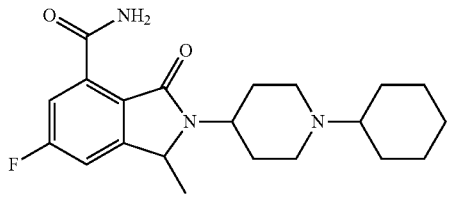 [SMILES: CC1c2cc(F)cc(C(N)=O)c2C(=O)N1C1CCN(C2CCCCC2)CC1]

$^1$H NMR (400 MHz, DMSO-d$_6$) δ ppm 10.69 (br. s., 1H), 7.87 (dd, J=2.50, 10.68 Hz, 1H), 7.84 (br. s., 1H), 7.73 (dd, J=2.20, 7.69 Hz, 1H), 4.73-4.83 (m, 1H), 1.51 (d, J=6.59 Hz, 3H).

2-(1-Cyclohexylpiperidin-4-yl)-6-fluoro-1,1-dimethyl-3-oxo-2,3-dihydro-1H-isoindole-4-carboxamide, cpd. 128

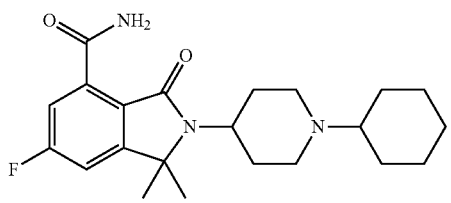 [SMILES: CC1(C)c2cc(F)cc(C(N)=O)c2C(=O)N1C1CCN(C2CCCCC2)CC1]

$^1$H NMR (400 MHz, DMSO-d$_6$) δ ppm 10.67 (br. s., 1H), 7.86 (dd, J=2.50, 10.80 Hz, 1H), 7.72 (dd, J=2.50, 7.87 Hz, 1H), 7.35-7.62 (m, 1H), 3.25-3.48 (m, 1H), 2.86-2.99 (m, J=3.78 Hz, 2H), 2.53-2.66 (m, J=3.30, 12.69 Hz, 2H), 2.17-2.43 (m, 3H), 1.71-1.89 (m, J=8.18, 8.18 Hz, 4H), 1.53-1.65 (m, J=10.01 Hz, 2H), 1.51 (s, 6H), 1.18-1.32 (m, 4H), 1.02-1.17 (m, 1H).

Example 2

Step n 4-(1-Furan-2-yl-ethylamino)-piperidine-1-carboxylic acid tert-butyl ester To an equimolar solution of 1-furan-2-yl-ethanone (250 mg, 2.27 mmol) and 4-amino-piperidine-1-carboxylic acid tert-butyl ester (454 mg, 2.27 mmol) in dichloromethane (14 mL) 1M titanium(IV) chloride in dichloromethane (1.13 mL, 1.13 mmol) and triethylamine (0.31 mL, 2.27 mmol) were added. The reaction mixture was stirred under nitrogen atmosphere for 2 days. Then sodium cyanoborohydride (430 mg, 6.8 mmol) in methanol (7 mL) was added dropwise with stirring and the solution was allowed to stir overnight at room temperature. 35% sodium hydroxide was added and the product was extracted with ethyl acetate. The solvent was removed under reduce pressure and the crude was purified by flash chromatography (dichloromethane/methanol:95/5) to give the final compound as a red oil (406 mg, 61%).

$^1$H NMR (400 MHz, DMSO-d$_6$) δ ppm 7.51 (dd, J=0.85, 1.83 Hz, 1H), 6.35 (dd, J=1.83, 3.17 Hz, 1H), 6.19 (dt, J=0.66, 3.20 Hz, 1H), 3.91 (q, J=6.88 Hz, 1H), 3.76 (tt, J=4.10, 13.50 Hz, 2H), 2.73 (br. s., 2H), 1.65-1.96 (m, 2H), 1.47-1.64 (m, 1H), 1.38 (s, 9H), 1.26 (d, J=6.71 Hz, 3H), 0.98-1.15 (m, 2H). ESI(+) MS: m/z 295 (MH$^+$).

Operating in an analogous way, the following compounds were obtained:

N-[1-(Furan-2-yl)ethyl]-4-(morpholin-4-yl)aniline $^1$H NMR (400 MHz, DMSO-d$_6$) δ ppm 7.50 (dd, J=0.85, 1.83 Hz, 1H), 6.71 (d, J=8.91 Hz, 2H), 6.54 (d, J=8.91 Hz, 2H), 6.32 (dd, J=1.83, 3.17 Hz, 1H), 6.15 (dt, J=0.69, 3.14 Hz, 1H), 5.39 (d, J=8.30 Hz, 1H), 4.50 (qd, J=6.71, 7.20 Hz, 1H), 3.64-3.73 (m, 4H), 2.83-2.92 (m, 4H), 1.41 (d, J=6.84 Hz, 3H).

N-[1-(Furan-2-yl)ethyl]-4-(piperidin-1-yl)aniline $^1$H NMR (400 MHz, DMSO-d$_6$) δ ppm 7.50 (dd, J=0.79, 1.77 Hz, 1H), 6.69 (d, J=8.67 Hz, 2H), 6.52 (d, J=8.91 Hz, 2H), 6.32 (dd, J=1.83, 3.17 Hz, 1H), 6.15 (d, J=3.17 Hz, 1H), 5.35 (d, J=8.42 Hz, 1H), 4.49 (qd, J=6.71, 7.12 Hz, 1H), 2.85 (t, J=5.00 Hz, 4H), 1.59 (quin, J=5.40 Hz, 4H), 1.42-1.50 (m, 2H), 1.40 (d, J=6.71 Hz, 3H).

N-[1-(Furan-2-yl)ethyl]-4-(4-methylpiperazin-1-yl)aniline $^1$H NMR (400 MHz, DMSO-d$_6$) δ ppm 7.50 (dd, J=0.85, 1.83 Hz, 1H), 6.69 (d, J=8.91 Hz, 2H), 6.53 (d, J=8.91 Hz, 2H), 6.32 (dd, J=1.83, 3.17 Hz, 1H), 6.14 (dt, J=0.70, 3.23 Hz, 1H), 5.36 (d, J=8.30 Hz, 1H), 4.49 (quin, J=7.11 Hz, 1H), 2.79-2.99 (m, 4H), 2.34-2.47 (m, 4H), 2.19 (s, 3H), 1.40 (d, J=6.71 Hz, 3H).

N-[1-(Furan-2-yl)ethyl]-4-(piperidin-1-ylmethyl)aniline $^1$H NMR (400 MHz, DMSO-d$_6$) δ ppm 7.52 (dd, J=0.85, 1.83 Hz, 1H), 6.93 (d, J=7.69 Hz, 2H), 6.54 (d, J=8.30 Hz, 2H), 6.33 (dd, J=1.83, 3.17 Hz, 1H), 6.18 (dt, J=0.72, 3.20 Hz, 1H), 5.78 (br. s., 1H), 4.56 (quin, J=7.02 Hz, 1H), 3.21 (br. s., 2H), 2.25 (br. s., 4H), 1.45 (br. s., 4H), 1.43 (d, J=6.71 Hz, 3H), 1.28-1.41 (m, 2H).

(1S)-1-(Furan-2-yl)-N-[(1R)-1-phenylethyl]ethanamine $^1$H NMR (400 MHz, DMSO-d$_6$) δ ppm 7.50 (br. s., 1H), 7.24-7.36 (m, 4H), 7.15-7.24 (m, 1H), 6.33 (dd, J=1.89, 2.87 Hz, 1H), 6.17 (d, J=2.56 Hz, 1H).

(1R)-1-(Furan-2-yl)-N-[(1R)-1-phenylethyl]ethanamine $^1$H NMR (400 MHz, DMSO-d$_6$) δ ppm 7.53 (br. s., 1H), 7.24-7.35 (m, 1H), 7.16-7.24 (m, 1H), 6.36 (dd, J=1.65, 2.50

Hz, 1H), 6.09 (d, J=2.56 Hz, 1H), 3.56 (q, J=6.59 Hz, 1H), 3.41 (q, J=7.12 Hz, 1H), 1.22 (d, J=6.84 Hz, 3H), 1.17 (d, J=6.47 Hz, 3H).

Step o 3-(1-Tert-butoxycarbonyl-piperidin-4-yl)-2-methyl-4-oxo-10-oxa-3-aza-tricyclo[5.2.1.0*1,5*]dec-8-ene-6-carboxylic acid To a solution of 4-(1-furan-2-yl-ethylamino)-piperidine-1-carboxylic acid tert-butyl ester (6.4 g, 21 mmol) in toluene (300 mL) maleic anhydride (2.1 g, 21 mmol) was added. The reaction mixture was refluxed for 6 hours and then stirred overnight at room temperature. The precipitate solid obtained was filtered, washed with diethyl ether and dried to give the desired compound (6.8 g, 82%) as a white solid.

$^1$H NMR (400 MHz, DMSO-$d_6$) δ ppm 12.00 (br. s., 1H), 6.58 (d, J=5.86 Hz, 1H), 6.45 (dd, J=1.77, 5.80 Hz, 1H), 4.93 (d, J=1.59 Hz, 1H), 4.00 (d, J=12.45 Hz, 2H), 3.89 (q, J=6.55 Hz, 1H), 3.69 (tt, J=3.80, 12.01 Hz, 1H), 2.91 (d, J=9.28 Hz, 1H), 2.71 (br. s., 2H), 2.43 (d, J=9.28 Hz, 1H), 1.40 (s, 9H), 1.37 (d, J=6.59 Hz, 3H). ESI(+) MS: m/z 393 (MH$^+$).

Operating in an analogous way, the following compounds were obtained:

3-Methyl-2-[4-(morpholin-4-yl)phenyl]-1-oxo-1,2,3,6,7,7a-hexahydro-3a,6-epoxyisoindole-7-carboxylic acid $^1$H NMR (400 MHz, DMSO-$d_6$) δ ppm 12.14 (br. s., 2H), 7.39 (d, J=9.03 Hz, 2H), 7.11 (d, J=9.03 Hz, 2H), 6.96 (d, J=9.03 Hz, 2H), 6.94 (d, J=9.15 Hz, 2H), 6.66 (d, J=5.74 Hz, 1H), 6.60 (d, J=5.74 Hz, 1H), 6.52 (dd, J=1.71, 5.86 Hz, 1H), 6.49 (dd, J=1.71, 5.74 Hz, 1H), 5.04 (d, J=1.71 Hz, 1H), 5.02 (d, J=1.71 Hz, 1H), 4.82 (q, J=6.59 Hz, 1H), 4.50 (q, J=6.59 Hz, 1H), 3.68-3.79 (m, 8H), 3.14 (d, J=9.15 Hz, 1H), 3.10 (td, J=4.46, 5.77 Hz, 8H), 2.93 (d, J=9.15 Hz, 1H), 2.57 (d, J=9.15 Hz, 1H), 2.53 (d, J=9.15 Hz, 1H), 1.36 (d, J=6.71 Hz, 3H), 1.06 (d, J=6.47 Hz, 3H).

3-Methyl-1-oxo-2-[4-(piperidin-1-yl)phenyl]-1,2,3,6,7,7a-hexahydro-3a,6-epoxyisoindole-7-carboxylic acid $^1$H NMR (400 MHz, DMSO-$d_6$) δ ppm 12.13 (br. s., 2H), 7.36 (d, J=8.54 Hz, 2H), 7.08 (d, J=8.79 Hz, 2H), 6.95 (d, J=7.93 Hz, 4H), 6.66 (d, J=5.74 Hz, 1H), 6.60 (d, J=5.74 Hz, 1H), 6.52 (dd, J=1.71, 5.74 Hz, 2H), 6.49 (dd, J=1.71, 5.61 Hz, 1H), 6.19 (s, 1H), 5.04 (d, J=1.71 Hz, 1H), 5.02 (d, J=1.71 Hz, 1H), 4.80 (q, J=6.55 Hz, 1H), 4.48 (q, J=6.47 Hz, 2H), 1.58-1.70 (m, 8H), 1.48-1.57 (m, 4H), 1.36 (d, J=6.71 Hz, 3H), 1.05 (d, J=6.47 Hz, 3H).

3-Methyl-2-[4-(4-methylpiperazin-1-yl)phenyl]-1-oxo-1,2,3,6,7,7a-hexahydro-3a,6-epoxyisoindole-7-carboxylic acid ESI(+) MS: m/z 384 (MH$^+$).

3-Methyl-1-oxo-2-[4-(piperidin-1-ylmethyl)phenyl]-1,2,3,6,7,7a-hexahydro-3a,6-epoxyisoindole-7-carboxylic acid $^1$H NMR (400 MHz, DMSO-$d_6$) δ ppm 6.70 (d, J=5.86 Hz, 1H), 6.62 (d, J=5.74 Hz, 1H), 6.55 (dd, J=1.71, 5.86 Hz, 1H), 6.52 (dd, J=1.71, 5.86 Hz, 1H), 5.07 (d, J=1.46 Hz, 1H), 5.04 (d, J=1.71 Hz, 1H), 4.99 (q, J=5.94 Hz, 1H), 4.74 (q, J=6.63 Hz, 1H), 1.43 (d, J=6.59 Hz, 3H), 1.13 (d, J=6.47 Hz, 3H).

Step p

1-Methyl-3-oxo-2-piperidin-4-yl-2,3-dihydro-1H-isoindole-4-carboxylic acid 3-(1-Tert-butoxycarbonyl-piperidin-4-yl)-2-methyl-4-oxo-10-oxa-3-aza-tricyclo[5.2.1.0*1,5*]dec-8-ene-6-carboxylic acid (6.6 g, 16.8 mmol) was dissolved in aqueous 37% hydrochloric acid (80 mL) and the resulted solution was refluxed for 3 hours. The solvent was removed under reduced pressure and the residue was diluted with methanol and decanted in order to obtained the desired product as white solid (3.8 g, 82%).

$^1$H NMR (400 MHz, DMSO-$d_6$) δ ppm 15.84 (br. s., 1H), 8.65-8.97 (m, 2H), 8.55 (br. s., 1H), 8.15 (dd, J=0.55, 7.63 Hz, 1H), 7.95 (d, J=7.57 Hz, 1H), 7.85 (t, J=7.69 Hz, 1H), 4.98 (q, J=6.59 Hz, 1H), 4.15 (tt, J=3.74, 12.19 Hz, 1H), 3.38 (d, J=12.57 Hz, 1H), 2.90-3.14 (m, 2H), 2.35 (qd, J=4.00, 13.20 Hz, 1H), 2.00 (t, J=10.50 Hz, 2H), 1.59 (d, J=6.71 Hz, 3H). ESI(+) MS: m/z 275 (MH$^+$).

Operating in an analogous way, the following compounds were obtained:

1-Methyl-2-[4-(morpholin-4-yl)phenyl]-3-oxo-2,3-dihydro-1H-isoindole-4-carboxylic acid $^1$H NMR (400 MHz, DMSO-$d_6$) δ ppm 15.74 (br. s., 1H), 8.19 (d, J=7.81 Hz, 1H), 8.02 (d, J=7.57 Hz, 1H), 7.85-7.94 (m, 1H), 7.47 (d, J=9.03 Hz, 2H), 7.09 (d, J=9.15 Hz, 2H), 5.50 (q, J=6.71 Hz, 1H), 3.70-3.82 (m, 4H), 3.16-3.21 (m, 4H), 1.38 (d, J=6.71 Hz, 3H).

1-Methyl-3-oxo-2-[4-(piperidin-1-yl)phenyl]-2,3-dihydro-1H-isoindole-4-carboxylic acid $^1$H NMR (400 MHz, DMSO-$d_6$) δ ppm 12.13 (br. s., 2H), 7.36 (d, J=8.54 Hz, 2H), 7.08 (d, J=8.79 Hz, 2H), 6.95 (d, J=7.93 Hz, 4H), 6.66 (d, J=5.74 Hz, 1H), 6.60 (d, J=5.74 Hz, 1H), 6.52 (dd, J=1.71, 5.74 Hz, 2H), 6.49 (dd, J=1.71, 5.61 Hz, 1H), 6.19 (s, 1H), 5.04 (d, J=1.71 Hz, 1H), 5.02 (d, J=1.71 Hz, 1H), 4.80 (q, J=6.55 Hz, 1H), 4.48 (q, J=6.47 Hz, 2H), 1.58-1.70 (m, 8H), 1.48-1.57 (m, 4H), 1.36 (d, J=6.71 Hz, 3H), 1.05 (d, J=6.47 Hz, 3H).

1-Methyl-2-[4-(4-methylpiperazin-1-yl)phenyl]-3-oxo-2,3-dihydro-1H-isoindole-4-carboxylic acid $^1$H NMR (400 MHz, DMSO-$d_6$) δ ppm 15.66 (br. s., 1H), 10.28 (br. s., 1H), 8.19 (d, J=7.57 Hz, 1H), 8.02 (d, J=7.57 Hz, 1H), 7.90 (t, J=7.69 Hz, 1H), 7.51 (d, J=8.91 Hz, 2H), 7.15 (d, J=9.03 Hz, 2H), 5.52 (q, J=6.67 Hz, 1H), 2.85 (d, J=4.39 Hz, 3H), 1.38 (d, J=6.84 Hz, 3H).

1-Methyl-3-oxo-2-[4-(piperidin-1-ylmethyl)phenyl]-2,3-dihydro-1H-isoindole-4-carboxylic acid ESI(+) MS: m/z 365 (MH$^+$).

Conversion 2

2-(1-Tert-butoxycarbonyl-piperidin-4-yl)-1-methyl-3-oxo-2,3-dihydro-1H-isoindole-4-carboxylic acid To a solution of 1-methyl-3-oxo-2-piperidin-4-yl-2,3-dihydro-1H-isoindole-4-carboxylic acid (4 g, 13.2 mmol) in pyridine (15 mL) potassium carbonate (3.6 g, 26.5 mol) and methanol (40 mL) were successively added. Then di-tert-butyl dicarbonate (3.16 g, 14.5 mmol) was added and the reaction mixture was stirred at room temperature for 4 hours until HPLC analysis revealed the disappearance of the starting material. The solvent was removed under reduced pressure and the residue was dissolved in dichloromethane. The solution was washed twice with 5% potassium hydrogen sulfate and the organic phase was dried over anhydrous sodium sulfate and concentrated in vacuo. The obtained crude wad diluted with diethyl ether and decanted to obtain the desired product (3.8 g, 78%) as a white solid.

$^1$H NMR (400 MHz, DMSO-$d_6$) δ ppm 15.97 (s, 1H), 8.15 (dd, J=0.61, 7.69 Hz, 1H), 7.93 (d, J=7.57 Hz, 1H), 7.83 (t, J=7.57 Hz, 1H), 4.98 (q, J=6.63 Hz, 1H), 4.07 (d, J=12.08 Hz, 2H), 4.01 (tt, J=3.85, 12.33 Hz, 1H), 2.83 (br. s., 2H), 2.11 (qd, J=4.39, 12.33 Hz, 1H), 1.97 (qd, J=4.46, 12.43 Hz, 1H), 1.82 (t, J=13.12 Hz, 2H), 1.55 (d, J=6.71 Hz, 3H), 1.43 (s, 9H). ESI(+) MS: m/z 375 (MH$^+$).

Step i'"

Tert-butyl-4-(4-carbamoyl-1-methyl-3-oxo-1,3-dihydro-2H-isoindol-2-yl)piperidine-1-carboxylate cpd. 1

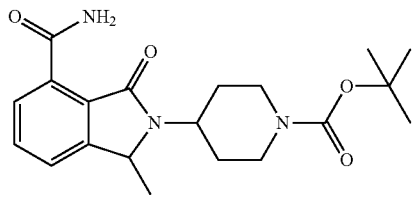 [SMILES: CC1c2cccc(C(N)=O)c2C(=O)N1C1CCN(C(=O)OC(C)(C)C)CC1]

To an orange solution of 2-(1-tert-butoxycarbonyl-piperidin-4-yl)-1-methyl-3-oxo-2,3-dihydro-1H-isoindole-4-carboxylic acid (3.8 g, 10.3 mmol) in N,N-dimethylformamide (60 mL) hydroxybenzotriazole ammonium salt (3.15 g, 20.7 mmol), 1-ethyl-3-(3'-dimethylamino) carbodiimide hydrochloric acid salt (3.34 g, 20.7 mmol) and N,N-diisopropylethylamine (5.3 mL, 30.9 mmol) were added. The reaction mixture was stirred at room temperature overnight. The solvent was removed under reduce pressure and the residue was dissolved in ethyl acetate. The solution was washed twice with sodium carbonate saturated aqueous solution, and the organic phase was dried over anhydrous sodium sulfate and concentrated in vacuo. The crude was purified by flash chromatography (dichloromethane/methanol: 97:3) to afford the title compound (2.86 g, 74%) as a white solid.

$^1$H NMR (400 MHz, DMSO-$d_6$) δ ppm 10.60 (br. s., 1H), 8.17 (dd, J=1.10, 7.57 Hz, 1H), 7.78 (ddd, J=0.50, 1.10, 7.69 Hz, 1H), 7.72 (t, J=7.60 Hz, 1H), 7.65 (br. s., 1H), 4.79 (d, J=6.71 Hz, 1H), 4.06 (d, J=12.00 Hz, 2H), 3.96 (tt, J=3.98, 12.07 Hz, 1H), 2.82 (br. s., 2H), 2.10 (qd, J=4.64, 12.45 Hz, 1H), 1.94 (qd, J=4.58, 12.35 Hz, 1H), 1.77 (t, J=12.76 Hz, 2H), 1.49 (d, J=6.71 Hz, 3H), 1.42 (s, 9H). ESI(+) MS: m/z 374 (MH$^+$).

Operating in an analogous way, the following compounds were obtained:

1-Methyl-2-[4-(morpholin-4-yl)phenyl]-3-oxo-2,3-dihydro-1H-isoindole-4-carboxamide, cpd. 35

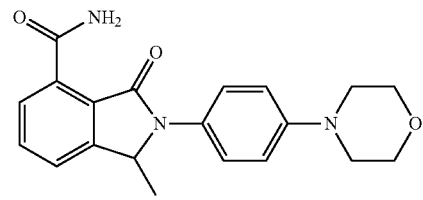 [SMILES: CC1c2cccc(C(N)=O)c2C(=O)N1c1ccc(N2CCOCC2)cc1]

$^1$H NMR (400 MHz, DMSO-$d_6$) δ ppm 10.37 (br. s., 1H), 8.20 (dd, J=0.85, 7.69 Hz, 1H), 7.87 (d, J=7.50 Hz, 1H), 7.79 (t, J=7.69 Hz, 1H), 7.69 (br. s., 1H), 7.43 (d, J=9.03 Hz, 2H), 7.05 (d, J=9.15 Hz, 2H), 5.35 (q, J=6.47 Hz, 1H), 3.70-3.81 (m, 4H), 3.16 (dd, J=4.27, 5.61 Hz, 4H), 1.34 (d, J=6.71 Hz, 3H).

1-Methyl-3-oxo-2-[4-(piperidin-1-yl)phenyl]-2,3-dihydro-1H-isoindole-4-carboxamide, cpd. 36

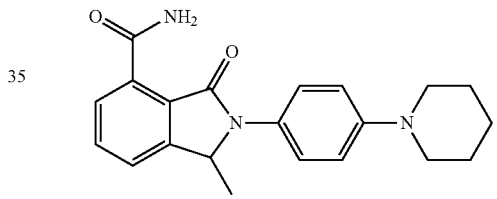

$^1$H NMR (400 MHz, DMSO-$d_6$) δ ppm 10.41 (br. s., 1H), 8.20 (dd, J=0.73, 7.69 Hz, 1H), 7.86 (d, J=7.70 Hz, 1H), 7.79 (t, J=7.65 Hz, 1H), 7.69 (br. s., 1H), 7.38 (d, J=9.03 Hz, 2H), 7.02 (d, J=9.03 Hz, 2H), 5.32 (q, J=6.63 Hz, 1H), 3.15-3.22 (m, 4H), 1.59-1.70 (m, 4H), 1.48-1.60 (m, 2H), 1.33 (d, J=6.59 Hz, 3H).

1-Methyl-2-[4-(4-methylpiperazin-1-yl)phenyl]-3-oxo-2,3-dihydro-1H-isoindole-4-carboxamide, cpd. 37

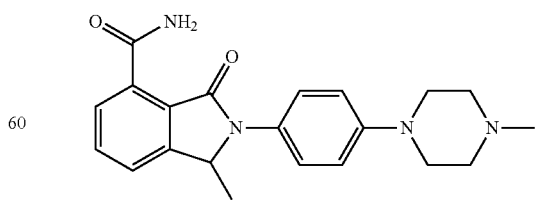

$^1$H NMR (400 MHz, DMSO-$d_6$) δ ppm 10.39 (br. s., 1H), 8.20 (dd, J=0.85, 7.69 Hz, 1H), 7.87 (d, J=7.60 Hz, 1H), 7.79 (t, J=7.63 Hz, 1H), 7.69 (br. s., 1H), 7.41 (d, J=9.03 Hz, 2H), 7.04 (d, J=9.15 Hz, 2H), 5.34 (q, J=6.67 Hz, 1H), 3.19 (t, J=4.90 Hz, 4H), 2.48 (t, J=4.64 Hz, 4H), 2.24 (s, 3H), 1.33 (d, J=6.71 Hz, 3H).

1-Methyl-3-oxo-2-[4-(piperidin-1-ylmethyl)phenyl]-2,3-dihydro-1H-isoindole-4-carboxamide, cpd. 38

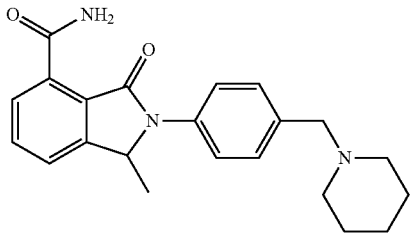 [SMILES: CC1c2cccc(C(N)=O)c2C(=O)N1c1ccc(CN2CCCCC2)cc1]

$^1$H NMR (400 MHz, DMSO-d$_6$) δ ppm 10.16 (br. s., 1H), 8.18 (dd, J=0.73, 7.69 Hz, 1H), 7.88 (d, J=7.60 Hz, 1H), 7.81 (t, J=7.56 Hz, 1H), 7.71 (br. s., 1H), 7.56 (d, J=8.18 Hz, 2H), 7.40 (d, J=8.30 Hz, 2H), 5.45 (q, J=6.43 Hz, 1H), 3.46 (s, 2H), 2.35 (br. s., 4H), 1.51 (quin, J=5.50 Hz, 4H), 1.38-1.45 (m, 2H), 1.36 (d, J=6.71 Hz, 3H).

Conversion 3

1-Methyl-3-oxo-2-(piperidin-4-yl)-2,3-dihydro-1H-isoindole-4-carboxamide, cpd. 2

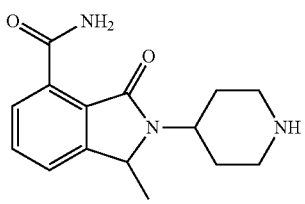 [SMILES: CC1c2cccc(C(N)=O)c2C(=O)N1C1CCNCC1]

A solution of tert-butyl-4-(4-carbamoyl-1-methyl-3-oxo-1,3-dihydro-2H-isoindol-2-yl)piperidine-1-carboxylate (2.8 g, 7.5 mmol) in 4M hydrochloric acid in dioxane (18 mL, 75 mmol) was stirred at 50° C. for 2 hours until HPLC analysis revealed the disappearance of the starting material. The solvent was removed under reduce pressure and the product was dissolved in diethyl ether and decanted to obtain the title compound (2 g 95%) as its hydrochloride.

$^1$H NMR (400 MHz, DMSO-d$_6$) δ ppm 10.53 (br. s., 1H), 8.80 (d, J=9.89 Hz, 1H), 8.64 (q, J=10.54 Hz, 1H), 8.18 (dd, J=1.10, 7.57 Hz, 1H), 7.80 (d, J=7.60 Hz, 1H), 7.74 (t, J=7.60 Hz, 1H), 7.69 (br. s., 1H), 4.81 (q, J=6.67 Hz, 1H), 4.11 (tt, J=4.01, 12.16 Hz, 1H), 2.91-3.14 (m, J=23.44 Hz, 2H), 1.95 (d, J=14.04 Hz, 2H), 1.54 (d, J=6.71 Hz, 3H). ESI(+) MS: m/z 274 (MH$^+$).

Conversion 4

2-(1-Cyclohexylpiperidin-4-yl)-1-methyl-3-oxo-2,3-dihydro-1H-isoindole-4-carboxamide, cpd. 3

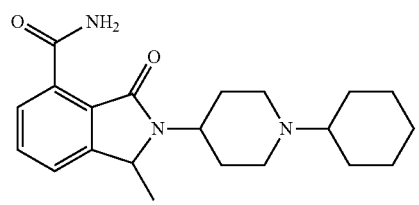 [SMILES: CC1c2cccc(C(N)=O)c2C(=O)N1C1CCN(C2CCCCC2)CC1]

To a suspension of 1-methyl-3-oxo-2-(piperidin-4-yl)-2,3-dihydro-1H-isoindole-4-carboxamide (60 mg, 0.19 mmol) in dichloromethane (2 mL) cyclohexanone (147 mg, 0.28 mmol) sodium acetate (32 mg, 0.38 mmol) and methanol (0.3 mL) were added. The resulted solution was stirred at room temperature for 5 hours. Then sodium cyanoborohydride was added and the mixture was stirred overnight. The solvents were removed under reduce pressure and the residue was dissolved in dichloromethane and washed twice with water. The organic phase was dried over anhydrous sodium sulfate and concentrated in vacuo and the residue was purified by flash chromatography (dichloromethane/methanol: 95:5) to give the title compound.

$^1$H NMR (400 MHz, DMSO-d$_6$) δ ppm 10.70 (br. s., 1H), 8.13-8.22 (m, 1H), 7.77 (d, J=7.30 Hz, 1H), 7.71 (t, J=7.57 Hz, 1H), 7.65 (br. s., 1H), 4.79 (q, J=6.75 Hz, 1H), 3.77 (tt, J=4.06, 12.24 Hz, 1H), 2.92 (t, J=10.38 Hz, 2H), 2.28 (q, J=12.00 Hz, 3H), 2.12 (qd, J=3.90, 12.20 Hz, 1H), 1.97 (qd, J=3.72, 11.94 Hz, 1H), 1.75 (br. s., 6H), 1.58 (d, J=12.08 Hz, 1H), 1.50 (d, J=6.71 Hz, 3H), 1.13-1.30 (m, 4H), 0.99-1.13 (m, 1H). ESI(+) MS: m/z 356 (MH$^+$). Single enantiomers (99% e.e.) have been obtained by preparative chiral-HPLC by using Chiralcel OD 50×500 mm 20 μm as column system and n-hexane/ethanol/methanol 80:10:10 as eluant. Configuration of the stereogenic center was assigned by comparison with cpd 4 obtained by synthesis starting from optically pure (1S)-1-(furan-2-yl)ethanamine (see example 4).

(1S)-2-(1-Cyclohexylpiperidin-4-yl)-1-methyl-3-oxo-2,3-dihydro-1H-isoindole-4-carboxamide, cpd 4

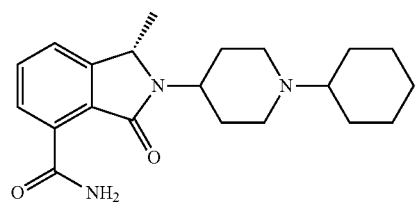 [SMILES: C[C@H]1c2cccc(C(N)=O)c2C(=O)N1C1CCN(C2CCCCC2)CC1]

First eluting peak, $^1$H NMR (400 MHz, DMSO-d$_6$) δ ppm 10.70 (br. s., 1H), 8.18 (dd, J=1.04, 7.63 Hz, 1H), 7.74-7.81 (m, 1H), 7.67-7.75 (m, 1H), 7.65 (br. s., 1H), 4.79 (q, J=6.55 Hz, 1H), 3.57-3.94 (m, 1H), 2.92 (t, J=10.62 Hz, 2H), 2.19-

2.38 (m, 3H), 2.05-2.19 (m, 1H), 1.90-2.05 (m, 1H), 1.75 (br. s., 11H), 1.54-1.62 (m, 2H), 1.49 (d, J=6.59 Hz, 3H). ESI(+) MS: m/z 356 (MH$^+$).

(1R)-2-(1-Cyclohexylpiperidin-4-yl)-1-methyl-3-oxo-2,3-dihydro-1H-isoindole-4-carboxamide, cpd 5

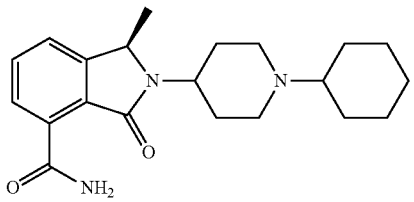 [SMILES: C[C@@H]1c2cccc(C(N)=O)c2C(=O)N1C1CCN(C2CCCCC2)CC1]

Second eluting peak, $^1$H NMR (400 MHz, DMSO-d$_6$) δ ppm 10.70 (br. s., 1H), 8.18 (dd, J=1.10, 7.57 Hz, 1H), 7.75-7.80 (m, 1H), 7.68-7.75 (m, 1H), 7.65 (br. s., 1H), 4.79 (q, J=6.59 Hz, 1H), 3.67-3.87 (m, 1H), 2.92 (t, J=10.44 Hz, 2H), 2.19-2.39 (m, 3H), 2.12 (qd, J=3.72, 12.02 Hz, 1H), 1.88-2.05 (m, 1H), 1.75 (br. s., 6H), 1.53-1.66 (m, 2H), 1.49 (d, J=6.59 Hz, 3H), 1.12-1.29 (m, 4H), 1.09 (t, J=7.02 Hz, 1H). ESI(+) MS: m/z 356 (MH$^+$).

2-[1-(4,4-Difluorocyclohexyl)piperidin-4-yl]-1-methyl-3-oxo-2,3-dihydro-1H-isoindole-4-carboxamide, cpd 6

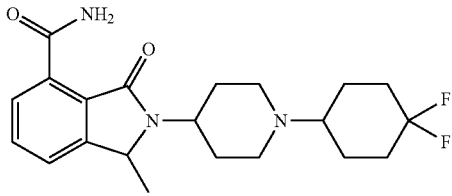 [SMILES: CC1c2cccc(C(N)=O)c2C(=O)N1C1CCN(C2CCC(F)(F)CC2)CC1]

The title compound was prepared as described in Conversion 4 replacing 4,4-difluoro-cyclohexanone for cyclohexanone.

$^1$H NMR (400 MHz, DMSO-d$_6$) δ ppm 10.69 (br. s., 1H), 8.18 (dd, J=1.04, 7.51 Hz, 1H), 7.77 (d, J=7.60 Hz, 1H), 7.72 (t, J=7.60 Hz, 1H), 7.65 (br. s., 1H), 4.79 (q, J=6.55 Hz, 1H), 3.78 (tt, J=3.95, 12.04 Hz, 1H), 2.95 (t, J=9.70 Hz, 2H), 2.25 (q, J=10.62 Hz, 2H), 1.50 (d, J=6.71 Hz, 3H). ESI(+) MS: m/z 392 (MH$^+$).

2-[1-(1H-Indo)-5-ylmethyl)piperidin-4-yl]-1-methyl-3-oxo-2,3-dihydro-1H-isoindole-4-carboxamide, cpd 7

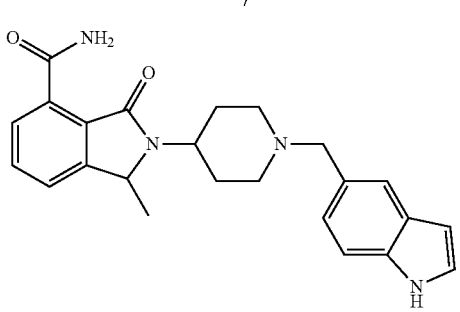

The title compound was prepared as described in Conversion 4 replacing 1H-indole-5-carbaldehyde for cyclohexanone.

$^1$H NMR (400 MHz, DMSO-d$_6$) δ ppm 11.00 (br. s., 1H), 10.69 (br. s., 1H), 8.17 (dd, J=1.10, 7.57 Hz, 1H), 7.77 (d, J=7.60 Hz, 1H), 7.71 (t, J=7.60 Hz, 1H), 7.65 (br. s., 1H), 7.45 (br. s., 1H), 7.34 (d, J=8.30 Hz, 1H), 7.30 (t, J=2.69 Hz, 1H), 7.07 (dd, J=1.04, 8.36 Hz, 1H), 6.39 (t, J=2.01 Hz, 1H), 4.79 (q, J=6.55 Hz, 1H), 3.71-3.90 (m, 1H), 3.55 (br. s., 2H), 2.83-3.07 (m, 2H), 2.12-2.29 (m, J=12.57 Hz, 1H), 1.93-2.13 (m, 3H), 1.65-1.84 (m, 2H), 1.50 (d, J=6.71 Hz, 3H). ESI(+) MS: m/z 403 (MH$^+$).

1-Methyl-3-oxo-2-(1-{[1-(propan-2-yl)-1H-indol-3-yl]methyl}piperidin-4-yl)-2,3-dihydro-1H-isoindole-4-carboxamide, cpd 8

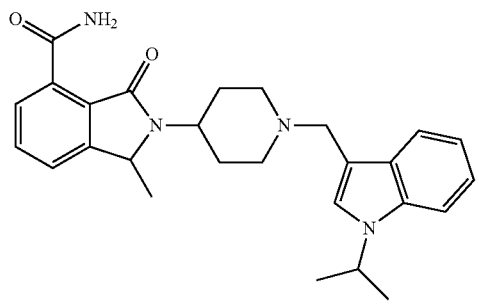 [SMILES: CC1c2cccc(C(N)=O)c2C(=O)N1C1CCN(Cc2cn(C(C)C)c3ccccc23)CC1]

The title compound was prepared as described in Conversion 4 replacing 1-isopropyl-1H-indole-3-carbaldehyde for cyclohexanone.

$^1$H NMR (400 MHz, DMSO-d$_6$) δ ppm 10.67 (br. s., 1H), 8.17 (dd, J=0.98, 7.57 Hz, 1H), 7.74-7.78 (m, 1H), 7.68-7.73 (m, 1H), 7.61-7.69 (m, 2H), 7.46 (d, J=8.42 Hz, 1H), 7.38 (br. s., 1H), 7.12 (t, J=7.45 Hz, 1H), 6.97-7.06 (m, J=7.45 Hz, 1H), 4.64-4.86 (m, 2H), 3.78 (br. s., 1H), 3.66 (br. s., 2H), 3.02 (br. s., 2H), 1.49 (d, J=6.59 Hz, 3H), 1.46 (d, J=6.71 Hz, 6H). ESI(+) MS: m/z 445 (MH$^+$).

1-Methyl-3-oxo-2-[1-(pyridin-2-ylmethyl)piperidin-4-yl]-2,3-dihydro-1H-isoindole-4-carboxamide, cpd 9

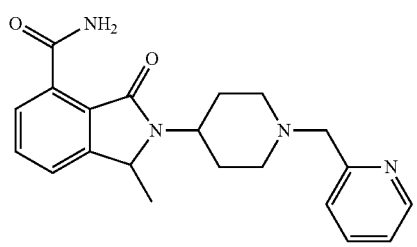 [SMILES: CC1c2cccc(C(N)=O)c2C(=O)N1C1CCN(Cc2ccccn2)CC1]

The title compound was prepared as described in Conversion 4 replacing pyridine-2-carbaldehyde for cyclohexanone.

$^1$H NMR (400 MHz, DMSO-d$_6$) δ ppm 10.68 (br. s., 1H), 8.50 (d, J=3.91 Hz, 1H), 8.18 (dd, J=0.98, 7.57 Hz, 1H), 7.75-7.81 (m, 2H), 7.69-7.74 (m, 1H), 7.66 (br. s., 1H), 7.47-7.49 (m, 1H), 7.23-7.29 (m, 1H), 4.80 (q, J=6.55 Hz, 1H), 3.75-3.87 (m, 1H), 3.64 (br. s., 2H), 2.85-3.03 (m, 2H), 2.07-2.34 (m, 4H), 1.69-1.82 (m, 2H), 1.51 (d, J=6.71 Hz, 3H). ESI(+) MS: m/z 365 (MH$^+$).

2-(1-{[4-(Benzyloxy)-1H-indol-3-yl]methyl}piperidin-4-yl)-1-methyl-3-oxo-2,3-dihydro-1H-isoindole-4-carboxamide, cpd 10

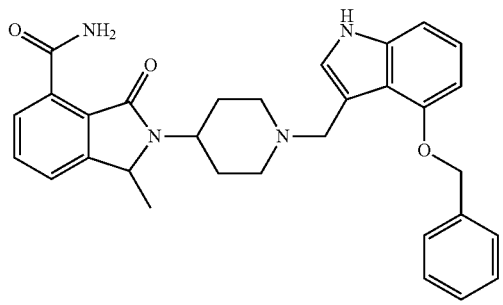 [SMILES: CC1c2cccc(C(N)=O)c2C(=O)N1C1CCN(Cc2c[nH]c3cccc(OCc4ccccc4)c23)CC1]

The title compound was prepared as described in Conversion 4 replacing 4-benzyloxy-1H-indole-3-carbaldehyde for cyclohexanone.

$^1$H NMR (400 MHz, DMSO-d$_6$) δ ppm 10.92 (br. s., 1H), 10.69 (br. s., 1H), 8.17 (dd, J=1.04, 7.63 Hz, 1H), 7.74-7.80 (m, J=1.02, 7.63 Hz, 1H), 7.71 (t, J=7.63 Hz, 1H), 7.65 (br. s., 1H), 7.58 (d, J=7.20 Hz, 2H), 7.42 (t, J=7.45 Hz, 2H), 7.34 (t, J=7.35 Hz, 1H), 7.09 (br. s., 1H), 6.90-7.01 (m, 2H), 6.56 (quin, J=4.27 Hz, 1H), 5.19 (s, 2H), 4.76 (q, J=6.51 Hz, 1H), 3.73 (br. s., 3H), 2.83-3.05 (m, 2H), 1.59-1.79 (m, 2H), 1.47 (d, J=6.59 Hz, 3H). ESI(+) MS: m/z 509 (MH$^+$).

1-Methyl-2-{1-[(4-methyl-1,3-thiazol-5-yl)methyl]piperidin-4-yl}-3-oxo-2,3-dihydro-1H-isoindole-4-carboxamide, cpd 11

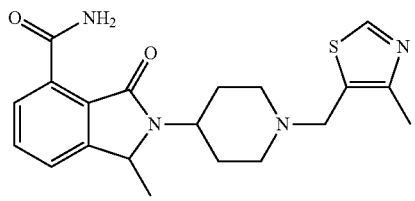 [SMILES: Cc1ncsc1CN1CCC(N2C(=O)c3c(C(N)=O)cccc3C2C)CC1]

The title compound was prepared as described in Conversion 4 replacing 4-methyl-thiazole-5-carbaldehyde for cyclohexanone.

$^1$H NMR (400 MHz, DMSO-d$_6$) δ ppm 10.66 (br. s., 1H), 8.90 (s, 1H), 8.17 (dd, J=1.04, 7.63 Hz, 1H), 7.77 (d, J=7.63 Hz, 1H), 7.72 (t, J=7.60 Hz, 1H), 7.65 (br. s., 1H), 4.79 (q, J=6.47 Hz, 1H), 3.73-3.89 (m, 1H), 3.68 (s, 2H), 2.95 (t, J=10.01 Hz, 2H), 2.35 (s, 3H), 1.97-2.29 (m, 4H), 1.76 (t, J=11.80 Hz, 2H), 1.50 (d, J=6.59 Hz, 3H). ESI (+)ESI(+) MS: m/z 385 (MH$^+$).

2-[1-(2,4-Difluorobenzyl)piperidin-4-yl]-1-methyl-3-oxo-2,3-dihydro-1H-isoindole-4-carboxamide, cpd 12

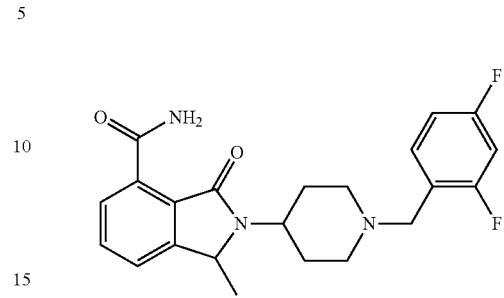

The title compound was prepared as described in Conversion 4 replacing 2,4-difluoro-benzaldehyde for cyclohexanone.

$^1$H NMR (400 MHz, DMSO-d$_6$) δ ppm 10.67 (br. s., 1H), 8.18 (dd, J=1.04, 7.63 Hz, 1H), 7.78 (d, J=7.60 Hz, 1H), 7.72 (t, J=7.60 Hz, 1H), 7.65 (br. s., 1H), 7.10-7.34 (m, 3H), 4.79 (q, J=6.51 Hz, 1H), 3.71-3.89 (m, 1H), 3.57 (s, 2H), 2.85-3.02 (m, 2H), 2.00-2.31 (m, 4H), 1.67-1.84 (m, 2H), 1.50 (d, J=6.59 Hz, 3H). ESI(+) MS: m/z 400 (MH$^+$).

2-(1-Cyclopentylpiperidin-4-yl)-1-methyl-3-oxo-2,3-dihydro-1H-isoindole-4-carboxamide, cpd 13

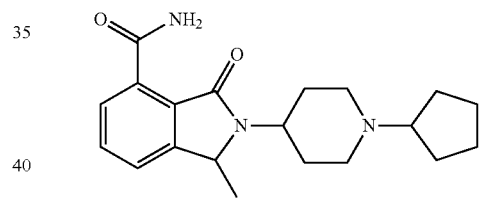

The title compound was prepared as described in Conversion 4 replacing cyclopentanone for cyclohexanone.

$^1$H NMR (400 MHz, DMSO-d$_6$) δ ppm 10.61 (br. s., 1H), 8.18 (dd, J=0.98, 7.57 Hz, 1H), 7.79 (d, J=7.60 Hz, 1H), 7.73 (t, J=7.60 Hz, 1H), 7.67 (br. s., 1H), 4.80 (q, J=6.43 Hz, 1H), 3.91 (br. s., 1H), 1.51 (d, J=6.59 Hz, 3H). ESI(+) MS: m/z 342 (MH$^+$).

1-Methyl-2-{1-[(6-methylpyridin-2-yl)methyl]piperidin-4-yl}-3-oxo-2,3-dihydro-1H-isoindole-4-carboxamide, cpd 14

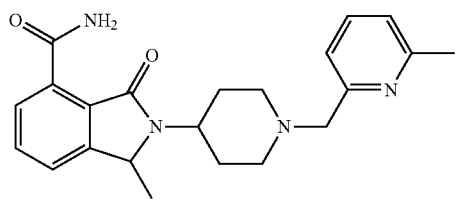 [SMILES: Cc1cccc(CN2CCC(N3C(=O)c4c(C(N)=O)cccc4C3C)CC2)n1]

The title compound was prepared as described in Conversion 4 replacing 6-methyl-pyridine-2-carbaldehyde for cyclohexanone.

¹H NMR (400 MHz, DMSO-d₆) δ ppm 10.68 (br. s., 1H), 8.18 (dd, J=1.04, 7.63 Hz, 1H), 7.78 (dd, J=1.10, 7.60 Hz, 1H), 7.72 (t, J=7.60 Hz, 1H), 7.66 (s, 1H), 7.66 (t, J=7.60 Hz, 1H), 7.27 (d, J=7.69 Hz, 1H), 7.12 (d, J=7.57 Hz, 1H), 4.80 (q, J=6.55 Hz, 1H), 3.82 (br. s., 1H), 3.58 (br. s., 2H), 2.90-3.05 (m, 2H), 2.45 (s, 3H), 1.67-1.85 (m, 2H), 1.51 (d, J=6.59 Hz, 3H). ESI(+) MS: m/z 379 (MH⁺).

2-[1-(Furan-2-ylmethyl)piperidin-4-yl]-1-methyl-3-oxo-2,3-dihydro-1H-isoindole-4-carboxamide, cpd 15

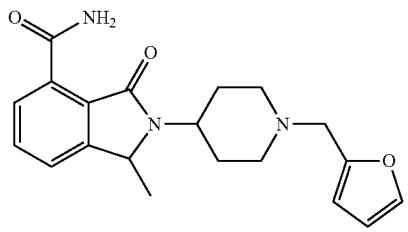 [SMILES: CC1c2cccc(C(N)=O)c2C(=O)N1C1CCN(Cc2ccco2)CC1]

The title compound was prepared as described in Conversion 4 replacing furan-2-carbaldehyde for cyclohexanone.

¹H NMR (400 MHz, DMSO-d₆) δ ppm 10.66 (br. s., 1H), 8.16 (dd, J=1.04, 7.51 Hz, 1H), 7.73-7.78 (m, 1H), 7.67-7.73 (m, 1H), 7.61-7.66 (m, 1H), 7.58 (s, 1H), 6.36-6.42 (m, 1H), 6.36-6.42 (m, 1H), 6.25-6.31 (m, 1H), 6.29 (br. s., 1H), 4.77 (q, J=6.55 Hz, 1H), 3.76 (d, J=14.28 Hz, 1H), 3.52 (br. s., 2H), 2.88-2.98 (m, 2H), 2.13-2.24 (m, 2H), 1.98-2.11 (m, 5H), 1.68-1.80 (m, 3H), 1.48 (d, 3H). ESI(+) MS: m/z 354 (MH⁺).

1-Methyl-3-oxo-2-{1-[3-(piperidin-1-yl)benzyl]piperidin-4-yl}-2,3-dihydro-1H-isoindole-4-carboxamide, cpd 16

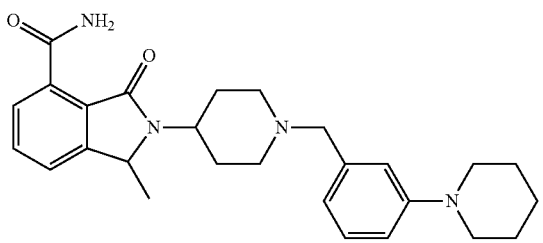 [SMILES: CC1c2cccc(C(N)=O)c2C(=O)N1C1CCN(Cc2cccc(N3CCCCC3)c2)CC1]

The title compound was prepared as described in Conversion 4 replacing 3-piperidin-1-yl-benzaldehyde for cyclohexanone.

¹H NMR (400 MHz, DMSO-d₆) δ ppm 10.68 (br. s., 1H), 8.18 (dd, J=1.16, 7.63 Hz, 1H), 7.75-7.80 (m, 1H), 7.68-7.75 (m, 1H), 7.66 (br. s., 1H), 7.15 (t, J=7.81 Hz, 1H), 6.87 (br. s., 1H), 6.81 (d, J=8.67 Hz, 1H), 6.73 (d, J=7.45 Hz, 1H), 4.80 (q, J=6.47 Hz, 1H), 3.68-3.89 (m, 1H), 3.44 (br. s., 2H), 3.07-3.17 (m, 4H), 2.90-3.00 (m, 2H), 1.97-2.28 (m, 4H), 1.69-1.81 (m, 2H), 1.57-1.68 (m, 4H), 1.53-1.57 (m, 1H), 1.51 (d, J=6.71 Hz, 3H). ESI(+) MS: m/z 447 (MH⁺).

1-Methyl-2-(1-{[6-(morpholin-4-yl)pyridin-2-yl]methyl}piperidin-4-yl)-3-oxo-2,3-dihydro-1H-isoindole-4-carboxamide, cpd 17

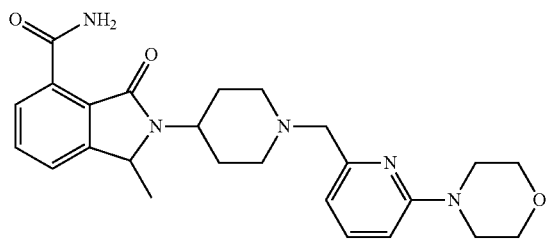 [SMILES: CC1c2cccc(C(N)=O)c2C(=O)N1C1CCN(Cc2cccc(N3CCOCC3)n2)CC1]

The title compound was prepared as described in Conversion 4 replacing 6-morpholin-4-yl-pyridine-2-carbaldehyde for cyclohexanone.

¹H NMR (400 MHz, DMSO-d₆) δ ppm 10.69 (br. s., 1H), 8.18 (dd, J=1.04, 7.63 Hz, 1H), 7.76-7.81 (m, 1H), 7.69-7.75 (m, 1H), 7.66 (br. s., 1H), 7.55 (t, J=7.81 Hz, 1H), 6.79 (d, J=7.20 Hz, 1H), 6.68 (d, J=8.30 Hz, 1H), 4.74-4.84 (m, 1H), 3.81 (t, J=7.32 Hz, 1H), 3.66-3.72 (m, 4H), 3.48 (s, 2H), 3.40-3.45 (m, 4H), 2.90-3.04 (m, 2H), 2.04-2.31 (m, 4H), 1.68-1.82 (m, 2H), 1.51 (d, J=6.59 Hz, 3H). ESI(+) MS: m/z 450 (MH⁺).

2-(1-Cyclobutylpiperidin-4-yl)-1-methyl-3-oxo-2,3-dihydro-1H-isoindole-4-carboxamide, cpd 18

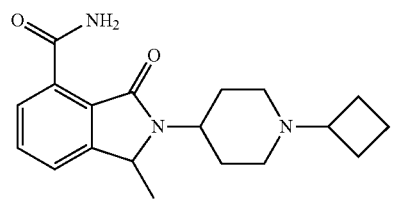 [SMILES: CC1c2cccc(C(N)=O)c2C(=O)N1C1CCN(C2CCC2)CC1]

The title compound was prepared as described in Conversion 4 replacing cyclobutanone for cyclohexanone. ¹H NMR (400 MHz, DMSO-d₆) δ ppm 10.68 (br. s., 1H), 8.18 (dd, J=0.98, 7.57 Hz, 1H), 7.76-7.80 (m, 1H), 7.69-7.75 (m, 1H), 7.66 (br. s., 1H), 4.79 (q, J=6.43 Hz, 1H), 3.70-3.88 (m, 1H), 2.83-2.96 (m, 2H), 2.66-2.77 (m, 1H), 1.91-2.23 (m, 4H), 1.70-1.85 (m, 5H), 1.62 (br. s., 2H), 1.50 (d, J=6.59 Hz, 3H). ESI(+) MS: m/z 328 (MH⁺).

1-Methyl-3-oxo-2-[1-(1H-pyrrol-2-ylmethyl)piperidin-4-yl]-2,3-dihydro-1H-isoindole-4-carboxamide, cpd 19

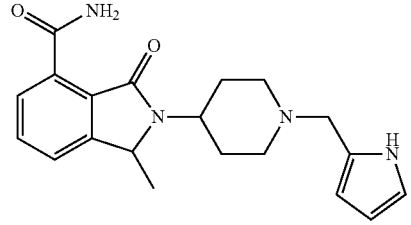 [SMILES: CC1c2cccc(C(N)=O)c2C(=O)N1C1CCN(Cc2ccc[nH]2)CC1]

The title compound was prepared as described in Conversion 4 replacing 1H-pyrrole-2-carbaldehyde for cyclohexanone.

¹H NMR (400 MHz, DMSO-d₆) δ ppm 10.68 (br. s., 1H), 10.64 (br. s., 1H), 8.18 (dd, J=1.10, 7.57 Hz, 1H), 7.75-7.81 (m, 1H), 7.67-7.75 (m, 1H), 7.65 (br. s., 1H), 6.64 (br. s., 1H), 5.93 (br. s., 1H), 5.88 (br. s., 1H), 4.78 (q, J=6.59 Hz, 1H), 3.70-3.85 (m, 1H), 3.43 (br. s., 2H), 2.86-3.00 (m, 2H), 1.87-2.30 (m, 4H), 1.75 (t, J=8.79 Hz, 2H), 1.49 (d, J=6.59 Hz, 3H). ESI(+) MS: m/z 353 (MH⁺).

1-Methyl-3-oxo-2-[1-(thiophen-2-ylmethyl)piperidin-4-yl]-2,3-dihydro-1H-isoindole-4-carboxamide, cpd 20

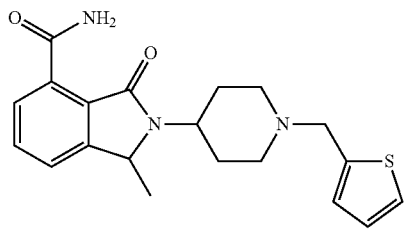

The title compound was prepared as described in Conversion 4 replacing thiophene-2-carbaldehyde for cyclohexanone.

¹H NMR (400 MHz, DMSO-d₆) δ ppm 10.68 (br. s., 1H), 8.18 (dd, J=0.98, 7.57 Hz, 1H), 7.75-7.80 (m, 1H), 7.68-7.75 (m, 1H), 7.65 (br. s., 1H), 7.48 (br. s., 1H), 7.33 (br. s., 1H), 7.08 (br. s., 1H), 4.79 (q, J=6.71 Hz, 1H), 3.79 (t, J=11.29 Hz, 1H), 3.52 (br. s., 2H), 2.88-3.00 (m, 2H), 1.92-2.27 (m, 4H), 1.67-1.82 (m, 2H), 1.50 (d, J=6.59 Hz, 3H). ESI(+) MS: m/z 370 (MH⁺).

2-[1-(Cyclohexylmethyl)piperidin-4-yl]-1-methyl-3-oxo-2,3-dihydro-1H-isoindole-4-carboxamide, cpd 21

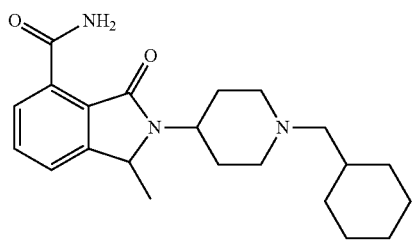 [SMILES: CC1c2cccc(C(N)=O)c2C(=O)N1C1CCN(CC2CCCCC2)CC1]

The title compound was prepared as described in Conversion 4 replacing cyclohexanecarbaldehyde for cyclohexanone.

¹H NMR (400 MHz, DMSO-d₆) δ ppm 10.69 (br. s., 1H), 8.18 (dd, J=0.92, 7.51 Hz, 1H), 7.75-7.79 (m, 1H), 7.68-7.75 (m, 1H), 7.62-7.68 (m, 1H), 4.79 (q, J=6.55 Hz, 1H), 3.65-3.84 (m, 1H), 2.84-2.97 (m, 2H), 1.50 (d, J=6.59 Hz, 3H), 0.74-0.91 (m, 2H). ESI(+) MS: m/z 370 (MH⁺).

2-[1-(Cyclohex-3-en-1-ylmethyl)piperidin-4-yl]-1-methyl-3-oxo-2,3-dihydro-1H-isoindole-4-carboxamide, cpd

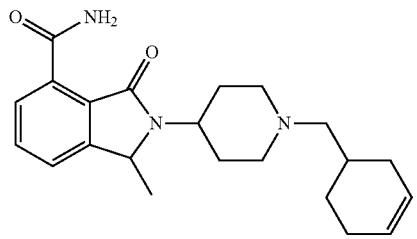 [SMILES: CC1c2cccc(C(N)=O)c2C(=O)N1C1CCN(CC2CC=CCC2)CC1]

The title compound was prepared as described in Conversion 4 replacing cyclohex-3-enecarbaldehyde for cyclohexanone.

¹H NMR (400 MHz, DMSO-d₆) δ ppm 10.69 (br. s., 1H), 8.18 (dd, J=0.79, 7.63 Hz, 1H), 7.76-7.80 (m, 1H), 7.70-7.76 (m, 1H), 7.66 (br. s., 1H), 5.60-5.69 (m, 2H), 4.80 (d, J=6.59 Hz, 1H), 3.79 (br. s., 2H), 2.90-3.03 (m, 4H), 1.50 (d, J=6.71 Hz, 3H). ESI(+) MS: m/z 368 (MH⁺).

2-{1-[(3-Fluoropyridin-4-yl)methyl]piperidin-4-yl}-1-methyl-3-oxo-2,3-dihydro-1H-isoindole-4-carboxamide, cpd 23

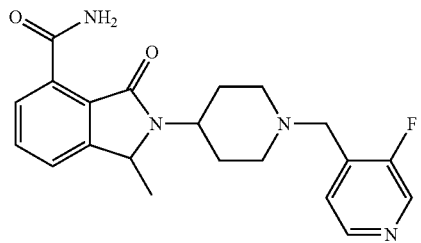 [SMILES: CC1c2cccc(C(N)=O)c2C(=O)N1C1CCN(Cc2ccncc2F)CC1]

The title compound was prepared as described in Conversion 4 replacing 3-fluoro-pyridine-4-carbaldehyde for cyclohexanone.

¹H NMR (400 MHz, DMSO-d₆) δ ppm 10.67 (br. s., 1H), 8.52 (d, J=1.59 Hz, 1H), 8.41-8.44 (m, 1H), 8.18 (dd, J=1.04, 7.63 Hz, 1H), 7.75-7.80 (m, 1H), 7.69-7.74 (m, 1H), 7.66 (br. s., 1H), 7.53 (d, J=11.11 Hz, 1H), 4.73-4.83 (m, 1H), 3.80 (d, J=4.52 Hz, 1H), 3.64 (s, 2H), 2.94 (d, J=15.38 Hz, 2H), 2.06-2.35 (m, 5H), 1.69-1.85 (m, 2H), 1.51 (d, J=6.59 Hz, 3H). ESI(+) MS: m/z 383 (MH⁺).

1-Methyl-2-{1-[(1-methyl-1H-pyrrol-2-yl)methyl]piperidin-4-yl}-3-oxo-2,3-dihydro-1H-isoindole-4-carboxamide, cpd 24

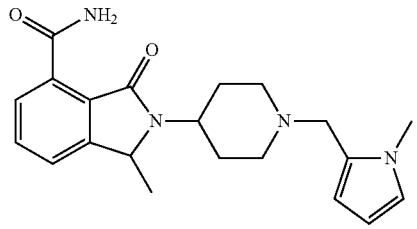 [SMILES: CC1c2cccc(C(N)=O)c2C(=O)N1C1CCN(Cc2cccn2C)CC1]

The title compound was prepared as described in Conversion 4 replacing 1-methyl-1H-pyrrole-2-carbaldehyde for cyclohexanone.

$^1$H NMR (400 MHz, DMSO-d$_6$) δ ppm 10.67 (br. s., 1H), 8.17 (dd, J=1.10, 7.57 Hz, 1H), 7.77 (d, J=7.60 Hz, 1H), 7.71 (t, J=7.60 Hz, 1H), 7.65 (br. s., 1H), 6.66 (t, J=2.01 Hz, 1H), 5.87 (d, J=1.95 Hz, 2H), 4.78 (d, J=6.59 Hz, 1H), 3.70-3.88 (m, 1H), 3.61 (s, 3H), 3.41 (s, 2H), 2.89-3.02 (m, 2H), 2.09-2.26 (m, 1H), 1.92-2.09 (m, 3H), 1.75 (t, J=12.80 Hz, 2H), 1.49 (d, J=6.59 Hz, 3H). ESI(+) MS: m/z 367 (MH$^+$).

1-Methyl-2-{1-[3-(methylsulfanyl)propyl]piperidin-4-yl}-3-oxo-2,3-dihydro-1H-isoindole-4-carboxamide, cpd 25

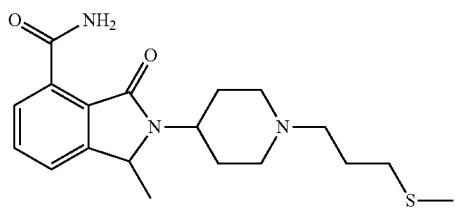 [SMILES: CSCCCN1CCC(N2C(=O)c3c(C(N)=O)cccc3C2C)CC1]

The title compound was prepared as described in Conversion 4 replacing 1-(3-methylsulfanyl-propyl)-piperidin-4-one for cyclohexanone.

$^1$H NMR (400 MHz, DMSO-d$_6$) δ ppm 10.68 (br. s., 1H), 8.18 (dd, J=1.04, 7.63 Hz, 1H), 7.78 (d, J=7.60 Hz, 1H), 7.72 (t, J=7.60 Hz, 1H), 7.65 (br. s., 1H), 4.79 (q, J=6.59 Hz, 1H), 3.80 (t, J=11.11 Hz, 1H), 2.96 (t, J=10.19 Hz, 2H), 2.38 (t, J=7.32 Hz, 2H), 2.20 (q, J=11.80 Hz, 1H), 2.05 (s, 3H), 2.00 (quin, J=12.00 Hz, 3H), 1.75 (t, J=11.00 Hz, 2H), 1.70 (quin, J=7.00 Hz, 2H), 1.50 (d, J=6.59 Hz, 3H). ESI(+) MS: m/z 362 (MH$^+$).

2-[1-(1H-Imidazol-2-ylmethyl)piperidin-4-yl]-1-methyl-3-oxo-2,3-dihydro-1H-isoindole-4-carboxamide, cpd 26

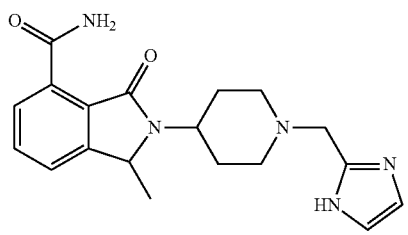 [SMILES: CC1c2cccc(C(N)=O)c2C(=O)N1C1CCN(Cc2ncc[nH]2)CC1]

The title compound was prepared as described in Conversion 4 replacing 1H-imidazole-2-carbaldehyde for cyclohexanone.

$^1$H NMR (400 MHz, DMSO-d$_6$) δ ppm 11.84 (br. s., 1H), 10.69 (br. s., 1H), 8.18 (dd, J=1.16, 7.63 Hz, 1H), 3.53 (s, 2H), 1.50 (d, J=6.71 Hz, 3H). ESI(+) MS: m/z 354 (MH$^+$).

2-{1-[(2-Chloropyridin-3-yl)methyl]piperidin-4-yl}-1-methyl-3-oxo-2,3-dihydro-1H-isoindole-4-carboxamide, cpd 27

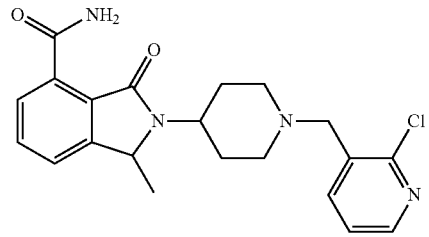 [SMILES: CC1c2cccc(C(N)=O)c2C(=O)N1C1CCN(Cc2cccnc2Cl)CC1]

The title compound was prepared as described in Conversion 4 replacing 2-chloro-pyridine-3-carbaldehyde for cyclohexanone.

$^1$H NMR (400 MHz, DMSO-d$_6$) δ ppm 10.68 (br. s., 1H), 8.32 (dd, J=1.71, 4.64 Hz, 1H), 8.18 (dd, J=0.98, 7.57 Hz, 1H), 7.96 (dd, J=1.65, 7.38 Hz, 1H), 7.78 (d, J=7.60 Hz, 1H), 7.72 (t, J=7.57 Hz, 1H), 7.66 (br. s., 1H), 7.46 (dd, J=4.82, 7.63 Hz, 1H), 4.80 (q, J=6.63 Hz, 1H), 3.74-3.93 (m, J=11.90, 11.90 Hz, 1H), 3.61 (s, 2H), 2.94 (t, J=10.44 Hz, 2H), 1.77 (t, J=12.21 Hz, 2H), 1.52 (d, J=6.71 Hz, 3H). ESI(+) MS: m/z 399 (MH$^+$).

1-Methyl-3-oxo-2-{1-[3-(1H-pyrazol-1-yl)benzyl]piperidin-4-yl}-2,3-dihydro-1H-isoindole-4-carboxamide, cpd

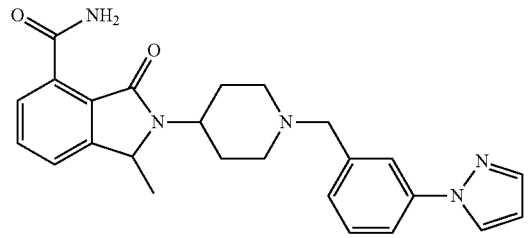 [SMILES: CC1c2cccc(C(N)=O)c2C(=O)N1C1CCN(Cc2cccc(-n3cccn3)c2)CC1]

The title compound was prepared as described in Conversion 4 replacing 3-pyrazol-1-yl-benzaldehyde for cyclohexanone.

$^1$H NMR (400 MHz, DMSO-d$_6$) ppm 10.68 (br. s., 1H), 8.50 (d, J=2.08 Hz, 1H), 8.18 (dd, J=1.04, 7.63 Hz, 1H), 7.81 (s, 1H), 7.76-7.79 (m, 1H), 7.75 (d, J=1.59 Hz, 1H), 7.72 (d, J=8.06 Hz, 0H), 7.69-7.74 (m, 1H), 7.65 (br. s., 1H), 7.46 (t, J=7.75 Hz, 1H), 7.28 (d, J=7.45 Hz, 1H), 6.54 (dd, J=1.83, 2.32 Hz, 1H), 4.80 (q, J=6.51 Hz, 1H), 3.82 (br. s., 1H), 3.59 (s, 2H), 2.90-3.08 (m, 2H), 1.77 (br. s., 2H), 1.51 (d, J=6.71 Hz, 3H). ESI(+) MS: m/z 430 (MH$^+$).

1-Methyl-2-{1-[(5-methylfuran-2-yl)methyl]piperidin-4-yl}-3-oxo-2,3-dihydro-1H-isoindole-4-carboxamide, cpd

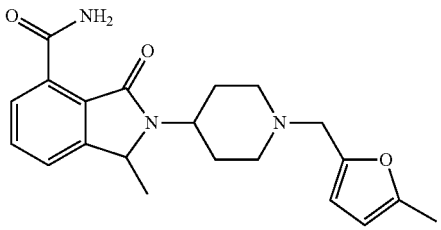 [SMILES: Cc1ccc(CN2CCC(N3C(=O)c4c(C(N)=O)cccc4C3C)CC2)o1]

The title compound was prepared as described in Conversion 4 replacing 5-methyl-furan-2-carbaldehyde for cyclohexanone.

$^1$H NMR (400 MHz, DMSO-d$_6$) δ ppm 10.67 (br. s., 1H), 8.18 (dd, J=0.85, 7.57 Hz, 1H), 7.77 (d, J=7.60 Hz, 1H), 7.71 (t, J=7.60 Hz, 1H), 7.65 (br. s., 1H), 6.15 (br. s., 1H), 5.99 (br. s., 1H), 4.78 (q, J=6.71 Hz, 1H), 3.78 (br. s., 1H), 3.45 (br. s., 2H), 2.81-3.06 (m, 2H), 2.24 (s, 3H), 2.12-2.27 (m, OH), 2.04 (br. s., 3H), 1.75 (br. s., 2H), 1.49 (d, J=6.71 Hz, 3H). ESI(+) MS: m/z 368 (MH$^+$).

1-Methyl-3-oxo-2-{1-[(3-phenyl-1H-pyrazol-5-yl)methyl]piperidin-4-yl}-2,3-dihydro-1H-isoindole-4-carboxamide, cpd 30

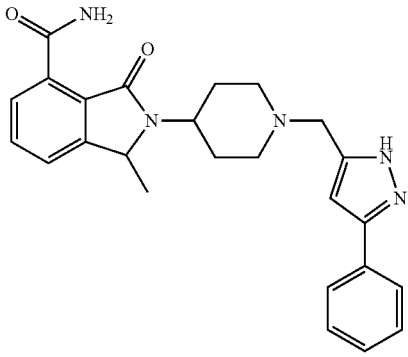 [SMILES: CC1c2cccc(C(N)=O)c2C(=O)N1C1CCN(Cc2cc(-c3ccccc3)n[nH]2)CC1]

The title compound was prepared as described in Conversion 4 replacing 5-phenyl-2H-pyrazole-3-carbaldehyde for cyclohexanone.

$^1$H NMR (400 MHz, DMSO-d$_6$) δ ppm 10.67 (br. s., 1H), 8.17 (dd, J=1.22, 7.57 Hz, 1H), 7.77 (d, J=7.60 Hz, 1H), 7.71 (t, J=7.60 Hz, 1H), 7.64 (br. s., 1H), 4.79 (q, J=6.88 Hz, 1H), 3.82 (br. s., 1H), 3.42 (s, 2H), 2.92-3.11 (m, 2H), 2.11-2.29 (m, 2H), 1.94-2.10 (m, 3H), 1.65-1.86 (m, 2H), 1.49 (d, J=6.59 Hz, 3H). ESI(+) MS: m/z 430 (MH$^+$).

2-{1-[(5-Bromothiophen-2-yl)methyl]piperidin-4-yl}-1-methyl-3-oxo-2,3-dihydro-1H-isoindole-4-carboxamide, cpd 31

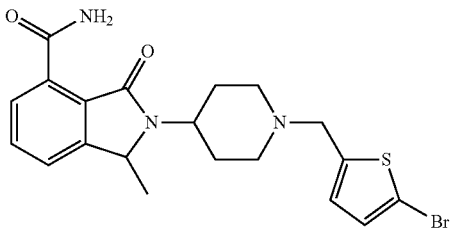 [SMILES: CC1c2cccc(C(N)=O)c2C(=O)N1C1CCN(Cc2ccc(Br)s2)CC1]

The title compound was prepared as described in Conversion 4 replacing 5-bromo-thiophene-2-carbaldehyde for cyclohexanone.

$^1$H NMR (400 MHz, DMSO-d$_6$) δ ppm 10.66 (br. s., 1H), 8.18 (dd, J=1.04, 7.63 Hz, 1H), 7.75-7.81 (m, 1H), 7.69-7.75 (m, 1H), 7.61-7.69 (m, 1H), 7.06 (d, J=3.54 Hz, 1H), 6.84 (d, J=2.93 Hz, 1H), 4.79 (q, J=6.63 Hz, 1H), 3.80 (br. s., 1H), 3.69 (br. s., 2H), 2.98 (br. s., 2H), 1.76 (br. s., 2H), 1.50 (d, J=6.59 Hz, 3H). ESI(+) MS: m/z 439 (MH$^+$).

2-[1-(3-Hydroxybenzyl)piperidin-4-yl]-1-methyl-3-oxo-2,3-dihydro-1H-isoindole-4-carboxamide, cpd 32

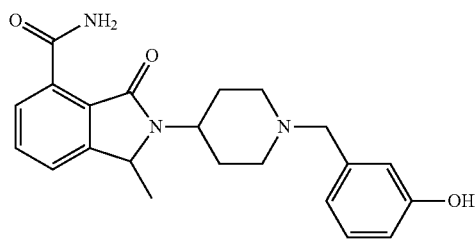 [SMILES: CC1c2cccc(C(N)=O)c2C(=O)N1C1CCN(Cc2cccc(O)c2)CC1]

The title compound was prepared as described in Conversion 4 replacing 3-hydroxy-benzaldehyde for cyclohexanone.

$^1$H NMR (400 MHz, DMSO-d$_6$) δ ppm 10.68 (br. s., 1H), 9.26 (s, 1H), 8.18 (dd, J=0.98, 7.57 Hz, 1H), 7.75-7.80 (m, 1H), 7.69-7.75 (m, 1H), 7.65 (br. s., 1H), 7.10 (t, J=7.75 Hz, 1H), 6.76 (t, J=1.95 Hz, 1H), 6.72 (d, J=7.69 Hz, 1H), 6.63 (ddd, J=0.73, 2.32, 8.06 Hz, 1H), 4.79 (q, J=6.55 Hz, 1H), 3.79 (tt, J=3.81, 11.93 Hz, 1H), 3.41 (br. s., 2H), 2.92 (br. s., 1H), 2.24 (qd, J=4.15, 12.30 Hz, 1H), 2.08 (qd, J=4.15, 12.30 Hz, 1H), 2.02 (q, J=12.00 Hz, 2H), 1.75 (t, J=12.39 Hz, 2H), 1.51 (d, J=6.59 Hz, 3H). ESI(+) MS: m/z 380 (MH$^+$).

2-{1-[2-(Difluoromethoxy)benzyl]piperidin-4-yl}-1-methyl-3-oxo-2,3-dihydro-1H-isoindole-4-carboxamide, cpd 33

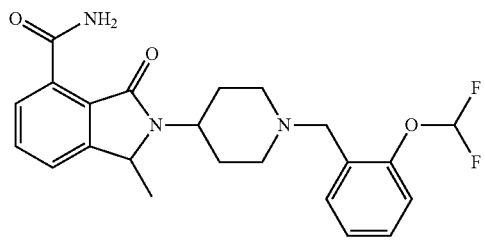 [SMILES: CC1c2cccc(C(N)=O)c2C(=O)N1C1CCN(Cc2ccccc2OC(F)F)CC1]

The title compound was prepared as described in Conversion 4 replacing 2-difluoromethoxy-benzaldehyde for cyclohexanone.

$^1$H NMR (400 MHz, DMSO-d$_6$) δ ppm 10.68 (br. s., 1H), 8.18 (dd, J=0.98, 7.57 Hz, 1H), 7.74-7.80 (m, 1H), 7.68-7.74 (m, 1H), 7.65 (br. s., 1H), 7.50 (dd, J=1.65, 7.26 Hz, 1H), 7.35 (td, J=1.80, 7.50 Hz, 1H), 7.27 (td, J=0.85, 7.45 Hz, 1H), 7.19 (d, J=8.06 Hz, 1H), 7.16 (t, J=75.00 Hz, 1H), 4.79 (q, J=6.51

Hz, 1H), 3.82 (br. s., 1H), 3.54 (s, 2H), 2.89-3.03 (m, 2H), 1.64-1.87 (m, 2H), 1.50 (d, J=6.59 Hz, 3H). ESI(+) MS: m/z 430 (MH+).

2-(1-{[5-(Hydroxymethyl)furan-2-yl]methyl}piperidin-4-yl)-1-methyl-3-oxo-2,3-dihydro-1H-isoindole-4-carboxamide, cpd 34

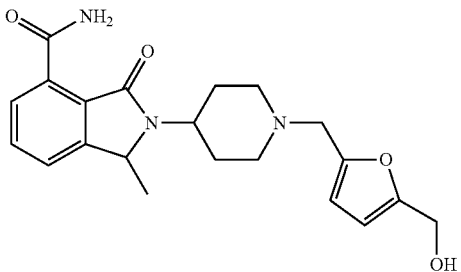 [SMILES: CC1c2cccc(C(N)=O)c2C(=O)N1C1CCN(Cc2ccc(CO)o2)CC1]

The title compound was prepared as described in Conversion 4 replacing 5-hydroxymethyl-furan-2-carbaldehyde for cyclohexanone.

$^1$H NMR (400 MHz, DMSO-d$_6$) δ ppm 10.67 (br. s., 1H), 8.17 (dd, J=1.10, 7.69 Hz, 1H), 7.75-7.81 (m, 1H), 7.68-7.75 (m, 1H), 7.65 (br. s., 1H), 6.21 (br. s., 2H), 5.15 (t, J=5.74 Hz, 1H), 4.78 (q, J=6.63 Hz, 1H), 4.36 (d, J=5.49 Hz, 2H), 3.79 (br. s., 1H), 3.49 (br. s., 2H), 2.95 (t, J=9.58 Hz, 2H), 1.66-1.85 (m, 2H), 1.50 (d, J=6.59 Hz, 3H). ESI(+) MS: m/z 384 (MH+).

Example 3

Step l+e

Methyl 4-fluoro-2-iodo-6-methylbenzoate

4-Fluoro-2-methylbenzoic acid (5.0 gr, 32.4 mmol), palladium(II) acetate (0.364 g, 1.62 mmol), iodobenzene diacetate (12.54 g, 38.92 mmol) and elemental iodine (9.88 g, 38.92 mmol) were dissolved in N,N-dimethylformamide (130 mL) and stirred at 100° C. overnight. The reaction mixture was cooled to room temperature, diluted with methyl-tert-butylether and aqueous hydrochloric acid and washed with 10% sodium metabisolfite aqueous solution. Organic phase was treated with 2N aqueous sodium hydroxide. The resulting aqueous phase was treated with aqueous hydrochloric acid up to acidic pH and extracted with methyl-tert-butylether. The organic phase was washed with brine, dried over sodium sulfate and concentrated. So obtained iodinated benzoic acid (6.9 g, 24.6 mmol) was dissolved in N,N-dimethylformamide (50 mL) and methyliodide (3 mL, 49.2 mmol) and potassium carbonate (5 g, 36.9 mmol) were added. The reaction mixture was stirred overnight at room temperature, diluted with methyl-tert-butylether and washed with water, 1M sodium hydroxide, water and brine. Solvent was removed under reduced pressure and the crude was purified by flash chromatography (n-hexane/diethyl ether 100:2) to give title compound (5.9 g, 63% yield).

$^1$H NMR (400 MHz, DMSO-d$_6$) δ ppm 2.27 (s, 3H) 3.86 (s, 3H) 7.21-7.27 (m, 1H) 7.63 (m, J=8.18, 2.44, 0.40, 0.40, 0.40 Hz, 1H).

Example 4

Step q

1-Cyclohexyl-N-[(1S)-1-(furan-2-yl)ethyl]piperidin-4-amine (1S)-1-(Furan-2-yl)ethanamine (0.55 gr, 5 mmol) and 1-cyclohexylpiperidin-4-one (0.91 gr, 5 mmol) were dissolved in dry dichloromethane (20 mL) in the presence of triethylamine (2 mL, 15 mmol) and titanium(IV) chloride (1M in dichloromethane, 2.5 mmol, 2.5 mL). Reaction mixture was stirred under nitrogen atmosphere for 16 hours. After dilution with methanol (10 mL), sodium cyanoborohydride was added (0.95 gr, 25 mmol) and the resulting reaction mixture was stirred for 4 hours. After dilution with ethyl acetate, the organic phase was washed with 15% ammonium hydroxide and evaporated to dryness. Title compound (0.72 gr, Y=52%) was isolated by column chromatography (dichloromethane/methanol/7N ammonia in methanol 96:2:2)

$^1$H NMR (400 MHz, DMSO-d$_6$) δ ppm 1.26 (s, 3H) 3.84-3.93 (m, 1H) 6.17 (d, J=3.17 Hz, 1H) 6.34 (dd, J=3.17, 1.83 Hz, 1H) 7.51 (dd, J=1.71, 0.85 Hz, 1H)

Steps o-p (1S)-2-(1-Cyclohexylpiperidin-4-yl)-1-methyl-3-oxo-2,3-dihydro-1H-isoindole-4-carboxylic acid 1-Cyclohexyl-N-[(1S)-1-(furan-2-yl)ethyl]piperidin-4-amine (0.3 gr, 1.08 mmol) and maleic anhydride (0.13 gr, 1.3 mmol) in toluene (10 mL) were stirred at reflux for 16 hours. Solvent was evaporated and the residue was dissolved in aqueous 37% hydrochloric acid (5 mL) and stirred at 100° C. for 2 hours. Volatiles were evaporated affording crude title product that was used for the next step without further purification ESI(+) MS: m/z 357 (MH+).

Step i"

(1S)-2-(1-Cyclohexylpiperidin-4-yl)-1-methyl-3-oxo-2,3-dihydro-1H-isoindole-4-carboxamide, cpd 4

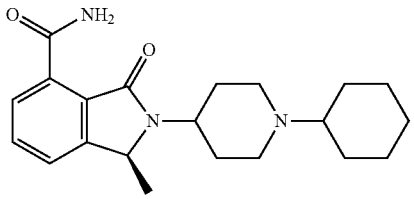 [SMILES: C[C@H]1c2cccc(C(N)=O)c2C(=O)N1C1CCN(C2CCCCC2)CC1]

(1S)-2-(1-Cyclohexylpiperidin-4-yl)-1-methyl-3-oxo-2,3-dihydro-1H-isoindole-4-carboxylic acid (0.15 gr, 0.42 mmol), hydroxybenzotriazole ammonium salt (0.13 gr, 0.84 mmol) and 1-ethyl-3-(3'-dimethylamino) carbodiimide hydrochloric acid salt (0.16 gr, 0.84 mmol) were dissolved in a mixture of tetrahydrofuran (6 mL) and triethylamine (0.23 mL, 1.68 mmol) and stirred under nitrogen atmosphere for 16 hours. Volatiles were evaporated and the crude was dissolved in dichloromethane and washed with 15% ammonium hydroxide. The organic phase was dried over anhydrous sodium sulfate and concentrated in vacuo. The crude was purified by flash chromatography (dichloromethane/methanol/7N ammonia in methanol 100:3:1) to afford the title compound (0.060 g, 40%) as a white solid.

91% e.e. was evaluated by preparative chiral-HPLC (first eluting peak) in comparison with racemic mixture (Cpd 3) by using Chiralcel OD 50×500 mm 20 µm as column system and n-hexane/ethanol/methanol 80:10:10 as eluant.

$^1$H NMR (400 MHz, DMSO-d$_6$) δ ppm 1.10 (d, 1H) 1.13-1.29 (m, 4H) 1.50 (d, J=6.59 Hz, 3H) 1.53-1.65 (m, 1H) 1.65-1.83 (m, 4H) 1.91-2.03 (m, 1H) 2.07-2.19 (m, 1H) 2.22-2.33 (m, 2H) 2.85-2.98 (m, 2H) 3.71-3.82 (m, 1H) 4.75-4.83 (m, 1H) 7.65 (br. s., 1H) 7.69-7.74 (m, 1H) 7.75-7.79 (m, 1H) 8.18 (dd, J=7.63, 1.04 Hz, 1H) 10.70 (br. s., 1H)

Probe Experimental Preparation

Step u

2-Methylamino-N-(6-oxo-5,6-dihydro-phenanthridin-2-yl)-acetamide

To a stirred suspension of 2-chloro-N-(6-oxo-5,6-dihydro-phenanthridin-2-yl)-acetamide (XXIV, Lg=Cl) (150 mg, 0.52 mmol) in dimethylformamide (1.4 mL), a 33% solution of methylamine in ethanol was added (9 mL, 72 mmol). The reaction mixture was stirred at room temperature for 3 hours. The ethanol was then evaporated under reduced pressure and the mixture was diluted with diethyl ether and filtered. A light-yellow solid was then collected, washed with diethyl ether then with cold water and dried. 2-Methylamino-N-(6-oxo-5,6-dihydro-phenanthridin-2-yl)-acetamide was obtained in moderate yield (100 mg, 68%).

$^1$H NMR (400 MHz, DMSO-d$_6$) δ ppm 11.68 (s, 1H), 10.33 (br. s., 1H), 8.61 (d, J=2.1 Hz, 1H), 8.34 (dd, J=7.9, 1.1 Hz, 1H), 8.26 (d, J=8.2 Hz, 1H), 7.89 (ddd, J=8.2, 7.1, 1.4 Hz, 1H), 7.70 (dd, J=8.7, 2.2 Hz, 1H), 7.67 (ddd, J=7.9, 7.2, 0.7 Hz, 1H), 7.35 (d, J=8.8 Hz, 1H), 3.68 (s, 2H), 2.54 (s, 3H).

Step v (3-{[(6-oxo-5,6-dihydro-phenanthridin-2-ylcarbamoyl)-methyl]-amino}-propyl)-carbamic acid tert-butyl ester To a stirred suspension of 2-chloro-N-(6-oxo-5,6-dihydro-phenanthridin-2-yl)-acetamide (XXIV, Lg=Cl) (50 mg, 0.17 mmol) in N,N-dimethylformamide (2 mL), (3-amino-propyl)-carbamic acid tert-butyl ester (0.09 mL, 0.51 mmol) and triethylamine (0.036 mL, 0.26 mmol) were added. The reaction mixture was stirred at room temperature overnight, evaporated to dryness and then purified through by preparative HPLC on a Waters X Terra RP 18 (19×250 mm, 5 µm) column. Mobile phase A was 0.05% ammonium hydroxide/acetonitrile:95/5 and mobile phase B was acetonitrile/water:95/5. Gradient from 10 to 75% B in 15 min. Fractions containing the desired compound were dried, affording 32 mg (44% yield) of (3-{[(6-oxo-5,6-dihydro-phenanthridin-2-ylcarbamoyl)-methyl]-amino}-propyl)-carbamic acid tert-butyl ester.

$^1$H NMR (400 MHz, DMSO-d$_6$) δ ppm 11.65 (s, 1H), 10.09 (br. s., 1H), 8.63 (d, J=2.0 Hz, 1H), 8.33 (dd, J=7.9, 1.2 Hz, 1H), 8.28 (d, J=8.2 Hz, 1H), 8.12-8.12 (m, 1H), 7.88 (ddd, J=8.2, 7.1, 1.4 Hz, 1H), 7.72 (dd, J=8.8, 2.0 Hz, 1H), 7.66 (ddd, J=8.0, 7.1, 0.7 Hz, 1H), 7.33 (d, J=8.8 Hz, 1H), 6.83 (t, J=5.7 Hz, 1H), 3.47 (br. s., 2H), 3.02 (q, J=6.8 Hz, 2H), 2.68 (t, J=7.3 Hz, 2H), 1.63 (quin, J=6.9 Hz, 2H), 1.37 (s, 9H).

(6-{[(6-oxo-5,6-dihydro-phenanthridin-2-ylcarbamoyl)-methyl]-amino}-hexyl)-carbamic acid tert-butyl ester To a stirred suspension of 2-chloro-N-(6-oxo-5,6-dihydro-phenanthridin-2-yl)-acetamide (XXIV, Lg=Cl) (65 mg, 0.23 mmol) in N,N-dimethylformamide (2 mL), (6-amino-hexyl)-carbamic acid tert-butyl ester hydrochloride (175 mg, 0.69 mmol) and triethylamine (0.097 mL, 0.69 mmol) were added. The reaction mixture was stirred at room temperature overnight, diluted with dichloromethane, and the resulting solution was washed with water then brine, dried over sodium sulfate and evaporated to dryness. The crude was purified by preparative HPLC on Waters X Terra RP 18 (19×250 mm, 5 µm) column. Mobile phase A was 0.05% ammonium hydroxide/acetonitrile:95/5 and mobile phase B was acetonitrile/water:95/5. Gradient from 10 to 75% B in 15 min. Fractions containing the desired compound were dried, affording 50 mg (47% yield) of (6-{[(6-oxo-5,6-dihydro-phenanthridin-2-ylcarbamoyl)-methyl]-amino}-hexyl)-carbamic acid tert-butyl ester.

$^1$H NMR (400 MHz, DMSO-d$_6$) δ ppm 11.62 (br. s., 1H), 9.90 (br. s., 1H), 8.65 (d, J=1.7 Hz, 1H), 8.33 (dd, J=8.5, 1.2 Hz, 1H), 8.30 (d, J=8.0 Hz, 1H), 7.88 (ddd, J=8.3, 7.1, 1.1 Hz, 1H), 7.74 (dd, J=8.7, 1.9 Hz, 1H), 7.65 (t, J=7.6 Hz, 1H), 7.31 (d, J=8.7 Hz, 1H), 6.73 (t, J=5.5 Hz, 1H), 3.27-3.33 (m, 2H), 2.89 (q, J=6.5 Hz, 2H), 2.55 (t, J=7.0 Hz, 2H), 1.97-2.61 (m, 1H), 1.17-1.51 (m, 8H), 1.36 (s, 9H).

Step z 2-(3-Amino-propylamino)-N-(6-oxo-5,6-dihydro-phenanthridin-2-yl)-acetamide hydrochloride (3-{[(6-oxo-5,6-dihydro-phenanthridin-2-ylcarbamoyl)-methyl]-amino}-propyl)-carbamic acid tert-butyl ester (32 mg, 0.075 mmol) was dissolved in dichloromethane (1 mL) and 4N hydrochloric acid in dioxane (1 mL) was added. The reaction mixture was stirred at room temperature overnight and then evaporated, affording 32 mg (97% yield) of 2-(3-amino-propylamino)-N-(6-oxo-5,6-dihydro-phenanthridin-2-yl)-acetamide bis-hydrochloride.

$^1$H NMR (400 MHz, DMSO-d$_6$) δ ppm 11.72 (s, 1H), 10.90 (s, 1H), 9.29 (d, J=0.6 Hz, 2H), 8.62 (d, J=2.0 Hz, 1H), 8.35 (dd, J=7.9, 1.2 Hz, 1H), 8.22 (d, J=8.2 Hz, 1H), 7.98 (br. s., 3H), 7.91 (ddd, J=8.2, 7.1, 1.3 Hz, 1H), 7.69 (dd, J=8.8, 2.2 Hz, 1H), 7.68 (ddd, J=7.9, 7.2, 0.9 Hz, 1H), 7.38 (d, J=8.8 Hz, 1H), 4.00 (t, J=4.5 Hz, 2H), 3.11 (br. s., 2H), 2.92 (sxt, J=6.4 Hz, 2H), 2.00 (quin, J=7.6 Hz, 2H).

2-(6-Amino-hexylamino)-N-(6-oxo-5,6-dihydro-phenanthridin-2-yl)-acetamide trifluoroacetate (6-{[(6-oxo-5,6-dihydro-phenanthridin-2-ylcarbamoyl)-methyl]-amino}-hexyl)-carbamic acid tert-butyl ester was dissolved in dichloromethane (5 mL) and trifluoroacetic acid (1.5 mL) was added. The reaction mixture was stirred at room temperature overnight, evaporated, taken up with diethyl ether, filtered and the collected solid was dried under vacuum to afford 30 mg (65% yield) of 2-(6-amino-hexylamino)-N-(6-oxo-5,6-dihydro-phenanthridin-2-yl)-acetamide bis-trifluoroacetate as a light-yellow solid.

$^1$H NMR (400 MHz, DMSO-d$_6$) δ ppm 11.72 (s, 1H), 10.67 (s, 1H), 8.93 (dt, J=10.7, 5.4 Hz, 2H), 8.58 (d, J=2.1 Hz, 1H), 8.35 (dd, J=8.1, 1.2 Hz, 1H), 8.22 (d, J=8.2 Hz, 1H), 7.91 (ddd, J=8.2, 7.1, 1.4 Hz, 1H), 7.69 (ddd, J=7.9, 7.2, 0.7 Hz, 1H), 7.65 (dd, J=9.0, 2.3 Hz, 1H), 7.67 (br. s., 3H), 7.38 (d, J=8.7 Hz, 1H), 3.99 (t, J=5.4 Hz, 2H), 2.95-3.06 (m, 2H), 2.72-2.85 (m, 2H), 1.64 (quin, J=7.1 Hz, 2H), 1.53 (quin, J=7.0 Hz, 2H), 1.33 (dt, J=6.9, 3.4 Hz, 4H).

Step ii

9-Dimethylamino-11,11-dimethyl-1-(3-{methyl-[(6-oxo-5,6-dihydro-phenanthridin-2-ylcarbamoyl)-methyl]-carbamoyl}-propyl)-2,3,4,11-tetrahydro-naphtho[2,3-g]quinolinium trifluoroacetate (cmpd. P1)

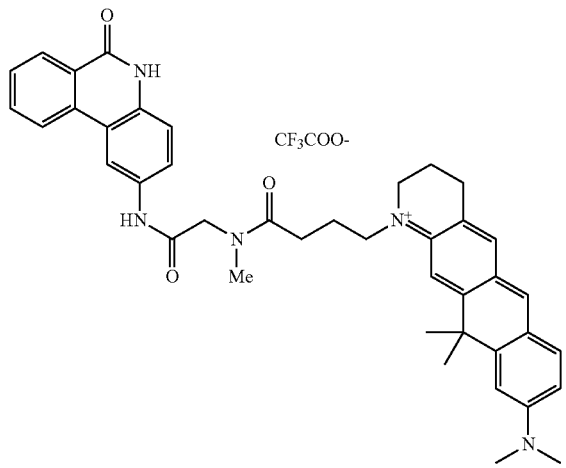 [SMILES: CN(CC(=O)Nc1ccc2[nH]c(=O)c3ccccc3c2c1)C(=O)CCC[N+]1=c2cc3c(cc2CCC1)=Cc1ccc(N(C)C)cc1C3(C)C ; "CF3COO-"]

To a stirred solution of 2-methylamino-N-(6-oxo-5,6-dihydro-phenanthridin-2-yl)-acetamide (3.65 mg, 0.013 mmol) in N,N-dimethylformamide (0.5 mL), N,N-diisopropylethylamine (0.0067 mL, 0.039 mmol) and ATTO 610 NHS ester (XXVII) were added under nitrogen, and the reaction was stirred at room temperature for 3 hours. The mixture was then evaporated, and the resulting crude was purified by preparative HPLC on Hypersil (21×250 mm, 5 µm) column. Mobile phase A was 0.1% trifluoroacetic acid/acetonitrile: 95/5 and mobile phase B was acetonitrile/water:95/5. Gradient from 0 to 70% B in 20 min. Fractions containing the desired compound were dried, affording 1.6 mg of 9-dimethylamino-11,11-dimethyl-1-(3-{methyl-[(6-oxo-5,6-dihydro-phenanthridin-2-ylcarbamoyl)-methyl]-carbamoyl}-propyl)-2,3,4,11-tetrahydro-naphtho[2,3-g]quinolinium trifluoroacetate (cmpd. P1).

MS calculated: 654.3444; MS found: 654.3447
ESI(+) MS: m/z 654 (M+).

According to this same methodology, but employing the suitable starting materials, the following compounds were prepared:

9-Dimethylamino-11,11-dimethyl-1-[3-(3-{[(6-oxo-5,6-dihydro-phenanthridin-2-ylcarbamoyl)-methyl]-amino}-propylcarbamoyl)-propyl]-2,3,4,11-tetrahydro-naphtho[2,3-g]quinolinium trifluoroacetate (cmpd. P2)

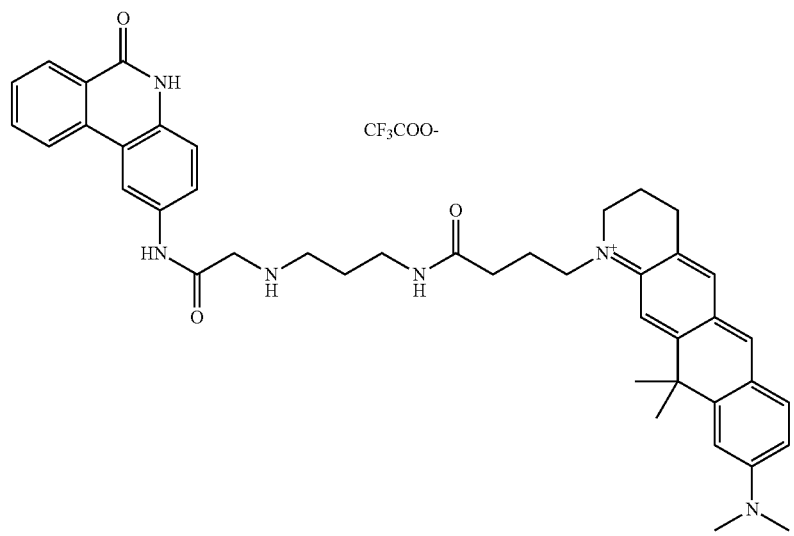 [SMILES: CN(C)c1ccc2c(c1)C(C)(C)c1cc3c(cc1=C2)CCC[N+]=3CCCC(=O)NCCCNCC(=O)Nc1ccc2[nH]c(=O)c3ccccc3c2c1 ; "CF3COO-"]

MS calculated: 697.3866; MS found: 697.3864
ESI(+) MS: m/z 697 (M+).

9-Dimethylamino-11,11-dimethyl-1-[3-(6-{[(6-oxo-5,6-dihydro-phenanthridin-2-ylcarbamoyl)-methyl]-amino}-hexylcarbamoyl)-propyl]-2,3,4,11-tetrahydro-naphtho[2,3-g]quinolinium trifluoroacetate (cmpd. P3)

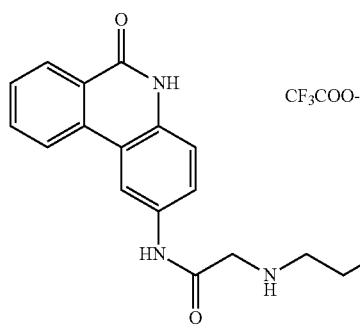
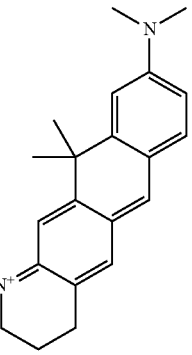

MS calculated: 739.4337; MS found: 739.4333
ESI(+) MS: m/z 739 ($M^+$).

The invention claimed is:

1. A compound of formula (I):

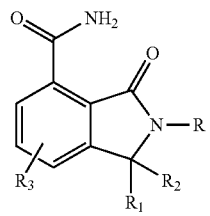

(I)

wherein

R is an optionally substituted $C_3$-$C_7$ cycloalkyl, heterocyclyl, aryl or heteroaryl group;

$R_1$ and $R_2$ are independently hydrogen atom, or a linear or branched $C_1$-$C_6$ alkyl, with the proviso that $R_1$ and $R_2$ are not both hydrogen atoms;

$R_3$ is hydrogen or halogen atom or a pharmaceutically acceptable salt thereof.

2. A compound of formula (I) according to claim 1, characterized in that R is an optionally substituted $C_3$-$C_7$ cycloalkyl, heterocyclyl, aryl or heteroaryl group, the optional substituents being one or more halogen, cyano, an optionally further substituted linear or branched $C_1$-$C_6$ alkyl, $C_3$-$C_7$ cycloalkyl, heterocyclyl, aryl, heteroaryl, $C_3$-$C_7$ cycloalkyl-$C_1$-$C_6$ alkyl, heterocyclyl-$C_1$-$C_6$ alkyl, aryl-$C_1$-$C_6$ alkyl or heteroaryl-$C_1$-$C_6$ alkyl group, oxo (=O), the optional further substituents being one or more halogen, $C_1$-$C_6$ alkyl, aryl or heterocyclyl group, oxo (=O), and $R_1$, $R_2$, $R_3$, $R_4$, $R_5$, $R_6$, $R_7$, $R_8$ and $R_9$ are as defined in claim 1, or a pharmaceutically acceptable salt thereof.

3. A compound of formula (I) according to claim 1, characterized in that R is an optionally substituted $C_3$-$C_7$ cycloalkyl, heterocyclyl, aryl or heteroaryl group, the optional substituents being one or more halogen, cyano, an optionally further substituted linear or branched $C_1$-$C_6$ alkyl, $C_3$-$C_7$ cycloalkyl, heterocyclyl, aryl, heteroaryl or $C_3$-$C_7$ cycloalkyl-$C_1$-$C_6$ alkyl, heterocyclyl-$C_1$-$C_6$ alkyl, aryl-$C_1$-$C_6$ alkyl or heteroaryl-$C_1$-$C_6$ alkyl group, oxo (=O), the optional further substituents being one or more halogen, $C_1$-$C_6$ alkyl, aryl or heterocyclyl group, oxo (=O);

and $R_1$ is hydrogen atom, and $R_2$ is a linear or branched $C_1$-$C_6$ alkyl, and $R_3$, $R_4$, $R_5$, $R_6$, $R_7$, $R_8$ and $R_9$ are as defined in claim 1, or a pharmaceutically acceptable salt thereof.

4. A compound of formula (I) according to claim 1, characterized in that R is an optionally substituted heterocyclyl or aryl group, the optional substituents being, one or more, optionally further substituted linear or branched $C_1$-$C_6$ alkyl, $C_3$-$C_7$ cycloalkyl, heterocyclyl, aryl, heteroaryl, $C_3$-$C_7$ cycloalkyl-$C_1$-$C_6$ alkyl, heterocyclyl-$C_1$-$C_6$ alkyl, aryl-$C_1$-$C_6$ alkyl or heteroaryl-$C_1$-$C_6$ alkyl group, and, the optional further substituents being one or more halogen, $C_1$-$C_6$ alkyl, aryl or heterocyclyl group, oxo (=O);

$R_1$ and $R_2$ are independently hydrogen atom or a $C_1$-$C_6$ alkyl group, with the proviso that they are not both hydrogen atoms;

$R_3$ is hydrogen or halogen atom;

$R_5$, $R_6$ and $R_9$ are as defined in claim 1, or a pharmaceutically acceptable salt thereof.

5. A compound of formula (I) according to claim 1, characterized in that R is an optionally substituted piperidinyl or phenyl group, the optional substituents being, one or more, optionally further substituted methyl, ethyl, propyl, cyclohexyl, cyclopentyl, cyclobutyl, morpholinyl, piperazinyl, pyrazolyl, cyclohexyl-methyl, cyclohexenyl-methyl, piperidinyl-methyl, benzyl, pyridyl-methyl, pyrrolyl-methyl, pyrazolyl-methyl, imidazolyl-methyl, thienyl-methyl, indolyl-methyl, thiazolyl-methyl, furyl-methyl group or $COR_4$; the optional further substituents being one or more bromine, fluorine, chlorine atom or isopropyl, methyl, phenyl, morpholinyl, or piperidinyl, hydroxy-methyl group or oxo (=O);

$R_1$ and $R_2$ are independently hydrogen atom or a methyl group, with the proviso that they are not both hydrogen atoms;

$R_3$ is hydrogen or fluorine atom;

and $R_5$, $R_6$, $R_8$, and $R_9$ are as defined in claim 1, or a pharmaceutically acceptable salt thereof.

6. A compound of formula (I) according to claim 1, selected from the group consisting of:

tert-butyl 4-(4-carbamoyl-1-methyl-3-oxo-1,3-dihydro-2H-isoindol-2-yl)piperidine-1-carboxylate, 1-methyl-3-oxo-2-(piperidin-4-yl)-2,3-dihydro-1H-isoindole-4-carboxamide, 2-(1-cyclohexylpiperidin-4-yl)-1-methyl-3-oxo-2,3-dihydro-1H-isoindole-4-carboxamide, (1S)-2-(1-cyclohexylpiperidin-4-yl)-1-methyl-3-oxo-2,3-dihydro-1H-isoindole-4-carboxamide,
(1R)-2-(1-cyclohexylpiperidin-4-yl)-1-methyl-3-oxo-2,3-dihydro-1H-isoindole-4-carboxamide,
2-[1-(4,4-difluorocyclohexyl)piperidin-4-yl]-1-methyl-3-oxo-2,3-dihydro-1H-isoindole-4-carboxamide,
2-[1-(1H-indol-5-ylmethyl)piperidin-4-yl]-1-methyl-3-oxo-2,3-dihydro-1H-isoindole-4-carboxamide,
1-methyl-3-oxo-2-(1-{[1-(propan-2-yl)-1H-indol-3-yl]methyl}piperidin-4-yl)-2,3-dihydro-1H-isoindole-4-carboxamide,
1-methyl-3-oxo-2-[1-(pyridin-2-ylmethyl)piperidin-4-yl]-2,3-dihydro-1H-isoindole-4-carboxamide,
2-(1-{[4-(benzyloxy)-1H-indol-3-yl]methyl}piperidin-4-yl)-1-methyl-3-oxo-2,3-dihydro-1H-isoindole-4-carboxamide,
1-methyl-2-{1-[(4-methyl-1,3-thiazol-5-yl)methyl]piperidin-4-yl}-3-oxo-2,3-dihydro-1H-isoindole-4-carboxamide,
2-[1-(2,4-difluorobenzyl)piperidin-4-yl]-1-methyl-3-oxo-2,3-dihydro-1H-isoindole-4-carboxamide,
2-(1-cyclopentylpiperidin-4-yl)-1-methyl-3-oxo-2,3-dihydro-1H-isoindole-4-carboxamide,
1-methyl-2-{1-[(6-methylpyridin-2-yl)methyl]piperidin-4-yl}-3-oxo-2,3-dihydro-1H-isoindole-4-carboxamide,
2-[1-(furan-2-ylmethyl)piperidin-4-yl]-1-methyl-3-oxo-2,3-dihydro-1H-isoindole-4-carboxamide,
1-methyl-3-oxo-2-{1-[3-(piperidin-1-yl)benzyl]piperidin-4-yl}-2,3-dihydro-1H-isoindole-4-carboxamide,
1-methyl-2-(1-{[6-(morpholin-4-yl)pyridin-2-yl]methyl}piperidin-4-yl)-3-oxo-2,3-dihydro-1H-isoindole-4-carboxamide,
2-(1-cyclobutylpiperidin-4-yl)-1-methyl-3-oxo-2,3-dihydro-1H-isoindole-4-carboxamide,
1-methyl-3-oxo-2-[1-(1H-pyrrol-2-ylmethyl)piperidin-4-yl]-2,3-dihydro-1H-isoindole-4-carboxamide,
1-methyl-3-oxo-2-[1-(thiophen-2-ylmethyl)piperidin-4-yl]-2,3-dihydro-1H-isoindole-4-carboxamide,
2-[1-(cyclohexylmethyl)piperidin-4-yl]-1-methyl-3-oxo-2,3-dihydro-1H-isoindole-4-carboxamide,
2-[1-(cyclohex-3-en-1-ylmethyl)piperidin-4-yl]-1-methyl-3-oxo-2,3-dihydro-1H-isoindole-4-carboxamide,
2-{1-[(3-fluoropyridin-4-yl)methyl]piperidin-4-yl}-1-methyl-3-oxo-2,3-dihydro-1H-isoindole-4-carboxamide,
1-methyl-2-{1-[(1-methyl-1H-pyrrol-2-yl)methyl]piperidin-4-yl}-3-oxo-2,3-dihydro-1H-isoindole-4-carboxamide,
1-methyl-2-{1-[3-(methylsulfanyl)propyl]piperidin-4-yl}-3-oxo-2,3-dihydro-1H-isoindole-4-carboxamide,
2-[1-(1H-imidazol-2-ylmethyl)piperidin-4-yl]-1-methyl-3-oxo-2,3-dihydro-1H-isoindole-4-carboxamide,
2-{1-[(2-chloropyridin-3-yl)methyl]piperidin-4-yl}-1-methyl-3-oxo-2,3-dihydro-1H-isoindole-4-carboxamide,
1-methyl-3-oxo-2-{1-[3-(1H-pyrazol-1-yl)benzyl]piperidin-4-yl}-2,3-dihydro-1H-isoindole-4-carboxamide,
1-methyl-2-{1-[(5-methylfuran-2-yl)methyl]piperidin-4-yl}-3-oxo-2,3-dihydro-1H-isoindole-4-carboxamide,
1-methyl-3-oxo-2-{1-[(3-phenyl-1H-pyrazol-5-yl)methyl]piperidin-4-yl}-2,3-dihydro-1H-isoindole-4-carboxamide,
2-{1-[(5-bromothiophen-2-yl)methyl]piperidin-4-yl}-1-methyl-3-oxo-2,3-dihydro-1H-isoindole-4-carboxamide,
2-[1-(3-hydroxybenzyl)piperidin-4-yl]-1-methyl-3-oxo-2,3-dihydro-1H-isoindole-4-carboxamide,
2-{1-[2-(difluoromethoxy)benzyl]piperidin-4-yl}-1-methyl-3-oxo-2,3-dihydro-1H-isoindole-4-carboxamide,
2-(1-{[5-(hydroxymethyl)furan-2-yl]methyl}piperidin-4-yl)-1-methyl-3-oxo-2,3-dihydro-1H-isoindole-4-carboxamide,
1-methyl-2-[4-(morpholin-4-yl)phenyl]-3-oxo-2,3-dihydro-1H-isoindole-4-carboxamide,
1-methyl-3-oxo-2-[4-(piperidin-1-yl)phenyl]-2,3-dihydro-1H-isoindole-4-carboxamide,
1-methyl-2-[4-(4-methylpiperazin-1-yl)phenyl]-3-oxo-2,3-dihydro-1H-isoindole-4-carboxamide,
1-methyl-3-oxo-2-[4-(piperidin-1-ylmethyl)phenyl]-2,3-dihydro-1H-isoindole-4-carboxamide,
tert-butyl 4-(4-carbamoyl-6-fluoro-1-methyl-3-oxo-1,3-dihydro-2H-isoindol-2-yl)piperidine-1-carboxylate,
6-fluoro-1-methyl-3-oxo-2-(piperidin-4-yl)-2,3-dihydro-1H-isoindole-4-carboxamide,
2-(1-cyclohexylpiperidin-4-yl)-6-fluoro-1-methyl-3-oxo-2,3-dihydro-1H-isoindole-4-carboxamide,
2-[1-(4,4-difluorocyclohexyl)piperidin-4-yl]-6-fluoro-1-methyl-3-oxo-2,3-dihydro-1H-isoindole-4-carboxamide,
6-fluoro-2-[1-(1H-indol-5-ylmethyl)piperidin-4-yl]-1-methyl-3-oxo-2,3-dihydro-1H-isoindole-4-carboxamide,
6-fluoro-1-methyl-3-oxo-2-[1-(pyridin-2-ylmethyl)piperidin-4-yl]-2,3-dihydro-1H-isoindole-4-carboxamide,
6-fluoro-1-methyl-2-{1-[(4-methyl-1,3-thiazol-5-yl)methyl]piperidin-4-yl}-3-oxo-2,3-dihydro-1H-isoindole-4-carboxamide,
2-[1-(2,4-difluorobenzyl)piperidin-4-yl]-6-fluoro-1-methyl-3-oxo-2,3-dihydro-1H-isoindole-4-carboxamide,
2-(1-cyclopentylpiperidin-4-yl)-6-fluoro-1-methyl-3-oxo-2,3-dihydro-1H-isoindole-4-carboxamide,
6-fluoro-1-methyl-2-{1-[(6-methylpyridin-2-yl)methyl]piperidin-4-yl}-3-oxo-2,3-dihydro-1H-isoindole-4-carboxamide,
6-fluoro-2-[1-(furan-2-ylmethyl)piperidin-4-yl]-1-methyl-3-oxo-2,3-dihydro-1H-isoindole-4-carboxamide,
6-fluoro-1-methyl-3-oxo-2-{1-[3-(piperidin-1-yl)benzyl]piperidin-4-yl}-2,3-dihydro-1H-isoindole-4-carboxamide,
6-fluoro-1-methyl-2-(1-{[6-(morpholin-4-yl)pyridin-2-yl]methyl}piperidin-4-yl)-3-oxo-2,3-dihydro-1H-isoindole-4-carboxamide,
2-(1-cyclobutylpiperidin-4-yl)-6-fluoro-1-methyl-3-oxo-2,3-dihydro-1H-isoindole-4-carboxamide,
6-fluoro-1-methyl-3-oxo-2-[1-(1H-pyrrol-2-ylmethyl)piperidin-4-yl]-2,3-dihydro-1H-isoindole-4-carboxamide,
6-fluoro-1-methyl-3-oxo-2-[1-(thiophen-2-ylmethyl)piperidin-4-yl]-2,3-dihydro-1H-isoindole-4-carboxamide,
2-[1-(cyclohexylmethyl)piperidin-4-yl]-6-fluoro-1-methyl-3-oxo-2,3-dihydro-1H-isoindole-4-carboxamide,
2-[1-(cyclohex-3-en-1-ylmethyl)piperidin-4-yl]-6-fluoro-1-methyl-3-oxo-2,3-dihydro-1H-isoindole-4-carboxamide,
6-fluoro-2-{1-[(3-fluoropyridin-4-yl)methyl]piperidin-4-yl}-1-methyl-3-oxo-2,3-dihydro-1H-isoindole-4-carboxamide,
6-fluoro-1-methyl-2-{1-[(1-methyl-1H-pyrrol-2-yl)methyl]piperidin-4-yl}-3-oxo-2,3-dihydro-1H-isoindole-4-carboxamide,
6-fluoro-2-[1-(1H-imidazol-2-ylmethyl)piperidin-4-yl]-1-methyl-3-oxo-2,3-dihydro-1H-isoindole-4-carboxamide, 2-{1-[(2-chloropyridin-3-yl)methyl]piperidin-4-yl}-6-fluoro-1-methyl-3-oxo-2,3-dihydro-1H-isoindole-4-carboxamide,
6-fluoro-1-methyl-2-{1-[(5-methylfuran-2-yl)methyl]piperidin-4-yl}-3-oxo-2,3-dihydro-1H-isoindole-4-carboxamide,
2-{1-[(5-bromothiophen-2-yl)methyl]piperidin-4-yl}-6-fluoro-1-methyl-3-oxo-2,3-dihydro-1H-isoindole-4-carboxamide,
6-fluoro-2-(1-{[5-(hydroxymethyl)furan-2-yl]methyl}piperidin-4-yl)-1-methyl-3-oxo-2,3-dihydro-1H-isoindole-4-carboxamide,
(1S)-2-(1-cyclohexylpiperidin-4-yl)-6-fluoro-1-methyl-3-oxo-2,3-dihydro-1H-isoindole-4-carboxamide,
(1R)-2-(1-cyclohexylpiperidin-4-yl)-6-fluoro-1-methyl-3-oxo-2,3-dihydro-1H-isoindole-4-carboxamide,
1-methyl-3-oxo-2-[4-(piperidin-4-ylmethyl)phenyl]-2,3-dihydro-1H-isoindole-4-carboxamide,
1-methyl-3-oxo-2-[4-(piperazin-1-ylmethyl)phenyl]-2,3-dihydro-1H-isoindole-4-carboxamide,
1-methyl-2-{4-[(1-methylpiperidin-4-yl)methyl]phenyl}-3-oxo-2,3-dihydro-1H-isoindole-4-carboxamide,
1-methyl-2-[3-(1-methylpiperidin-4-yl)phenyl]-3-oxo-2,3-dihydro-1H-isoindole-4-carboxamide,
1-methyl-2-[3-(4-methylpiperazin-1-yl)phenyl]-3-oxo-2,3-dihydro-1H-isoindole-4-carboxamide,
2-[4-cyclohexyl-3-(1-methylpiperidin-4-yl)phenyl]-1-methyl-3-oxo-2,3-dihydro-1H-isoindole-4-carboxamide,
2-[4-cyclohexyl-3-(4-methylpiperazin-1-yl)phenyl]-1-methyl-3-oxo-2,3-dihydro-1H-isoindole-4-carboxamide,
2-[1-(cyclohex-3-en-1-ylmethyl)piperidin-4-yl]-1-methyl-3-oxo-2,3-dihydro-1H-isoindole-4-carboxamide,
1-methyl-3-oxo-2-[1-(2,2,2-trifluoroethyl)piperidin-4-yl]-2,3-dihydro-1H-isoindole-4-carboxamide hydrate,
1-methyl-3-oxo-2-[1-(tetrahydrofuran-3-ylmethyl)piperidin-4-yl]-2,3-dihydro-1H-isoindole-4-carboxamide,
tert-butyl 3-{[4-(4-carbamoyl-1-methyl-3-oxo-1,3-dihydro-2H-isoindol-2-yl)piperidin-1-yl]methyl}azetidine-1-carboxylate,
1-methyl-2-{1-[2-methyl-2-(piperidin-1-yl)propyl]piperidin-4-yl}-3-oxo-2,3-dihydro-1H-isoindole-4-carboxamide,
2-{1-[3-(dimethylamino)-2,2-dimethylpropyl]piperidin-4-yl}-1-methyl-3-oxo-2,3-dihydro-1H-isoindole-4-carboxamide,
2-{1-[(1-ethyl-4,5-dihydro-1H-pyrazol-4-yl)methyl]piperidin-4-yl}-1-methyl-3-oxo-2,3-dihydro-1H-isoindole-4-carboxamide,
1-methyl-2-[1-(2-methylbutyl)piperidin-4-yl]-3-oxo-2,3-dihydro-1H-isoindole-4-carboxamide,
2-[1-(cyclopentylmethyl)piperidin-4-yl]-1-methyl-3-oxo-2,3-dihydro-1H-isoindole-4-carboxamide,
methyl 4-[4-(4-carbamoyl-1-methyl-3-oxo-1,3-dihydro-2H-isoindol-2-yl)piperidin-1-yl]butanoate,
1-methyl-3-oxo-2-[1-(2,2,2-trichloroethyl)piperidin-4-yl]-2,3-dihydro-1H-isoindole-4-carboxamide,
ethyl 2-{[4-(4-carbamoyl-1-methyl-3-oxo-1,3-dihydro-2H-isoindol-2-yl)piperidin-1-yl]methyl}cyclopropanecarboxylate,
2-(1-hexylpiperidin-4-yl)-1-methyl-3-oxo-2,3-dihydro-1H-isoindole-4-carboxamide,
1-methyl-2-(1-nonylpiperidin-4-yl)-3-oxo-2,3-dihydro-1H-isoindole-4-carboxamide,
2-[1-(3-cyclohexylpropyl)piperidin-4-yl]-1-methyl-3-oxo-2,3-dihydro-1H-isoindole-4-carboxamide,
1-methyl-3-oxo-2-[1-(3-phenylpropyl)piperidin-4-yl]-2,3-dihydro-1H-isoindole-4-carboxamide,
2-[1-(cyclopropylmethyl)piperidin-4-yl]-1-methyl-3-oxo-2,3-dihydro-1H-isoindole-4-carboxamide,
2-(1-heptylpiperidin-4-yl)-1-methyl-3-oxo-2,3-dihydro-1H-isoindole-4-carboxamide,
1-methyl-3-oxo-2-(1-pentylpiperidin-4-yl)-2,3-dihydro-1H-isoindole-4-carboxamide,
1-methyl-3-oxo-2-[1-(2-phenylethyl)piperidin-4-yl]-2,3-dihydro-1H-isoindole-4-carboxamide,
2-[1-(3,3-dimethylbutyl)piperidin-4-yl]-1-methyl-3-oxo-2,3-dihydro-1H-isoindole-4-carboxamide,
1-methyl-3-oxo-2-(1-propylpiperidin-4-yl)-2,3-dihydro-1H-isoindole-4-carboxamide,
2-[1-(5-hydroxypentyl)piperidin-4-yl]-1-methyl-3-oxo-2,3-dihydro-1H-isoindole-4-carboxamide,
1-methyl-3-oxo-2-[1-(2,2,2-trifluoroethyl)piperidin-4-yl]-2,3-dihydro-1H-isoindole-4-carboxamide,
2-(1-butylpiperidin-4-yl)-1-methyl-3-oxo-2,3-dihydro-1H-isoindole-4-carboxamide,
1-methyl-2-[1-(2-methylpropyl)piperidin-4-yl]-3-oxo-2,3-dihydro-1H-isoindole-4-carboxamide,
1-methyl-2-{1-[(1-methyl-1H-benzimidazol-2-yl)methyl]piperidin-4-yl}-3-oxo-2,3-dihydro-1H-isoindole-4-carboxamide,
2-[1-(2,3-dihydroxypropyl)piperidin-4-yl]-1-methyl-3-oxo-2,3-dihydro-1H-isoindole-4-carboxamide,
2-[1-(2,2-dimethylpropyl)piperidin-4-yl]-1-methyl-3-oxo-2,3-dihydro-1H-isoindole-4-carboxamide,
2-[1-(2,2-dimethylpent-4-en-1-yl)piperidin-4-yl]-1-methyl-3-oxo-2,3-dihydro-1H-isoindole-4-carboxamide,
2-(1-ethylpiperidin-4-yl)-1-methyl-3-oxo-2,3-dihydro-1H-isoindole-4-carboxamide,
1-methyl-2-[1-(3-methylbutyl)piperidin-4-yl]-3-oxo-2,3-dihydro-1H-isoindole-4-carboxamide,
2-[1-(2-ethylbutyl)piperidin-4-yl]-1-methyl-3-oxo-2,3-dihydro-1H-isoindole-4-carboxamide,
2-(1-cyclohexylpiperidin-4-yl)-1,1-dimethyl-3-oxo-2,3-dihydro-1H-isoindole-4-carboxamide,
2-(1-cyclopentylpiperidin-4-yl)-1,1-dimethyl-3-oxo-2,3-dihydro-1H-isoindole-4-carboxamide,
2-(1-cyclobutylpiperidin-4-yl)-1,1-dimethyl-3-oxo-2,3-dihydro-1H-isoindole-4-carboxamide,
2-(1-cyclohexylpiperidin-4-yl)-6-fluoro-1,1-dimethyl-3-oxo-2,3-dihydro-1H-isoindole-4-carboxamide,
2-(1-cyclopentylpiperidin-4-yl)-6-fluoro-1,1-dimethyl-3-oxo-2,3-dihydro-1H-isoindole-4-carboxamide,
2-(1-cyclobutylpiperidin-4-yl)-6-fluoro-1,1-dimethyl-3-oxo-2,3-dihydro-1H-isoindole-4-carboxamide,
2'-(1-cyclohexylpiperidin-4-yl)-3'-oxo-2',3'-dihydrospiro[cyclopropane-1,1'-isoindole]-4'-carboxamide,
2'-(1-cyclohexylpiperidin-4-yl)-6'-fluoro-3'-oxo-2',3'-dihydrospiro[cyclopropane-1,1'-isoindole]-4'-carboxamide,
2'-(1-cyclopentylpiperidin-4-yl)-3'-oxo-2',3'-dihydrospiro[cyclopropane-1,1'-isoindole]-4'-carboxamide,
2'-(1-cyclopentylpiperidin-4-yl)-6'-fluoro-3'-oxo-2',3'-dihydrospiro[cyclopropane-1,1'-isoindole]-4'-carboxamide,
2'-(1-cyclobutylpiperidin-4-yl)-3'-oxo-2',3'-dihydrospiro[cyclopropane-1,1'-isoindole]-4'-carboxamide,
2'-(1-cyclobutylpiperidin-4-yl)-6'-fluoro-3'-oxo-2',3'-dihydrospiro[cyclopropane-1,1'-isoindole]-4'-carboxamide,
2-(1-cyclohexylpiperidin-4-yl)-1-methylidene-3-oxo-2,3-dihydro-1H-isoindole-4-carboxamide, 2-(1-cyclohexylpiperidin-4-yl)-6-fluoro-1-methylidene-3-oxo-2,3-dihydro-1H-isoindole-4-carboxamide, 2-(1-cyclopentylpiperidin-4-yl)-1-methylidene-3-oxo-2,3-dihydro-1H-isoindole-4-carboxamide, 2-(1-cyclopentylpiperidin-4-yl)-6-fluoro-1-methylidene-3-oxo-2,3-dihydro-1H-isoindole-4-carboxamide, 2-(1-cyclohexylazetidin-3-yl)-1-methyl-3-oxo-2,3-dihydro-1H-isoindole-4-carboxamide, 2-(1-cyclohexylazetidin-3-yl)-6-fluoro-1-methyl-3-oxo-2,3-dihydro-1H-isoindole-4-carboxamide, 2-(1-cyclopentylazetidin-3-yl)-1-methyl-3-oxo-2,3-dihydro-1H-isoindole-4-carboxamide, 2-(1-cyclopentylazetidin-3-yl)-6-fluoro-1-methyl-3-oxo-2,3-dihydro-1H-isoindole-4-carboxamide, 2-[1-(4,4-difluorocyclohexyl)piperidin-4-yl]-6-fluoro-1-methyl-3-oxo-2,3-dihydro-1H-isoindole-4-carboxamide, 2-(1-cyclohexylpiperidin-4-yl)-6-fluoro-1-methyl-3-oxo-2,3-dihydro-1H-isoindole-4-carboxamide and 2-(1-cyclohexylpiperidin-4-yl)-6-fluoro-1,1-dimethyl-3-oxo-2,3-dihydro-1H-isoindole-4-carboxamide, or a pharmaceutically acceptable salt thereof.

7. A pharmaceutical composition comprising a therapeutically effective amount of a compound of formula (I), as defined in claim 1, and at least one pharmaceutically acceptable carrier and/or diluent.

8. A pharmaceutical composition according to claim 7 further comprising one or more chemotherapeutic agents.

9. A product comprising a compound of formula (I) as defined in claim 1 or a pharmaceutical composition thereof comprising a therapeutically effective amount of said compound and at least one pharmaceutically acceptable carrier and/or diluent, and one or more chemotherapeutic agents, as a combined preparation for simultaneous, separate or sequential use in anticancer therapy.

* * * * *